(12) United States Patent
Atiya et al.

(10) Patent No.: US 11,096,765 B2
(45) Date of Patent: Aug. 24, 2021

(54) LIGHT FIELD INTRAORAL 3D SCANNER WITH STRUCTURED LIGHT ILLUMINATION

(71) Applicant: Align Technology, Inc., San Jose, CA (US)

(72) Inventors: Yossef Atiya, Modin-Maccabim-Reut (IL); Erez Lampert, Rehovot (IL); Avi Kopelman, Palo Alto, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/446,190

(22) Filed: Jun. 19, 2019

(65) Prior Publication Data
US 2019/0388194 A1  Dec. 26, 2019

Related U.S. Application Data

(60) Provisional application No. 62/778,192, filed on Dec. 11, 2018, provisional application No. 62/775,787, (Continued)

(51) Int. Cl.
*G01B 11/30* (2006.01)
*A61C 9/00* (2006.01)
(Continued)

(52) U.S. Cl.
CPC .......... *A61C 9/006* (2013.01); *A61B 1/00096* (2013.01); *A61B 1/00172* (2013.01);
(Continued)

(58) Field of Classification Search
CPC ............ A61B 1/00096; A61B 1/00172; A61B 1/00177; A61B 1/00193; A61B 1/0615;
(Continued)

(56) References Cited

U.S. PATENT DOCUMENTS 6,697,164 B1 * 2/2004 Babayoff ........... A61B 1/00096
356/609
9,671,220 B2  6/2017 Gandyra et al.
(Continued)

FOREIGN PATENT DOCUMENTS

KR  101693158 B1  1/2017
KR  20180030322 A  3/2018
(Continued)

OTHER PUBLICATIONS

International Search Report and Written Opinion for International Patent Application No. PCT/US2019/038510 dated Nov. 26, 2019, 25 pages.
(Continued)

*Primary Examiner* — Peter B Kim
(74) *Attorney, Agent, or Firm* — Lowenstein Sandler LLP

(57) ABSTRACT

A handheld wand comprises a probe at a distal end of the elongate handheld wand. The probe includes a light projector and a light field camera. The light projector includes a light source and a pattern generator configured to generate a light pattern. The light field camera includes a light field camera sensor, the light field camera sensor comprising an image sensor comprising an array of sensor pixels, and an array of micro-lenses disposed in front of the image sensor such that each micro-lens is disposed over a sub-array of the array of sensor pixels.

26 Claims, 38 Drawing Sheets

Related U.S. Application Data filed on Dec. 5, 2018, provisional application No. 62/689,006, filed on Jun. 22, 2018.

(51) Int. Cl.
| | | |
|---|---|---|
| *G06T 7/80* | (2017.01) | |
| *G02B 27/42* | (2006.01) | |
| *G06T 17/00* | (2006.01) | |
| *H04N 9/31* | (2006.01) | |
| *G06T 7/521* | (2017.01) | |
| *A61B 1/00* | (2006.01) | |
| *A61B 1/24* | (2006.01) | |

(52) U.S. Cl.
CPC ............ *A61B 1/00193* (2013.01); *A61B 1/24* (2013.01); *G02B 27/4222* (2013.01); *G02B 27/4227* (2013.01); *G06T 7/521* (2017.01); *G06T 7/80* (2017.01); *G06T 7/85* (2017.01); *G06T 17/00* (2013.01); *H04N 9/3161* (2013.01); *G06T 2207/10024* (2013.01); *G06T 2207/10028* (2013.01); *G06T 2207/10052* (2013.01); *G06T 2207/30036* (2013.01)

(58) Field of Classification Search
CPC ......... A61B 1/24; A61C 9/006; G01B 11/245; G01B 11/2513; G01B 11/2545; G02B 27/4222; G02B 27/4227; G06T 17/00; G06T 2207/10024; G06T 2207/10028; G06T 2207/10052; G06T 2207/30036; G06T 7/521; G06T 7/80; G06T 7/85; H04N 9/3161

See application file for complete search history.

(56) References Cited

U.S. PATENT DOCUMENTS

| | | | |
|---|---|---|---|
| 2008/0101688 | A1 | 5/2008 | Quadling et al. |
| 2018/0028064 | A1 | 2/2018 | Elbaz et al. |
| 2018/0192877 | A1* | 7/2018 | Atiya .................. A61B 5/0088 |
| 2018/0296080 | A1* | 10/2018 | Glinec .................... A61B 1/24 |
| 2019/0388193 | A1* | 12/2019 | Saphier .................... G06T 7/85 |
| 2020/0060550 | A1* | 2/2020 | Pesach ................ A61B 5/0088 |

FOREIGN PATENT DOCUMENTS

| | | | | |
|---|---|---|---|---|
| WO | 2017123926 A1 | 7/2017 | | |
| WO | WO-2017125926 A2 * | 7/2017 | ............. | A61C 19/04 |

OTHER PUBLICATIONS

U.S. Appl. No. 16/446,181, Intraoral 3D Scanner Employing Multiple Miniature Cameras and Multiple Miniature Pattern Projectors, filed Jun. 19, 2019.

* cited by examiner

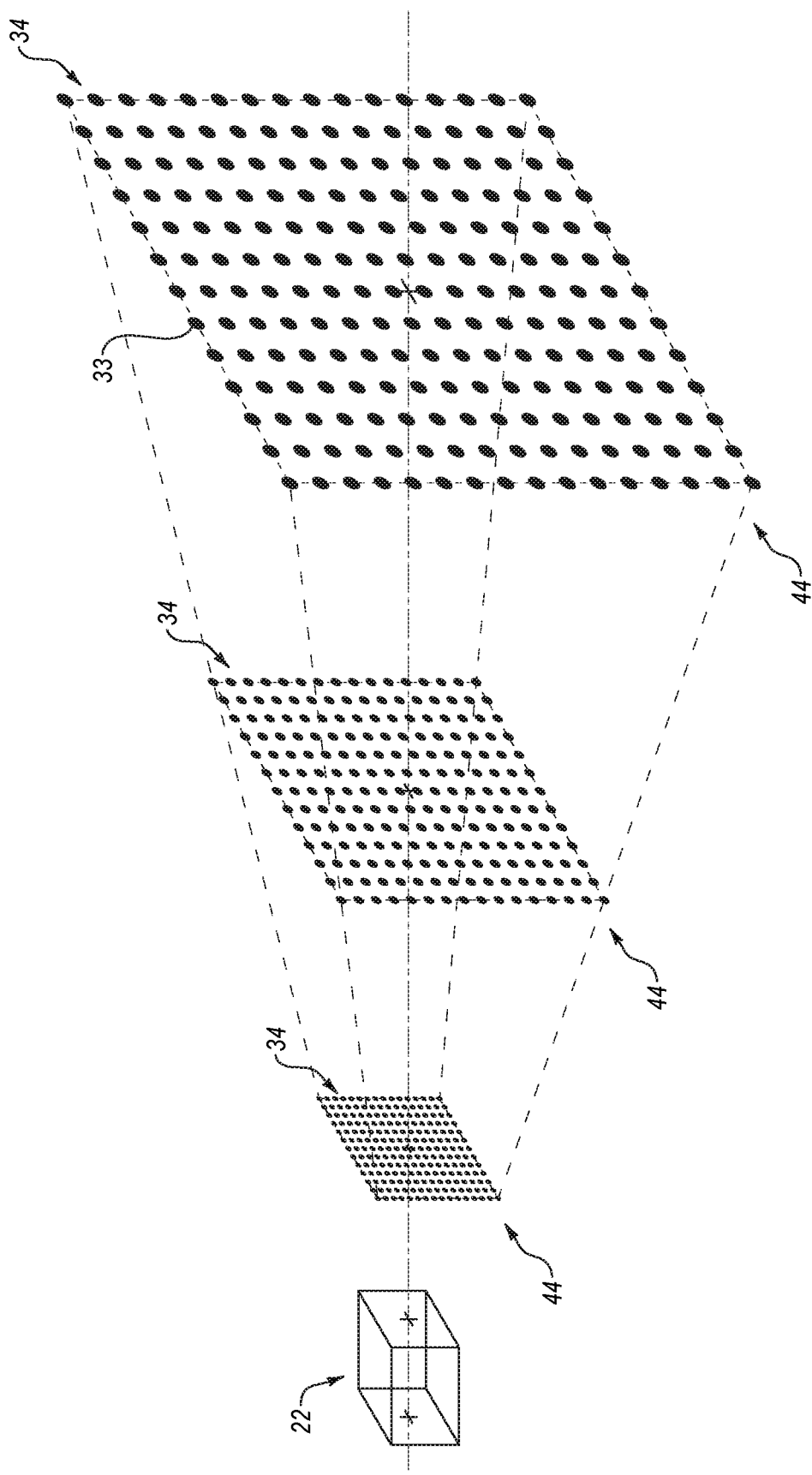

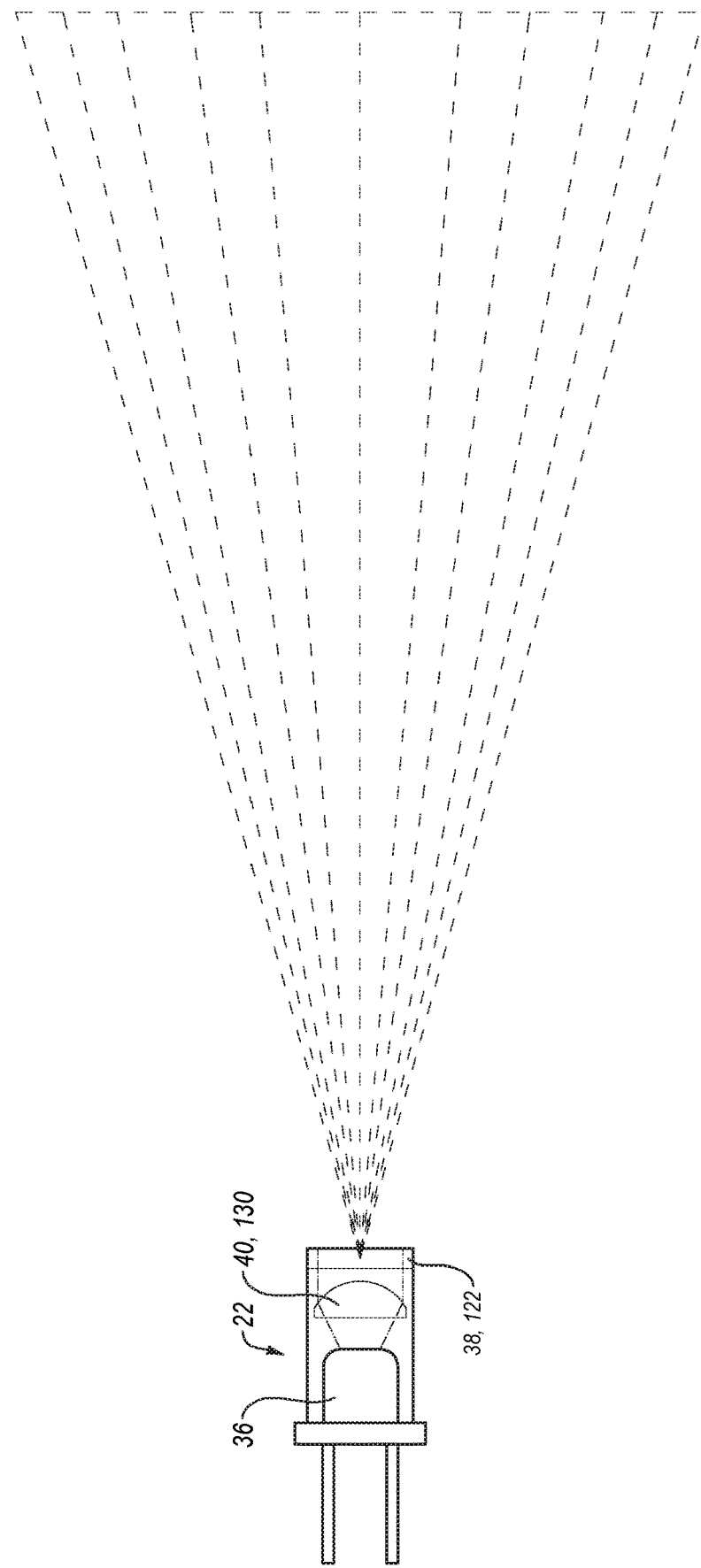

LIGHT FIELD INTRAORAL 3D SCANNER WITH STRUCTURED LIGHT ILLUMINATION

CROSS REFERENCE TO RELATED APPLICATIONS

The present application claims priority from:
(a) U.S. Provisional Application No. 62/689,006 to Saphier, filed Jun. 22, 2018, entitled, "Intraoral 3D scanner employing multiple miniature cameras and multiple miniature pattern projectors,"
(b) U.S. Provisional Application No. 62/775,787 to Atiya, filed Dec. 5, 2018, entitled, "Light field intraoral 3D scanner with structured light illumination," and
(c) U.S. Provisional Application No. 62/778,192 to Atiya, filed Dec. 11, 2018, entitled, "Light field intraoral 3D scanner with structured light illumination."

Each of these applications is assigned to the assignee of the present application and is incorporated herein by reference in its entirety for all purposes.

FIELD OF THE INVENTION

The present invention relates generally to three-dimensional imaging, and more particularly to intraoral three-dimensional imaging using structured light illumination.

BACKGROUND

Dental impressions of a subject's intraoral three-dimensional surface, e.g., teeth and gingiva, are used for planning dental procedures. Traditional dental impressions are made using a dental impression tray filled with an impression material, e.g., PVS or alginate, into which the subject bites. The impression material then solidifies into a negative imprint of the teeth and gingiva, from which a three-dimensional model of the teeth and gingiva can be formed.

Digital dental impressions utilize intraoral scanning to generate three-dimensional digital models of an intraoral three-dimensional surface of a subject. Digital intraoral scanners often use structured light three-dimensional imaging. The surface of a subject's teeth may be highly reflective and somewhat translucent, which may reduce the contrast in the structured light pattern reflecting off the teeth. Therefore, in order to improve the capture of an intraoral scan, when using a digital intraoral scanner that utilizes structured light three-dimensional imaging, a subject's teeth are frequently coated with an opaque powder prior to scanning in order to facilitate a usable level of contrast of the structured light pattern, e.g., in order to turn the surface into a scattering surface. While intraoral scanners utilizing structured light three-dimensional imaging have made some progress, additional advantages may be had.

SUMMARY OF THE INVENTION

The use of structured light three-dimensional imaging may lead to a "correspondence problem," where a correspondence between points in the structured light pattern and points seen by a camera viewing the pattern needs to be determined. One technique to address this issue is based on projecting a "coded" light pattern and imaging the illuminated scene from one or more points of view. Encoding the emitted light pattern makes portions of the light pattern unique and distinguishable when captured by a camera system. Since the pattern is coded, correspondences between image points and points of the projected pattern may be more easily found. The decoded points can be triangulated and 3D information recovered.

Applications of the present invention include systems and methods related to a three-dimensional intraoral scanning device that includes one or more cameras, and one or more pattern projectors. For example, certain applications of the present invention may be related to an intraoral scanning device having a plurality of cameras and a plurality of pattern projectors.

Further applications of the present invention include methods and systems for decoding a structured light pattern.

Still further applications of the present invention may be related to systems and methods of three-dimensional intraoral scanning utilizing non-coded structured light patterns. The non-coded structured light patterns may include uniform patterns of spots, for example.

For example, in some particular applications of the present invention, an apparatus is provided for intraoral scanning, the apparatus including an elongate handheld wand with a probe at the distal end. During a scan, the probe may be configured to enter the intraoral cavity of a subject. One or more light projectors (e.g., miniature structured light projectors) as well as one or more cameras (e.g., miniature cameras) are coupled to a rigid structure disposed within a distal end of the probe. Each of the structured light projectors transmits light using a light source, such as a laser diode. Each light projector may be configured to project a pattern of light defined by a plurality of projector rays when the light source is activated. Each camera may be configured capture a plurality of images that depict at least a portion of the projected pattern of light on an intraoral surface. In some applications, the structured light projectors may have a field of illumination of at least 45 degrees. Optionally, the field of illumination may be less than 120 degrees. Each of the structured light projectors may further include a pattern generating optical element. The pattern generating optical element may utilize diffraction and/or refraction to generate a light pattern. In some applications, the light pattern may be a distribution of discrete unconnected spots of light. Optionally, the light pattern maintains the distribution of discrete unconnected spots at all planes located between 1 mm and 30 mm from the pattern generating optical element, when the light source (e.g., laser diode) is activated to transmit light through the pattern generating optical element. In some applications, the pattern generating optical element of each structured light projector may have a light throughput efficiency, i.e., the fraction of light falling on the pattern generator that goes into the pattern, of at least 80%, e.g., at least 90%. Each of the cameras includes a camera sensor and objective optics including one or more lenses.

A laser diode light source and diffractive and/or refractive pattern generating optical elements may provide certain advantages in some applications. For example, the use of laser diodes and diffractive and/or refractive pattern generating optical elements may help maintain an energy efficient structured light projector so as to prevent the probe from heating up during use. Further, such components may help reduce costs by not necessitating active cooling within the probe. For example, present-day laser diodes may use less than 0.6 Watts of power while continuously transmitting at a high brightness (in contrast, for example, to a present-day light emitting diode (LED)). When pulsed in accordance with some applications of the present invention, these present-day laser diodes may use even less power, e.g., when pulsed with a duty cycle of 10%, the laser diodes may use less than 0.06 Watts (but for some applications the laser diodes may use at least 0.2 Watts while continuously transmitting at high brightness, and when pulsed may use even less power, e.g., when pulsed with a duty cycle of 10%, the laser diodes may use at least 0.02 Watts). Further, a diffractive and/or refractive pattern generating optical element may be configured to utilize most, if not all, the transmitted light (in contrast, for example, to a mask which stops some of the rays from hitting the object).

In particular, the diffraction- and/or refraction-based pattern generating optical element generates the pattern by diffraction, refraction, or interference of light, or any combination of the above, rather than by modulation of the light as done by a transparency or a transmission mask. In some applications, this may be advantageous as the light throughput efficiency (the fraction of light that goes into the pattern out of the light that falls on the pattern generator) is nearly 100%, e.g., at least 80%, e.g., at least 90%, regardless of the pattern "area-based duty cycle." In contrast, the light throughput efficiency of a transparency mask or transmission mask pattern generating optical element is directly related to the "area-based duty cycle." For example, for a desired "area-based duty cycle" of 100:1, the throughput efficiency of a mask-based pattern generator would be 1% whereas the efficiency of the diffraction- and/or refraction-based pattern generating optical element remains nearly 100%. Moreover, the light collection efficiency of a laser is at least 10 times higher than an LED having the same total light output, due to a laser having an inherently smaller emitting area and divergence angle, resulting in a brighter output illumination per unit area. The high efficiency of the laser and diffractive and/or refractive pattern generator may help enable a thermally efficient configuration that limits the probe from heating up significantly during use, thus reducing cost by potentially eliminating or limiting the need for active cooling within the probe. While, laser diodes and DOEs may be particularly preferable in some applications, they are by no way essential individually or in combination. Other light sources, including LEDs, and pattern generating elements, including transparency and transmission masks, may be used in other applications.

In some applications, in order to improve image capture of an intraoral scene under structured light illumination, without using contrast enhancement means such as coating the teeth with an opaque powder, the inventors have realized that a distribution of discrete unconnected spots of light (as opposed to lines, for example) may provide an improved balance between increasing pattern contrast while maintaining a useful amount of information. In some applications, the unconnected spots of light have a uniform (e.g., unchanging) pattern. Generally speaking, a denser structured light pattern may provide more sampling of the surface, higher resolution, and enable better stitching of the respective surfaces obtained from multiple image frames. However, too dense a structured light pattern may lead to a more complex correspondence problem due to there being a larger number of spots for which to solve the correspondence problem. Additionally, a denser structured light pattern may have lower pattern contrast resulting from more light in the system, which may be caused by a combination of (a) stray light that reflects off the somewhat glossy surface of the teeth and may be picked up by the cameras, and (b) percolation, i.e., some of the light entering the teeth, reflecting along multiple paths within the teeth, and then leaving the teeth in many different directions. As described further hereinbelow, methods and systems are provided for solving the correspondence problem presented by the distribution of discrete unconnected spots of light. In some applications, the discrete unconnected spots of light from each projector may be non-coded.

In some applications, the field of view of each of the cameras may be at least 45 degrees, e.g., at least 80 degrees, e.g., 85 degrees. Optionally, the field of view of each of the cameras may be less than 120 degrees, e.g., less than 90 degrees. For some applications, one or more of the cameras has a fisheye lens, or other optics that provide up to 180 degrees of viewing.

In any case, the field of view of the various cameras may be identical or non-identical. Similarly, the focal length of the various cameras may be identical or non-identical. The term "field of view" of each of the cameras, as used herein, refers to the diagonal field of view of each of the cameras. Further, each camera may be configured to focus at an object focal plane that is located between 1 mm and 30 mm, e.g., at least 5 mm and/or less than 11 mm, e.g., 9 mm-10 mm, from the lens that is farthest from the respective camera sensor. Similarly, in some applications, the field of illumination of each of the structured light projectors may be at least 45 degrees and optionally less than 120 degrees. The inventors have realized that a large field of view achieved by combining the respective fields of view of all the cameras may improve accuracy due to reduced amount of image stitching errors, especially in edentulous regions, where the gum surface is smooth and there may be fewer clear high resolution 3-D features. Having a larger field of view enables large smooth features, such as the overall curve of the tooth, to appear in each image frame, which improves the accuracy of stitching respective surfaces obtained from multiple such image frames. In some applications, the total combined field of view of the various cameras (e.g., of the intraoral scanner) is between about 20 mm and about 50 mm along the longitudinal axis of the elongate handheld wand, and about 20-40 mm in the z-axis, where the z-axis may correspond to depth. In further applications, the field of view may be at least 20 mm, at least 25 mm, at least 30 mm, at least 35 mm, or at least 40 mm along the longitudinal axis. In some embodiments, the combined field of view may change with depth (e.g., with scanning distance). For example, at a scanning distance of about 4 mm the field of view may be about 40 mm along the longitudinal axis, and at a scanning distance of about 14 mm the field of view may be about 45 mm along the longitudinal axis. If most of the motion of the intraoral scanner is done relative to the long axis (e.g., longitudinal axis) of the scanner, then overlap between scans can be substantial. In some applications, the field of view of the combined cameras is not continuous. For example, the intraoral scanner may have a first field of view separated from a second field of view by a fixed separation. The fixed separation may be, for example, along the longitudinal axis of the elongate handheld wand.

In some applications, a method is provided for generating a digital three-dimensional image of an intraoral surface. It is noted that a "three-dimensional image," as the phrase is used in the present application, is based on a three-dimensional model, e.g., a point cloud, from which an image of the three-dimensional intraoral surface is constructed. The resultant image, while generally displayed on a two-dimensional screen, contains data relating to the three-dimensional structure of the scanned object, and thus may typically be manipulated so as to show the scanned object from different views and perspectives. Additionally, a physical three-dimensional model of the scanned object may be made using the data from the three-dimensional image.

For example, one or more structured light projectors may be driven to project a distribution of discrete unconnected spots of light on an intraoral surface, and one or more cameras may be driven to capture an image of the projection. The image captured by each camera may include at least one of the spots.

Each camera includes a camera sensor that has an array of pixels, for each of which there exists a corresponding ray in 3-D space originating from the pixel whose direction is towards an object being imaged; each point along a particular one of these rays, when imaged on the sensor, will fall on its corresponding respective pixel on the sensor. As used throughout this application, including in the claims, the term used for this is a "camera ray." Similarly, for each projected spot from each projector there exists a corresponding projector ray. Each projector ray corresponds to a respective path of pixels on at least one of the camera sensors, i.e., if a camera sees a spot projected by a specific projector ray, that spot will necessarily be detected by a pixel on the specific path of pixels that corresponds to that specific projector ray. Values for (a) the camera ray corresponding to each pixel on the camera sensor of each of the cameras, and (b) the projector ray corresponding to each of the projected spots of light from each of the projectors, may be stored during a calibration process, as described hereinbelow.

Based on the stored calibration values a processor may be used to run a correspondence algorithm in order to identify a three-dimensional location for each projected spot on the surface. For a given projector ray, the processor "looks" at the corresponding camera sensor path on one of the cameras. Each detected spot along that camera sensor path will have a camera ray that intersects the given projector ray. That intersection defines a three-dimensional point in space. The processor then searches among the camera sensor paths that correspond to that given projector ray on the other cameras and identifies how many other cameras, on their respective camera sensor paths corresponding to the given projector ray, also detected a spot whose camera ray intersects with that three-dimensional point in space. As used herein throughout the present application, if two or more cameras detect spots whose respective camera rays intersect a given projector ray at the same three-dimensional point in space, the cameras are considered to "agree" on the spot being located at that three-dimensional point. Accordingly, the processor may identify three-dimensional locations of the projected pattern of light based on agreements of the two or more cameras on there being the projected pattern of light by projector rays at certain intersections. The process is repeated for the additional spots along a camera sensor path, and the spot for which the highest number of cameras "agree" is identified as the spot that is being projected onto the surface from the given projector ray. A three-dimensional position on the surface is thus computed for that spot.

Once a position on the surface is determined for a specific spot, the projector ray that projected that spot, as well as all camera rays corresponding to that spot, may be removed from consideration and the correspondence algorithm may be run again for a next projector ray. Ultimately, the identified three-dimensional locations may be used to generate a digital three-dimensional model of the intraoral surface.

In a further example, a method of generating a digital three-dimensional model of an intraoral surface may include projecting a pattern of discrete unconnected spots onto an intraoral surface of a patient using one or more light projectors disposed in a probe at a distal end of an intraoral scanner, wherein the pattern of discrete unconnected spots is non-coded. The method may further include capturing a plurality of images of the projected pattern of unconnected spots using two or more cameras disposed in the probe, decoding the plurality of images of the projected pattern in order to determine three-dimensional surface information of the intraoral surface, and using the three-dimensional surface information to generate a digital three-dimensional model of the intraoral surface. Decoding the plurality of images may include accessing calibration data that associates camera rays corresponding to pixels on a camera sensor of each of the two or more cameras to a plurality of projector rays, wherein each of the plurality of projector rays is associated with one of the discrete unconnected spots. The decoding may further include determining intersections of projector rays and camera rays corresponding to the projected pattern of discrete unconnected spots using the calibration data, wherein intersections of the projector rays and the camera rays are associated with three-dimensional points in space. The decoding may further include identifying three-dimensional locations of the projected pattern of discrete unconnected spots based on agreements of the two or more cameras on there being the projected pattern of discrete unconnected spots by projector rays at certain intersections.

There is therefore provided, in accordance with some applications of the present invention, apparatus for intraoral scanning, the apparatus including:

an elongate handheld wand including a probe at a distal end of the handheld wand;

a rigid structure disposed within a distal end of the probe;

one or more structured light projectors coupled to the rigid structure; and one or more cameras coupled to the rigid structure.

In some applications, each structured light projector may have a field of illumination of 45-120 degrees. Optionally, the one or more structured light projectors may utilize a laser diode light source. Further, the structure light projector(s) may include a beam shaping optical element. Further still, the structured light projector(s) may include a pattern generating optical element.

The pattern generating optical element may be configured to generate a distribution of discrete unconnected spots of light. The distribution of discrete unconnected spots of light may be generated at all planes located between 1 mm and 30 mm from the pattern generating optical element when the light source (e.g., laser diode) is activated to transmit light through the pattern generating optical element. In some applications, the pattern generating optical element (i) utilizes diffraction and/or refraction to generate the distribution. Optionally, the pattern generating optical element has a light throughput efficiency of at least 90%

Further, in some applications, each camera may (a) have a field of view of 45-120 degrees. The camera(s) may include a camera sensor and objective optics including one or more lenses. In some applications, the camera(s) may be configured to focus at an object focal plane that is located between 1 mm and 30 mm from the lens that is farthest from the camera sensor.

For some applications, each of the one or more cameras is configured to focus at an object focal plane that is located between 5 mm and 11 mm from the lens that is farthest from the camera sensor.

For some applications, the pattern generating optical element of each of the one or more projectors is configured to generate the distribution of discrete unconnected spots of light at all planes located between 4 mm and 24 mm from the pattern generating optical element when the light source (e.g., laser diode) is activated to transmit light through the pattern generating optical element.

For some applications, each of the one or more cameras is configured to focus at an object focal plane that is located between 4 mm and 24 mm from the lens that is farthest from the camera sensor.

For some applications, each of the structured light projectors has a field of illumination of 70-100 degrees.

For some applications, each of the cameras has a field of view of 70-100 degrees.

For some applications, each of the cameras has a field of view of 80-90 degrees.

For some applications, the apparatus further includes at least one uniform light projector, configured to project white light onto an object being scanned, and at least one of the cameras is configured to capture two-dimensional color images of the object using illumination from the uniform light projector.

For some applications, the beam shaping optical element includes a collimating lens.

For some applications, the structured light projectors and the cameras are positioned such that each structured light projector faces an object outside of the wand placed in its field of illumination. Optionally, each camera may face an object outside of the wand placed in its field of view. Further, in some applications, at least 20% of the discrete unconnected spots of light are in the field of view of at least one of the cameras.

For some applications, a height of the probe is 10-15 mm, wherein light enters the probe through a lower surface (or sensing surface) of the probe and the height of the probe is measured from the lower surface of the probe to an upper surface of the probe opposite the lower surface.

For some applications, the one or more structured light projectors is exactly one structured light projector, and the one or more cameras is exactly one camera.

For some applications, the pattern generating optical element includes a diffractive optical element (DOE).

For some applications, each DOE is configured to generate the distribution of discrete unconnected spots of light such that when the light source is activated to transmit light through the DOE, a ratio of illuminated area to non-illuminated area for each orthogonal plane in the field of illumination is 1:150-1:16.

For some applications, each DOE is configured to generate the distribution of discrete unconnected spots of light such that when the light source is activated to transmit light through the DOE, a ratio of illuminated area to non-illuminated area for each orthogonal plane in the field of illumination is 1:64-1:36.

For some applications, the one or more structured light projectors are a plurality of structured light projectors. In some applications, every spot generated by a specific DOE has the same shape. Optionally, the shape of the spots generated by at least one DOE is different from the shape of the spots generated from at least one other DOE.

For some applications, each of the one or more projectors comprises an optical element disposed between the beam shaping optical element and the DOE, the optical element being configured to generate a Bessel beam when the laser diode is activated to transmit light through the optical element, such that the discrete unconnected spots of light maintain a diameter of less than 0.06 mm through each inner surface of a sphere that is centered at the DOE and has a radius of between 1 mm and 30 mm.

For some applications, the optical element is configured to generate the Bessel beam when the laser diode is activated to transmit light through the optical element, such that the discrete unconnected spots of light maintain a diameter of less than 0.02 mm through each inner surface of a geometric sphere that is centered at the DOE and has a radius between 1 mm and 30 mm.

For some applications, each of the one or more projectors includes an optical element disposed between the beam shaping optical element and the DOE. The optical element may be configured to generate a Bessel beam when the light source is activated to transmit light through the optical element, such that the discrete unconnected spots of light maintain a small diameter through a depth range. For example, in some applications, the discrete unconnected spots of light may maintain a diameter of less than 0.06 mm through each orthogonal plane located between 1 mm and 30 mm from the DOE.

For some applications, the optical element is configured to generate a Bessel beam when the laser diode is activated to transmit light through the optical element, such that the discrete unconnected spots of light maintain a diameter of less than 0.02 mm through each orthogonal plane located between 1 mm and 30 mm from the DOE.

For some applications, the optical element is configured to generate a Bessel beam when the light source is activated to transmit light through the optical element, such that the discrete unconnected spots of light maintain a diameter of less than 0.04 mm through each orthogonal plane located between 4 mm and 24 mm from the DOE.

For some applications, the optical element is an axicon lens.

For some applications, the axicon lens is a diffractive axicon lens.

For some applications, the optical element is an annular aperture.

For some applications, the one or more structured light projectors are a plurality of structured light projectors, and the light sources of at least two of the structured light projectors are configured to transmit light at two distinct wavelengths, respectively.

For some applications, the light sources of at least three of the structured light projectors are configured to transmit light at three distinct wavelengths, respectively.

For some applications, the light sources of at least three of the structured light projectors are configured to transmit red, blue, and green light, respectively.

In some applications, the light sources comprise laser diodes.

For some applications, the one or more cameras are a plurality of cameras which are coupled to the rigid structure such that an angle between two respective optical axes of at least two of the cameras is 0-90 degrees.

For some applications, the angle between two respective optical axes of at least two of the cameras is 0-35 degrees.

For some applications, the one or more structured light projectors are a plurality of structured light projectors, which are coupled to the rigid structure such that an angle between two respective optical axes of at least two of the structured light projectors is 0-90 degrees.

For some applications, the angle between two respective optical axes of at least two of the structured light projectors is 0-35 degrees.

For some applications, each camera has a plurality of discrete preset focus positions, in each focus position the camera being configured to focus at a respective object focal plane.

For some applications, each camera includes an autofocus actuator configured to select a focus position from the discrete preset focus positions.

For some applications, each of the one or more cameras includes an optical aperture phase mask configured to extend a depth of focus of the camera such that images formed by each camera are maintained focused over all object distances located between 1 mm and 30 mm from the lens that is farthest from the camera sensor.

For some applications, the optical aperture phase mask is configured to extend the depth of focus of the camera such that the images formed by each camera are maintained focused over all object distances located between 4 mm and 24 mm from the lens that is farthest from the camera sensor.

For some applications, each of the one or more cameras is configured to capture images at a frame rate of 30-200 frames per second.

For some applications, each of the one or more cameras is configured to capture images at a frame rate of at least 75 frames per second.

For some applications, each of the one or more cameras is configured to capture images at a frame rate of at least 100 frames per second.

For some applications, the laser diode of each of the one or more projectors is configured to transmit an elliptical beam of light. A beam shaping optical element of each of the one or more projectors may include a collimating lens. Optionally, the pattern generating optical element includes a diffractive optical element (DOE) that is segmented into a plurality of sub-DOE patches arranged in an array. Each sub-DOE patch may generate a respective distribution of discrete unconnected spots of light in a different area of the field of illumination such that the distribution of discrete unconnected spots of light is generated when the light source is activated to transmit light through the segmented DOE.

For some applications, a collimating lens may be configured to generate an elliptical beam of light having a long axis of 500-700 microns and a short axis of 100-200 microns.

For some applications, the array of sub-DOE patches may be positioned to be contained within the elliptical beam of light when the laser diode is activated to transmit light through the segmented DOE.

For some applications, a cross-section of each of the sub-DOE patches is a square having a side of length 30-75 microns, the cross-section being taken perpendicular to the optical axis of the DOE.

For some applications, the plurality of sub-DOE patches are arranged in a rectangular array including 16-72 sub-DOE patches and having a longest dimension of 500-800 microns.

For some applications, the collimating lens and the segmented DOE are a single optical element, a first side of the optical element including the collimating lens, and a second side of the optical element, opposite the first side, including the segmented DOE.

For some applications, the at least one light source of each of the one or more projectors is a plurality of laser diodes. In some applications, the plurality of laser diodes may be configured to transmit light at the same wavelength.

For some applications, the plurality of laser diodes may be configured to transmit light at different wavelengths.

For some applications, the plurality of laser diodes is two laser diodes, the two laser diodes being configured to transmit light at two distinct wavelengths, respectively.

For some applications, the plurality of laser diodes is three laser diodes, the three laser diodes being configured to transmit light at three distinct wavelengths, respectively.

For some applications, the three laser diodes are configured to transmit red, blue, and green light, respectively.

For some applications:
the beam shaping optical element of each of the one or more projectors includes a collimating lens, and
the pattern generating optical element includes a compound diffractive periodic structure having a periodic structure feature size of 100-400 nm.

For some applications, the collimating lens and the compound diffractive periodic structure are a single optical element, a first side of the optical element including the collimating lens, and a second side of the optical element, opposite the first side, including the compound diffractive periodic structure.

For some applications, the apparatus further includes an axicon lens disposed between the collimating lens and the compound diffractive periodic structure, the axicon lens having an axicon head angle of 0.2-2 degrees.

For some applications, the collimating lens has a focal length of 1.2-2 mm.

For some applications:
the beam shaping optical element of each of the one or more projectors includes a collimating lens, and
the pattern generating optical element includes a micro-lens array having a numerical aperture of 0.2-0.7.

For some applications, the micro-lens array is a hexagonal micro-lens array.

For some applications, the micro-lens array is a rectangular micro-lens array.

For some applications, the collimating lens and the micro-lens array are a single optical element, a first side of the optical element including the collimating lens, and a second side of the optical element, opposite the first side, including the micro-lens array.

For some applications, the apparatus further includes an axicon lens disposed between the collimating lens and the micro-lens array, the axicon lens having an axicon head angle of 0.2-2 degrees.

For some applications, the collimating lens has a focal length of 1.2-2 mm.

For some applications:
the beam shaping optical element of each of the one or more projectors includes a collimating lens, the collimating lens having a focal length of 1.2-2 mm,
each of the one or more projectors includes an aperture ring disposed between the collimating lens and the pattern generating optical element, and
the pattern generating optical element includes a compound diffractive periodic structure having a periodic structure feature size of 100-400 nm.

For some applications:
the beam shaping optical element of each of the one or more projectors includes a lens (a) disposed between the laser diode and the pattern generating optical element, and (b) having a planar surface on a first side of the lens and an aspherical surface on a second side of the lens opposite the first side, the aspherical surface being configured to generate a Bessel beam directly from a diverging beam of light when the laser diode is activated to transmit a diverging beam of light through the lens and the pattern generating optical element, such that the discrete unconnected spots of light have a substantially uniform size at any orthogonal plane located between 1 mm and 30 mm from the pattern generating optical element.

For some applications, the aspherical surface of the lens is configured to generate a Bessel beam directly from a diverging beam of light when the laser diode is activated to transmit a diverging beam of light through the lens and the pattern generating optical element, such that the discrete unconnected spots of light have a substantially uniform size at any orthogonal plane located between 4 mm and 24 mm from the pattern generating optical element.

For some applications, the pattern generating optical element includes a compound diffractive periodic structure having a periodic structure feature size of 100-400 nm.

For some applications, the pattern generating optical element includes a micro-lens array having a numerical aperture of 0.2-0.7.

For some applications:

(a) the beam shaping optical element includes an aspherical surface on a first side of a lens, and (b) a planar surface on a second side of the lens, opposite the first side, is shaped to define the pattern generating optical element, and the aspherical surface is configured to generate a Bessel beam directly from a diverging beam of light when the laser diode is activated to transmit a diverging beam of light through the lens, such that the Bessel beam is split into an array of discrete Bessel beams when the laser diode is activated to transmit the diverging beam of light through the lens, such that the discrete unconnected spots of light have a substantially uniform size at all planes located between 1 mm and 30 mm from the lens.

For some applications, the planar surface of the lens is shaped to define the pattern generating optical element such that the Bessel beam is split into an array of discrete Bessel beams when the laser diode is activated to transmit the diverging beam of light through the lens, such that the discrete unconnected spots of light have a substantially uniform size at all planes located between 4 mm and 24 mm from the pattern generating optical element.

For some applications, the apparatuses and methods may further include:

at least one temperature sensor coupled to the rigid structure and configured to measure a temperature of the rigid structure; and a temperature control unit.

Temperature control circuitry may be configured to (a) receive data from the temperature sensor indicative of the temperature of the rigid structure, and (b) activate the temperature control unit based on the received data. The temperature control unit and circuitry may be configured to keep the probe and/or rigid structure at a temperature between 35 and 43 degrees Celsius For some applications, the temperature control unit is configured to keep the probe at a temperature between 37 and 41 degrees Celsius.

For some applications, the temperature control unit is configured to keep the temperature of the probe from varying by more than a threshold temperature change.

For some applications, the apparatus further includes:

a target such as a diffuse reflector including a plurality of regions disposed within the probe such that:

(a) each projector has at least one region of the diffuse reflector in its field of illumination, (b) each camera has at least one region of the diffuse reflector in its field of view, and (c) a plurality of the regions of the diffuse reflector are in the field of view of one of the cameras and in the field of illumination of one of the projectors.

In some applications, temperature control circuitry may be configured to (a) receive data from the cameras indicative of a position of the diffuse reflector with respect to the distribution of discrete unconnected spots of light, (b) compare the received data to a stored calibration position of the diffuse reflector, a discrepancy between (i) the received data indicative of the position of the diffuse reflector and (ii) the stored calibration position of the diffuse reflector indicating a change in temperature of the probe, and (c) regulate a temperature of the probe based on the comparison of the received data and the stored calibration position of the diffuse reflector.

There is further provided, in accordance with some applications of the present invention, a method for generating a digital three-dimensional image, the method including:

driving each one of one or more structured light projectors to project a distribution of discrete unconnected spots of light on an intraoral three-dimensional surface;

driving each one of one or more cameras to capture an image, the image including at least one of the spots, each one of the one or more cameras including a camera sensor including an array of pixels;

based on stored calibration values indicating (a) a camera ray corresponding to each pixel on the camera sensor of each one of the one or more cameras, and (b) a projector ray corresponding to each of the projected spots of light from each one of the one or more projectors, whereby each projector ray corresponds to a respective path of pixels on at least one of the camera sensors:

using a processor, running a correspondence algorithm to:

(1) for each projector ray i, identify for each detected spot j on a camera sensor path corresponding to ray i, how many other cameras, on their respective camera sensor paths corresponding to ray i, detected respective spots k corresponding to respective camera rays that intersect ray i and the camera ray corresponding to detected spot j, whereby ray i is identified as the specific projector ray that produced a detected spot j for which the highest number of other cameras detected respective spots k, and (2) compute a respective three-dimensional position on the intraoral three-dimensional surface at the intersection of projector ray i and the respective camera rays corresponding to the detected spot j and the respective detected spots k.

For some applications, running the correspondence algorithm using the processor further includes, following step (1), using the processor to:

remove from consideration projector ray i, and the respective camera rays corresponding to the detected spot j and the respective detected spots k; and run the correspondence algorithm again for a next projector ray i.

For some applications, driving each one of the one or more structured light projectors to project a distribution of discrete unconnected spots of light includes driving each one of the structured light projectors to project 400—3000 discrete unconnected spots of light onto the intraoral three-dimensional surface.

For some applications, driving each one of the one or more structured light projectors to project a distribution of discrete unconnected spots of light includes driving a plurality of structured light projectors to each project a distribution of discrete unconnected spots of light, wherein:

(a) at least two of the structured light projectors are configured to transmit light at different wavelengths, and (b) the stored calibration values indicating a camera ray corresponding to each pixel on the camera sensor for each of the wavelengths.

For some applications, driving each one of the one or more structured light projectors to project a distribution of discrete unconnected spots of light includes driving a plurality of structured light projectors to each project a distribution of discrete unconnected spots of light, wherein every spot projected from a specific structured light projector has the same shape, and the shape of the spots projected from at least one structured light projector is different from the shape of the spots projected from at least one other structured light projector.

For some applications, the method further includes:

driving at least one uniform light projector to project white light onto the intraoral three-dimensional surface; and driving at least one camera to capture two-dimensional color images of the intraoral three-dimensional surface using illumination from the uniform light projector.

For some applications, the method further includes, using the processor to run a surface reconstruction algorithm that combines at least one image captured using illumination from the structured light projectors with a plurality of images captured using illumination from the uniform light projector to generate a three-dimensional image of the intraoral three-dimensional surface.

For some applications, driving each one of the one or more structured light projectors includes driving a plurality of structured light projectors to simultaneously project respective distributions of discrete unconnected spots of light on the intraoral three-dimensional surface.

For some applications, driving each one of the one or more structured light projectors includes driving a plurality of structured light projectors to project respective discrete unconnected spots of light on the intraoral three-dimensional surface at different respective times.

For some applications, driving the plurality of structured light projectors to project respective discrete unconnected spots of light on the intraoral three-dimensional surface at different respective times includes driving the plurality of structured light projectors to project respective discrete unconnected spots of light on the intraoral three-dimensional surface in a predetermined order.

For some applications, driving the plurality of structured light projectors to project respective discrete unconnected spots of light on the intraoral three-dimensional surface at different respective times includes:

driving at least one structured light projector to project a distribution of discrete unconnected spots of light on the intraoral three-dimensional surface; and determining during a scan which of a plurality of structured light projectors to next drive to project a distribution of discrete unconnected spots of light.

For some applications:

driving each one of one or more structured light projectors includes driving exactly one structured light projector to project a distribution of discrete unconnected spots of light on an intraoral three-dimensional surface.

For some applications, driving each one of the one or more cameras includes driving the one or more cameras to each capture images at a frame rate of 30-200 frames per second.

For some applications, driving the one or more cameras includes driving the one or more cameras to each capture images at a frame rate of at least 75 frames per second.

For some applications, driving the one or more cameras includes driving the one or more cameras to each capture images at a frame rate of at least 100 frames per second.

For some applications, using the processor includes, based on data received from a temperature sensor indicative of the temperature of the structured light projectors and the cameras, selecting between a plurality of sets of stored calibration data corresponding to a plurality of respective temperatures of the structured light projectors and the cameras, each set of stored calibration data indicating for a respective temperature (a) the projector ray corresponding to each of the projected spots of light from each one of the one or more projectors, and (b) the camera ray corresponding to each pixel on the camera sensor of each one of the one or more cameras.

For some applications, using the processor includes, based on data received from a temperature sensor indicative of the temperature of the structured light projectors and the cameras, interpolating between the plurality of sets of stored calibration data in order to obtain calibration data for temperatures in between the respective temperatures corresponding to each set of calibration data.

For some applications:

driving each one of the one or more cameras includes driving each one of the one or more cameras to capture an image further including at least a region of a diffuse reflector having a plurality of regions such that:

(a) each projector has at least one region of the diffuse reflector in its field of illumination, (b) each camera has at least one region of the diffuse reflector in its field of view, and (c) a plurality of the regions of the diffuse reflector are in the field of view of one of the cameras and in the field of illumination of one of the projectors.

The processor may be used to (a) receive data from the cameras indicative of a position of the diffuse reflector with respect to the distribution of discrete unconnected spots of light, (b) compare the received data to a stored calibration position of the diffuse reflector, a discrepancy between (i) the received data indicative of the position of the diffuse reflector and (ii) the stored calibration position of the diffuse reflector indicating a shift of the projector rays and the cameras rays from their respective stored calibration values, and (c) run the correspondence algorithm based on the shift of the projector rays and the cameras rays from their respective stored calibration values.

In some embodiments, such as any of those described above or throughout the specification, high dynamic range 3D imaging may be provided using light field imaging in combination with structured illumination. Fringe patterns may be projected onto a scene and modulated by the scene depth. Then, a structured light field may be detected using light field recording devices. The structured light field contains information about ray direction and phase-encoded depth via which the scene depth can be estimated from different directions. The multidirectional depth estimation may be able to achieve high dynamic 3D imaging effectively.

Applications of the present invention may also include systems and methods related to a three-dimensional intraoral scanning device that includes one or more light field cameras, and one or more pattern projectors. For example, in some embodiments, an intraoral scanning apparatus is provided. The apparatus may include an elongate handheld wand including a probe at the distal end. The probe may have a proximal end and a distal end. During an intraoral scan the probe may be placed in the oral cavity of a subject. In accordance with some applications of the present invention, a structured light projector and a light field camera may be disposed in the proximal end of the probe, and a mirror is disposed in the distal end of the probe. The structured light projector and the light field camera may be positioned to face the mirror, and the mirror is positioned to (a) reflect light from the structured light projector directly onto an object being scanned and (b) reflect light from the object being scanned into the light field camera.

The structured light projector in the proximal end of the probe includes a light source. In some applications, the light source may have a field of illumination of at least 6 degrees and/or less than 30 degrees. The structured light projector may focus the light from the light source at a projector focal plane that is located at least 30 mm and/or less than 140 mm from the light source. The structured light projector may further include a pattern generator, disposed in the optical path between the light source and the projector focal plane, that generates a structured light pattern at the projector focal plane when the light source is activated to transmit light through the pattern generator.

In some applications, the light field camera in the proximal end of the probe may have a field of view of at least 6 degrees and/or less than 30 degrees. The light field camera may focus at a camera focal plane that is located at least 30 mm and/or less than 140 mm from the light field camera. The light field camera may further include a light field camera sensor that includes (i) an image sensor comprising an array of sensor pixels, and (ii) an array of micro-lenses disposed in front of the image sensor, such that each micro-lens is disposed over a sub-array of the sensor pixels. An objective lens disposed in front of the light field camera sensor forms an image of the object being scanned onto the light field camera sensor.

In accordance with some applications of the present invention, one or more structured light projectors and one or more light field cameras are disposed in the distal end of the probe. The structured light projectors and the light field cameras are positioned such that each structured light projector directly faces an object outside of the wand placed in its field of illumination, and each camera directly faces an object outside of the wand placed in its field of view. At least 40% of the projected structured light pattern from each projector is in the field of view of at least one of the cameras.

The one or more structured light projectors in the distal end of the probe each include a light source. In some applications, the respective structured light projectors may each have a field of illumination of at least 60 degrees and/or less than 120 degrees. Each structured light projector may focus the light from the light source at a projector focal plane that is located at least 30 mm and/or less than 140 mm from the light source. Each structured light projector may further include a pattern generator disposed in the optical path between the light source and the projector focal plane that generates a structured light pattern at the projector focal plane when the light source is activated to transmit light through the pattern generator.

In some applications, the one or more light field cameras in the distal end of the probe may each have a field of view of at least 60 degrees and/or less than 120 degrees. Each light field camera may focus at a camera focal plane that is located at least 3 mm and/or less than 40 mm from the light field camera. Each light field camera may further include a light field camera sensor including (i) an image sensor comprising an array of sensor pixels, and (ii) an array of micro-lenses disposed in front of the image sensor such that each micro-lens is disposed over a sub-array of the sensor pixels. An objective lens disposed in front of each light field camera sensor forms an image of the object being scanned onto the light field camera sensor.

There is therefore provided, in accordance with some applications of the present invention, apparatus for intraoral scanning, the apparatus including:

(A) an elongate handheld wand including a probe at a distal end of the handheld wand, the probe having a proximal end and a distal end;

(B) a structured light projector disposed in the proximal end of the probe, the structured light projector:
  (a) having a field of illumination of 6-30 degrees,
  (b) including a light source, and
  (c) configured to focus light from the light source at a projector focal plane that is located between 30 mm and 140 mm from the light source, and
  (d) including a pattern generator disposed in the optical path between the light source and the projector focal plane, and configured to generate a structured light pattern at the projector focal plane when the light source is activated to transmit light through the pattern generator;

(C) a light field camera disposed in the proximal end of the probe, the light field camera:
  (a) having a field of view of 6-30 degrees,
  (b) configured to focus at a camera focal plane that is located between 30 mm and 140 mm from the light field camera,
  (c) including a light field camera sensor, the light field camera sensor including (i) an image sensor including an array of sensor pixels, and (ii) an array of micro-lenses disposed in front of the image sensor such that each micro-lens is disposed over a sub-array of the sensor pixels, and
  (d) including an objective lens disposed in front of the light field camera sensor and configured to form an image of an object being scanned onto the light field camera sensor; and (D) a mirror disposed in the distal end of the handheld wand,
  the structured light projector and the light field camera positioned to face the mirror, and the mirror positioned to (a) reflect light from the structured light projector directly onto the object being scanned and (b) reflect light from the object being scanned into the light field camera.

For some applications, the light source includes a light emitting diode (LED), and the pattern generator includes a mask.

For some applications, the light source includes a laser diode.

For some applications, the pattern generator includes a diffractive optical element (DOE) configured to generate the structured light pattern as a distribution of discrete unconnected spots of light.

For some applications, the pattern generator includes a refractive micro-lens array.

For some applications, a height of the probe is 14-17 mm and a width of the probe is 18-22 mm, the height and width defining a plane that is perpendicular to a longitudinal axis of the wand, light entering the probe through a lower surface of the probe, and the height of the probe being measured from the lower surface of the probe to an upper surface of the probe opposite the lower surface.

For some applications, the apparatus is configured for use with an output device, the apparatus further including:
  control circuitry configured to:
    (a) drive the structured light projector to project the structured light pattern onto an object outside the wand,
    (b) drive the light field camera to capture a light field resulting from the structured light pattern reflecting off the object, the light field including (i) the intensity of the structured light pattern reflecting off of the object, and (ii) the direction of the light rays; and at least one computer processor configured to, based on the captured light field, reconstruct a 3-dimensional image of the surface of the object being scanned, and output the image to the output device.

For some applications:

(a) the object outside the wand is a tooth inside a subject's mouth, (b) the control circuitry is configured to drive the light field camera to capture a light field resulting from the structured light pattern reflecting off the tooth without the presence of a powder on the tooth, and (c) the computer processor is configured to reconstruct a 3-dimensional image of the tooth based on the light field that was captured without the presence of a powder on the tooth, and to output the image to the output device.

For some applications, each of the sub-arrays of sensor pixels in a central region of the image sensor includes 10-40% fewer pixels than each of the sub-arrays of sensor pixels in a peripheral region of the image sensor, the central region of the image sensor including at least 50% of the total number of sensor pixels.

For some applications, (a) a depth at which each micro-lens disposed over a sub-array of sensor pixels in the peripheral region of the image sensor is configured to focus is 1.1-1.4 times larger than (b) a depth at which each micro-lens disposed over a sub-array of sensor pixels in the central region of the image sensor is configured to focus.

There is further provided, in accordance with some applications of the present invention, apparatus including:

(A) an elongate handheld wand including a probe at a distal end of the handheld wand, the probe having a proximal end and a distal end;

(B) one or more structured light projectors disposed in the distal end of the probe, each structured light projector:

(a) having a field of illumination of 60-120 degrees, (b) including a light source, and (c) configured to focus light from the light source at a projector focal plane that is located between 3 mm and 40 mm from the light source, and (d) including a pattern generator disposed in the optical path between the light source and the projector focal plane, and configured to generate a structured light pattern at the projector focal plane when the light source is activated to transmit light through the pattern generator; and (C) one or more light field cameras disposed in the distal end of the probe, each light field camera:

(a) having a field of view of 60-120 degrees, (b) configured to focus at a camera focal plane that is located between 3 mm and 40 mm from the light field camera, (c) including a light field camera sensor, the light field camera sensor including (i) an image sensor including an array of sensor pixels, and (ii) an array of micro-lenses disposed in front of the image sensor such that each micro-lens is disposed over a sub-array of the sensor pixels, and (d) including an objective lens disposed in front of the light field camera sensor and configured to form an image of an object being scanned onto the light field camera sensor, the structured light projectors and the light field cameras positioned such that (a) each structured light projector directly faces an object outside of the wand placed in its field of illumination, (b) each camera directly faces an object outside of the wand placed in its field of view, and (c) at least 40% of the structured light pattern from each projector is in the field of view of at least one of the cameras.

For some applications, a height of the probe is 10-14 mm and a width of the probe is 18-22 mm, the height and width defining a plane that is perpendicular to a longitudinal axis of the wand, light entering the probe through a lower surface of the probe, and the height of the probe being measured from the lower surface of the probe to an upper surface of the probe opposite the lower surface.

For some applications, the one or more structured light projectors is exactly one structured light projector, and the one or more structured light field cameras is exactly one light field camera.

For some applications, the one or more structured light projectors are a plurality of structured light projectors, and the one or more light field cameras are a plurality of light field cameras.

For some applications, the apparatus is configured for use with an output device, the apparatus further including:

control circuitry configured to:

(a) drive each of the one or more structured light projectors to project a structured light pattern onto an object outside the wand, (b) drive the one or more light field cameras to capture a light field resulting from the structured light patterns reflecting off the object, the light field including (i) the intensity of the structured light pattern reflecting off of the object, (ii) the direction of the light rays; and at least one computer processor configured to, based on the captured light field, reconstruct a 3-dimensional image of the surface of the object being scanned, and output the image to the output device.

For some applications:

at least one of the one or more structured light projectors is a monochrome structured light projector configured to project a monochrome structured light pattern onto the object being scanned, at least one of the one or more light field cameras is a monochrome light field camera configured to capture a light field resulting from the monochrome structured light pattern reflecting off the object being scanned, and the apparatus further includes (a) a light source configured to transmit white light onto the object being scanned, and (b) a camera configured to capture a 2-dimensional color image of the object being scanned.

For some applications, the monochrome structured light projector is configured to project the structured light pattern at a wavelength of 420-470 nm.

There is further provided, in accordance with some applications of the present invention, apparatus including:

(A) an elongate handheld wand including a probe at a distal end of the handheld wand, the probe having a proximal end and a distal end;

(B) a structured light projector disposed in the proximal end of the probe, the structured light projector:

(a) having a field of illumination, (b) including a light source, and (c) configured to focus light from the light source at a projector focal plane, and (d) including a pattern generator disposed in the optical path between the light source and the projector focal plane, and configured to generate a structured light pattern at the projector focal plane when the light source is activated to transmit light through the pattern generator;

(C) a light field camera disposed in the proximal end of the probe, the light field camera:
(a) having a field of view,
(b) configured to focus at a camera focal plane,
(c) including a light field camera sensor, the light field camera sensor including (i) an image sensor including an array of sensor pixels, and (ii) an array of micro-lenses disposed in front of the image sensor such that each micro-lens is disposed over a sub-array of the sensor pixels, and
(d) including an objective lens disposed in front of the light field camera sensor and configured to form an image of an object being scanned onto the light field camera sensor; and
(D) a mirror disposed in the distal end of the handheld wand,
the structured light projector and the light field camera positioned to face the mirror, and the mirror positioned to (a) reflect light from the structured light projector directly onto the object being scanned and (b) reflect light from the object being scanned into the light field camera.

There is further provided, in accordance with some applications of the present invention, apparatus including:
(A) an elongate handheld wand including a probe at a distal end of the handheld wand, the probe having a proximal end and a distal end;
(B) one or more structured light projectors disposed in the distal end of the probe, each structured light projector:
(a) having a field of illumination,
(b) including a light source, and
(c) configured to focus light from the light source at a projector focal plane, and
(d) including a pattern generator disposed in the optical path between the light source and the projector focal plane, and configured to generate a structured light pattern at the projector focal plane when the light source is activated to transmit light through the pattern generator; and
(C) one or more light field cameras disposed in the distal end of the probe, each light field camera:
(a) having a field of view,
(b) configured to focus at a camera focal plane,
(c) including a light field camera sensor, the light field camera sensor including (i) an image sensor including an array of sensor pixels, and (ii) an array of micro-lenses disposed in front of the image sensor such that each micro-lens is disposed over a sub-array of the sensor pixels, and
(d) including an objective lens disposed in front of the light field camera sensor and configured to form an image of an object being scanned onto the light field camera sensor,
the structured light projectors and the light field cameras positioned such that (a) each structured light projector directly faces an object outside of the wand placed in its field of illumination, (b) each camera directly faces an object outside of the wand placed in its field of view, and (c) at least 40% of the structured light pattern from each projector is in the field of view of at least one of the cameras.

The present invention will be more fully understood from the following detailed description of applications thereof, taken together with the drawings, in which:

BRIEF DESCRIPTION OF THE DRAWINGS

FIG. 4 is a schematic illustration of a structured light projector projecting a distribution of discrete unconnected spots of light onto a plurality of object focal planes, in accordance with some applications of the present invention;

FIGS. 19A-B are schematic illustrations of a structured light projector and a cross-section of a beam of light transmitted by a laser diode, with a pattern generating optical element shown disposed in the light path of the beam, in accordance with some applications of the present invention;

DETAILED DESCRIPTION

Figure 1:
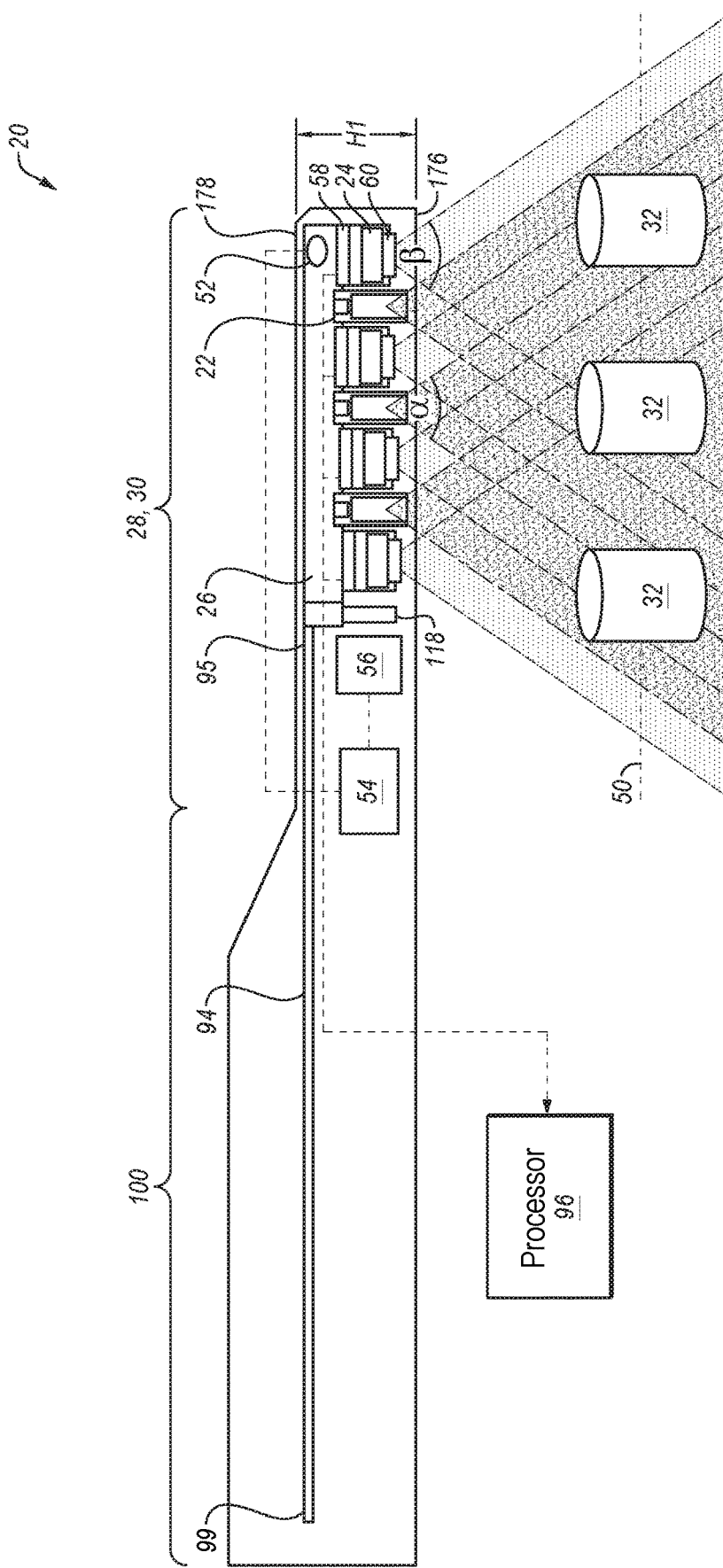
FIG. 1 is a schematic illustration of a handheld wand with a plurality of structured light projectors and cameras disposed within a probe at a distal end of the handheld wand, in accordance with some applications of the present invention.

Reference is now made to FIG. 1, which is a schematic illustration of an elongate handheld wand 20 for intraoral scanning, in accordance with some applications of the present invention. A plurality of structured light projectors 22 and a plurality of cameras 24 are coupled to a rigid structure 26 disposed within a probe 28 at a distal end 30 of the handheld wand. In some applications, during an intraoral scan, probe 28 enters the oral cavity of a subject.

For some applications, structured light projectors 22 are positioned within probe 28 such that each structured light projector 22 faces an object 32 outside of handheld wand 20 that is placed in its field of illumination, as opposed to positioning the structured light projectors in a proximal end of the handheld wand and illuminating the object by reflection of light off a mirror and subsequently onto the object. Similarly, for some applications, cameras 24 are positioned within probe 28 such that each camera 24 faces an object 32 outside of handheld wand 20 that is placed in its field of view, as opposed to positioning the cameras in a proximal end of the handheld wand and viewing the object by reflection of light off a mirror and into the camera. This positioning of the projectors and the cameras within probe 28 enables the scanner to have an overall large field of view while maintaining a low profile probe.

In some applications, a height H1 of probe 28 is less than 15 mm, height H1 of probe 28 being measured from a lower surface 176 (sensing surface), through which reflected light from object 32 being scanned enters probe 28, to an upper surface 178 opposite lower surface 176. In some applications, the height H1 is between 10-15 mm.

In some applications, cameras 24 each have a large field of view β (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In experiments performed by the inventors, field of view β (beta) for each camera being between 80 and 90 degrees was found to be particularly useful because it provided a good balance among pixel size, field of view and camera overlap, optical quality, and cost. Cameras 24 may include a camera sensor 58 and objective optics 60 including one or more lenses. To enable close focus imaging cameras 24 may focus at an object focal plane 50 that is located between 1 mm and 30 mm, e.g., between 4 mm and 24 mm, e.g., between 5 mm and 11 mm, e.g., 9 mm-10 mm, from the lens that is farthest from the camera sensor. In experiments performed by the inventors, object focal plane 50 being located between 5 mm and 11 mm from the lens that is farthest from the camera sensor was found to be particularly useful because it was easy to scan the teeth at this distance, and because most of the tooth surface was in good focus. In some applications, cameras 24 may capture images at a frame rate of at least 30 frames per second, e.g., at a frame of at least 75 frames per second, e.g., at least 100 frames per second. In some applications, the frame rate may be less than 200 frames per second.

As described hereinabove, a large field of view achieved by combining the respective fields of view of all the cameras may improve accuracy due to reduced amount of image stitching errors, especially in edentulous regions, where the gum surface is smooth and there may be fewer clear high resolution 3-D features. Having a larger field of view enables large smooth features, such as the overall curve of the tooth, to appear in each image frame, which improves the accuracy of stitching respective surfaces obtained from multiple such image frames.

Similarly, structured light projectors 22 may each have a large field of illumination α (alpha) of at least 45 degrees, e.g., at least 70 degrees. In some applications, field of illumination α (alpha) may be less than 120 degrees, e.g., than 100 degrees. Further features of structured light projectors 22 are described hereinbelow.

For some applications, in order to improve image capture, each camera 24 has a plurality of discrete preset focus positions, in each focus position the camera focusing at a respective object focal plane 50. Each of cameras 24 may include an autofocus actuator that selects a focus position from the discrete preset focus positions in order to improve a given image capture. Additionally or alternatively, each camera 24 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the camera sensor.

In some applications, structured light projectors 22 and cameras 24 are coupled to rigid structure 26 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 50 that is located at least 4 mm from the lens that is farthest from the camera sensor. Due to different possible configurations of the projectors and cameras, some of the projected pattern may never be seen in the field of view of any of the cameras, and some of the projected pattern may be blocked from view by object 32 as the scanner is moved around during a scan.

Rigid structure 26 may be a non-flexible structure to which structured light projectors 22 and cameras 24 are coupled so as to provide structural stability to the optics within probe 28. Coupling all the projectors and all the cameras to a common rigid structure helps maintain geometric integrity of the optics of each structured light projector 22 and each camera 24 under varying ambient conditions, e.g., under mechanical stress as may be induced by the subject's mouth. Additionally, rigid structure 26 helps maintain stable structural integrity and positioning of structured light projectors 22 and cameras 24 with respect to each other. As further described hereinbelow, controlling the temperature of rigid structure 26 may help enable maintaining geometrical integrity of the optics through a large range of ambient temperatures as probe 28 enters and exits a subject's oral cavity or as the subject breathes during a scan.

Figure 2B:
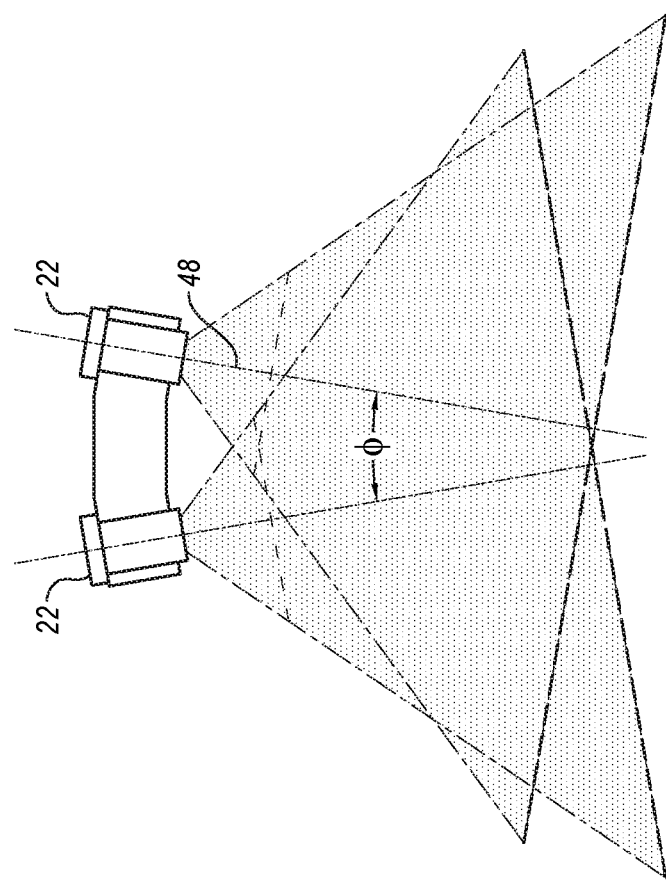
FIGS. 2A-B are schematic illustrations of positioning configurations for the cameras and structured light projectors respectively, in accordance with some applications of the present invention.
Figure 2A:
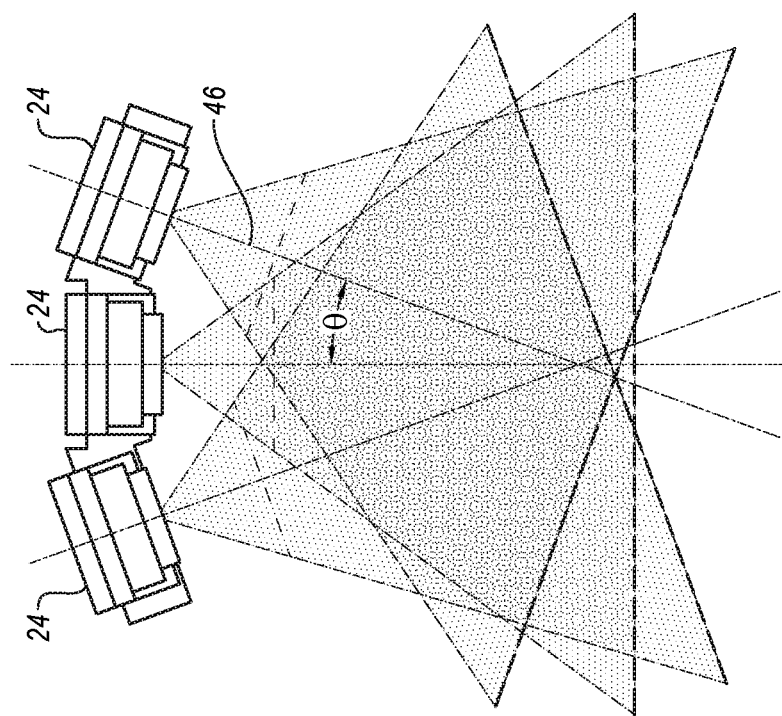

Reference is now made to FIGS. 2A-B, which are schematic illustration of a positioning configuration for cameras 24 and structured light projectors 22 respectively, in accordance with some applications of the present invention. For some applications, in order to improve the overall field of view and field of illumination of the intraoral scanner, cameras 24 and structured light projectors 22 are positioned such that they do not all face the same direction. For some applications, such as is shown in FIG. 2A, a plurality of cameras 24 are coupled to rigid structure 26 such that an angle θ (theta) between two respective optical axes 46 of at least two cameras 24 is 90 degrees or less, e.g., 35 degrees or less. Similarly, for some applications, such as is shown in FIG. 2B, a plurality of structured light projectors 22 are coupled to rigid structure 26 such that an angle φ (phi) between two respective optical axes 48 of at least two structured light projectors 22 is 90 degrees or less, e.g., 35 degrees or less.

Figure 2C:
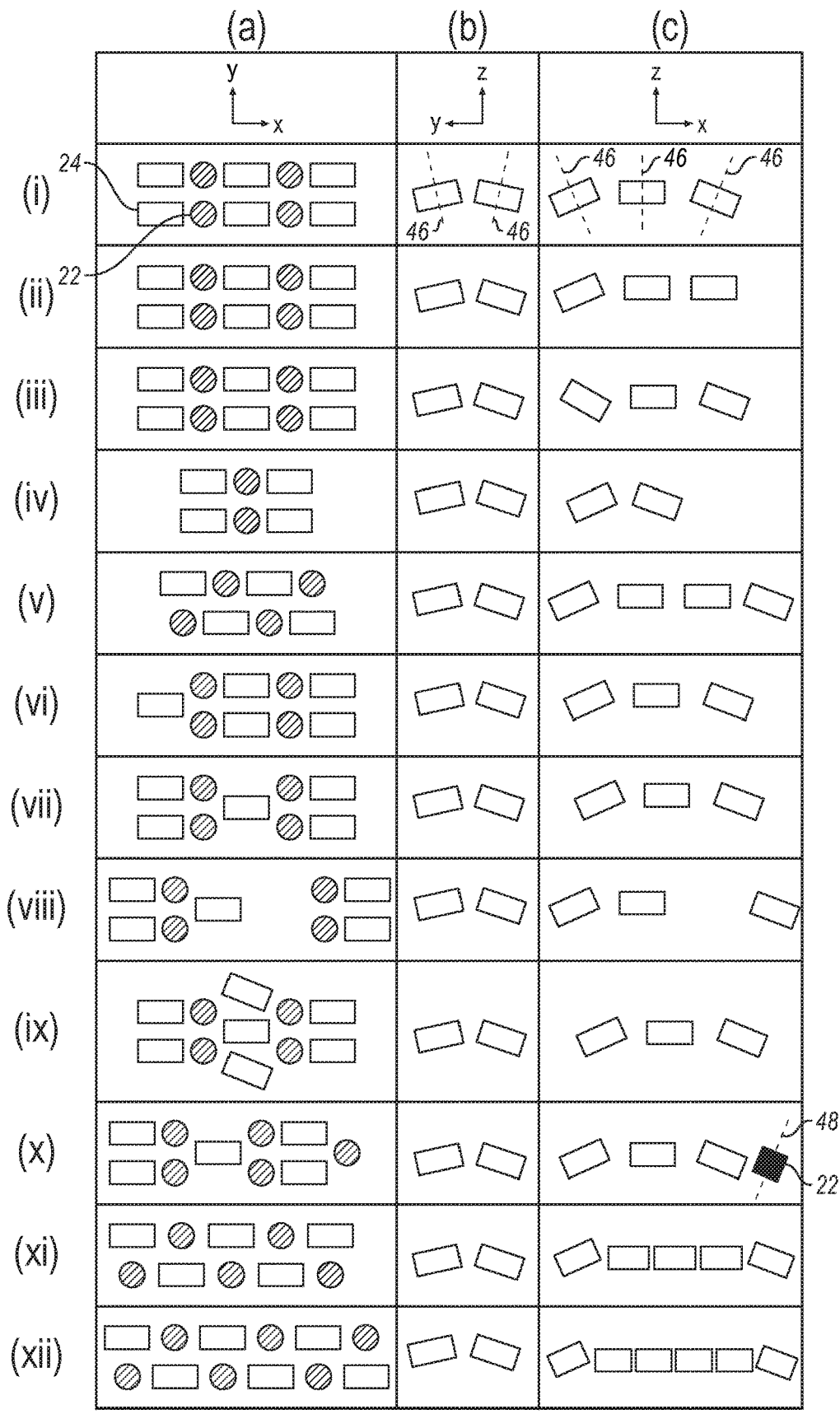
FIG. 2C is a chart depicting a plurality of different configurations for the position of the structured light projectors and the cameras in the probe, in accordance with some applications of the present invention.

Reference is now made to FIG. 2C, which is a chart depicting a plurality of different configurations for the position of structured light projectors 22 and cameras 24 in probe 28, in accordance with some applications of the present invention. Structured light projectors 22 are represented in FIG. 2C by circles and cameras 24 are represented in FIG. 2C by rectangles. It is noted that rectangles are used to represent the cameras, since typically, each camera sensor 58 and the field of view β (beta) of each camera 24 have aspect ratios of 1:2. Column (a) of FIG. 2C shows a bird's eye view of the various configurations of structured light projectors 22 and cameras 24. The x-axis as labeled in the first row of column (a) corresponds to a central longitudinal axis of probe 28. Column (b) shows a side view of cameras 24 from the various configurations as viewed from a line of sight that is coaxial with the central longitudinal axis of probe 28. Similarly to as shown in FIG. 2A, column (b) of FIG. 2C shows cameras 24 positioned so as to have optical axes 46 at an angle of 90 degrees or less, e.g., 35 degrees or less, with respect to each other. Column (c) shows a side view of cameras 24 of the various configurations as viewed from a line of sight that is perpendicular to the central longitudinal axis of probe 28.

Typically, the distal-most (toward the positive x-direction in FIG. 2C) and proximal-most (toward the negative x-direction in FIG. 2C) cameras 24 are positioned such that their optical axes 46 are slightly turned inwards, e.g., at an angle of 90 degrees or less, e.g., 35 degrees or less, with respect to the next closest camera 24. The camera(s) 24 that are more centrally positioned, i.e., not the distal-most camera 24 nor proximal-most camera 24, are positioned so as to face directly out of the probe, their optical axes 46 being substantially perpendicular to the central longitudinal axis of probe 28. It is noted that in row (x) a projector 22 is positioned in the distal-most position of probe 28, and as such the optical axis 48 of that projector 22 points inwards, allowing a larger number of spots 33 projected from that particular projector 22 to be seen by more cameras 24.

Typically, the number of structured light projectors 22 in probe 28 may range from two, e.g., as shown in row (iv) of FIG. 2C, to six, e.g., as shown in row (xii). Typically, the number of cameras 24 in probe 28 may range from four, e.g., as shown in rows (iv) and (v), to seven, e.g., as shown in row (ix). It is noted that the various configurations shown in FIG. 2C are by way of example and not limitation, and that the scope of the present invention includes additional configurations not shown. For example, the scope of the present invention includes more than five projectors 22 positioned in probe 28 and more than seven cameras positioned in probe 28.

In an example application, an apparatus for intraoral scanning (e.g., an intraoral scanner) includes an elongate handheld wand comprising a probe at a distal end of the elongate handheld wand, at least two light projectors disposed within the probe, and at least four cameras disposed within the probe. Each light projector may include at least one light source configured to generate light when activated, and a pattern generating optical element that is configured to generate a pattern of light when the light is transmitted through the pattern generating optical element. Each of the at least four cameras may include a camera sensor and one or more lenses, wherein each of the at least four cameras is configured to capture a plurality of images that depict at least a portion of the projected pattern of light on an intraoral surface. A majority of the at least two light projectors and the at least four cameras may be arranged in at least two rows that are each approximately parallel to a longitudinal axis of the probe, the at least two rows comprising at least a first row and a second row.

In a further application, a distal-most camera along the longitudinal axis and a proximal-most camera along the longitudinal axis of the at least four cameras are positioned such that their optical axes are at an angle of 90 degrees or less with respect to each other from a line of sight that is perpendicular to the longitudinal axis. Cameras in the first row and cameras in the second row may be positioned such that optical axes of the cameras in the first row are at an angle of 90 degrees or less with respect to optical axes of the cameras in the second row from a line of sight that is coaxial with the longitudinal axis of the probe. A remainder of the at least four cameras other than the distal-most camera and the proximal-most camera have optical axes that are substantially parallel to the longitudinal axis of the probe. Each of the at least two rows may include an alternating sequence of light projectors and cameras.

In a further application, the at least four cameras comprise at least five cameras, the at least two light projectors comprise at least five light projectors, a proximal-most component in the first row is a light projector, and a proximal-most component in the second row is a camera.

In a further application, the distal-most camera along the longitudinal axis and the proximal-most camera along the longitudinal axis are positioned such that their optical axes are at an angle of 35 degrees or less with respect to each other from the line of sight that is perpendicular to the longitudinal axis. The cameras in the first row and the cameras in the second row may be positioned such that the optical axes of the cameras in the first row are at an angle of 35 degrees or less with respect to the optical axes of the cameras in the second row from the line of sight that is coaxial with the longitudinal axis of the probe.

In a further application, the at least four cameras may have a combined field of view of 25-45 mm along the longitudinal axis and a field of view of 20-40 mm along a z-axis corresponding to distance from the probe.

Figure 3:
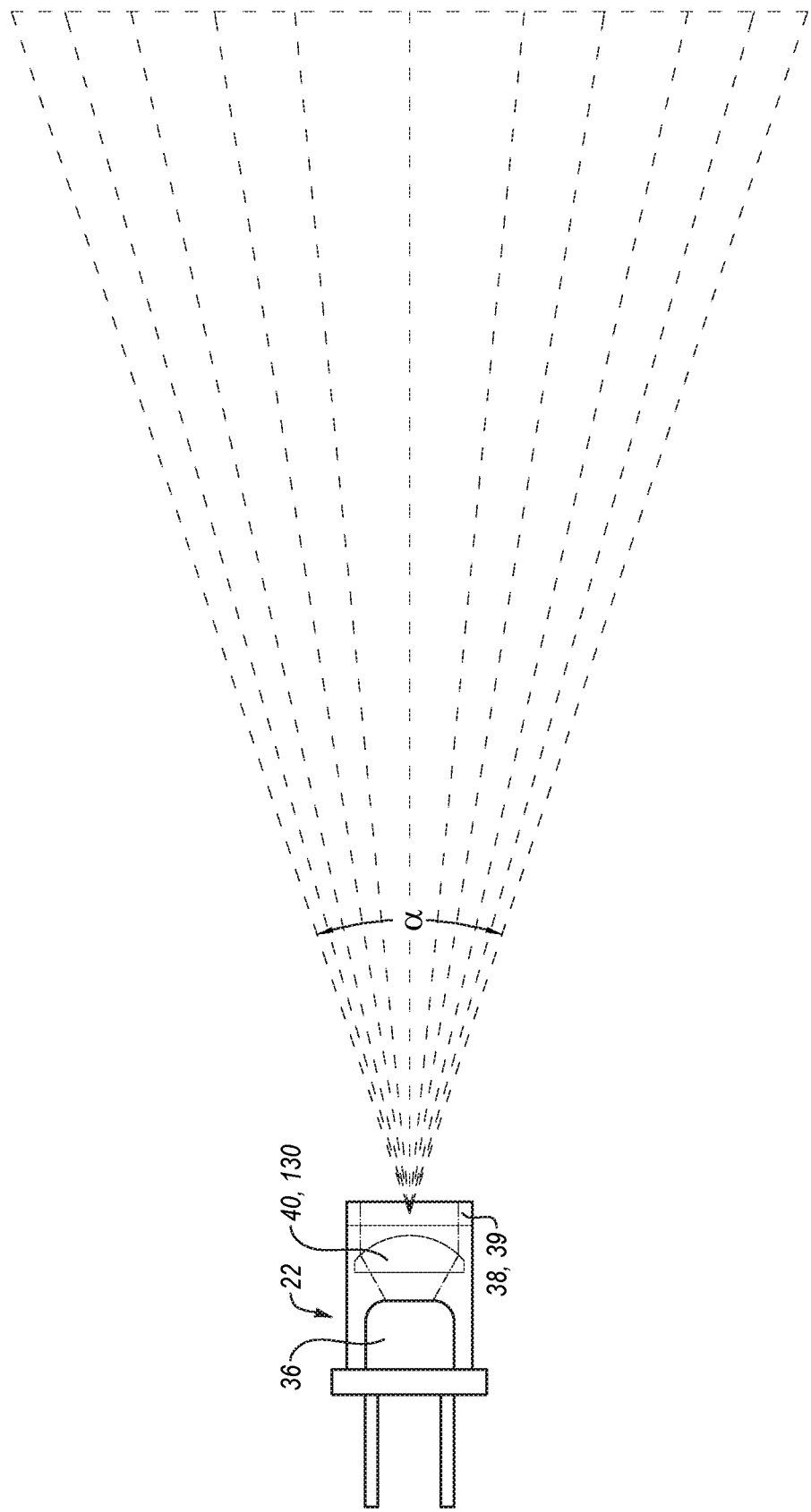
FIG. 3 is a schematic illustration of a structured light projector, in accordance with some applications of the present invention.

Reference is now made to FIG. 3, which is a schematic illustration of a structured light projector 22, in accordance with some applications of the present invention. In some applications, structured light projectors 22 include a laser diode 36, a beam shaping optical element 40, and a pattern generating optical element 38 that generates a distribution 34 of discrete unconnected spots of light (further discussed hereinbelow with reference to FIG. 4). In some applications, the structured light projectors 22 may be configured to generate a distribution 34 of discrete unconnected spots of light at all planes located between mm and 30 mm, e.g., between 4 mm and 24 mm, from pattern generating optical element 38 when laser diode 36 transmits light through pattern generating optical element 38. For some applications, distribution 34 of discrete unconnected spots of light is in focus at one plane located between 1 mm and 30 mm, e.g., between 4 mm and 24 mm, yet all other planes located between 1 mm and 30 mm, e.g., between 4 mm and 24 mm, still contain discrete unconnected spots of light. While described above as using laser diodes, it should be understood that this is an exemplary and non-limiting application. Other light sources may be used in other applications. Further, while described as projecting a pattern of discrete unconnected spots of light, it should be understood that this is an exemplary and non-limiting application. Other patterns or arrays of lights may be used in other applications, including but not limited to, lines, grids, checkerboards, and other arrays.

Pattern generating optical element 38 may be configured to have a light throughput efficiency (i.e., the fraction of light that goes into the pattern out of the total light falling on pattern generating optical element 38) of at least 80%, e.g., at least 90%.

For some applications, respective laser diodes 36 of respective structured light projectors 22 transmit light at different wavelengths, i.e., respective laser diodes 36 of at least two structured light projectors 22 transmit light at two distinct wavelengths, respectively. For some applications, respective laser diodes 36 of at least three structured light projectors 22 transmit light at three distinct wavelengths respectively. For example, red, blue, and green laser diodes may be used. For some applications, respective laser diodes 36 of at least two structured light projectors 22 transmit light at two distinct wavelengths respectively. For example, in some applications there are six structured light projectors 22 disposed within probe 28, three of which contain blue laser diodes and three of which contain green laser diodes.

Reference is now made to FIG. 4, which is a schematic illustration of a structured light projector 22 projecting a distribution of discrete unconnected spots of light onto a plurality of object focal planes, in accordance with some applications of the present invention. Object 32 being scanned may be one or more teeth or other intraoral object/tissue inside a subject's mouth. The somewhat translucent and glossy properties of teeth may affect the contrast of the structured light pattern being projected. For example, (a) some of the light hitting the teeth may scatter to other regions within the intraoral scene, causing an amount of stray light, and (b) some of the light may penetrate the tooth and subsequently come out of the tooth at any other point. Thus, in order to improve image capture of an intraoral scene under structured light illumination, without using contrast enhancement means such as coating the teeth with an opaque powder, the inventors have realized that a sparse distribution 34 of discrete unconnected spots of light may provide an improved balance between reducing the amount of projected light while maintaining a useful amount of information. The sparseness of distribution 34 may be characterized by a ratio of:

(a) illuminated area on an orthogonal plane 44 in field of illumination $\alpha$ (alpha), i.e., the sum of the area of all projected spots 33 on the orthogonal plane 44 in field of illumination $\alpha$ (alpha), to (b) non-illuminated area on orthogonal plane 44 in field of illumination $\alpha$ (alpha). In some applications, sparseness ratio may be at least 1:150 and/or less than 1:16 (e.g., at least 1:64 and/or less than 1:36).

In some applications, each structured light projector 22 projects at least 400 discrete unconnected spots 33 onto an intraoral three-dimensional surface during a scan. In some applications, each structured light projector 22 projects less than 3000 discrete unconnected spots 33 onto an intraoral surface during a scan. In order to reconstruct the three-dimensional surface from projected sparse distribution 34, correspondence between respective projected spots 33 and the spots detected by cameras 24 must be determined, as further described hereinbelow with reference to FIGS. 7-19.

For some applications, pattern generating optical element 38 is a diffractive optical element (DOE) 39 (FIG. 3) that generates distribution 34 of discrete unconnected spots 33 of light when laser diode 36 transmits light through DOE 39 onto object 32. As used herein throughout the present application, including in the claims, a spot of light is defined as a small area of light having any shape. For some applications, respective DOE's 39 of different structured light projectors 22 generate spots having different respective shapes, i.e., every spot 33 generated by a specific DOE 39 has the same shape, and the shape of spots 33 generated by at least one DOE 39 is different from the shape of spots 33 generated by at least one other DOE 39. By way of example, some of DOE's 39 may generate circular spots 33 (such as is shown in FIG. 4), some of DOE's 39 may generate square spots, and some of the DOE's 39 may generate elliptical spots. Optionally, some DOE's 39 may generate line patterns, connected or unconnected.

Figure 5A:
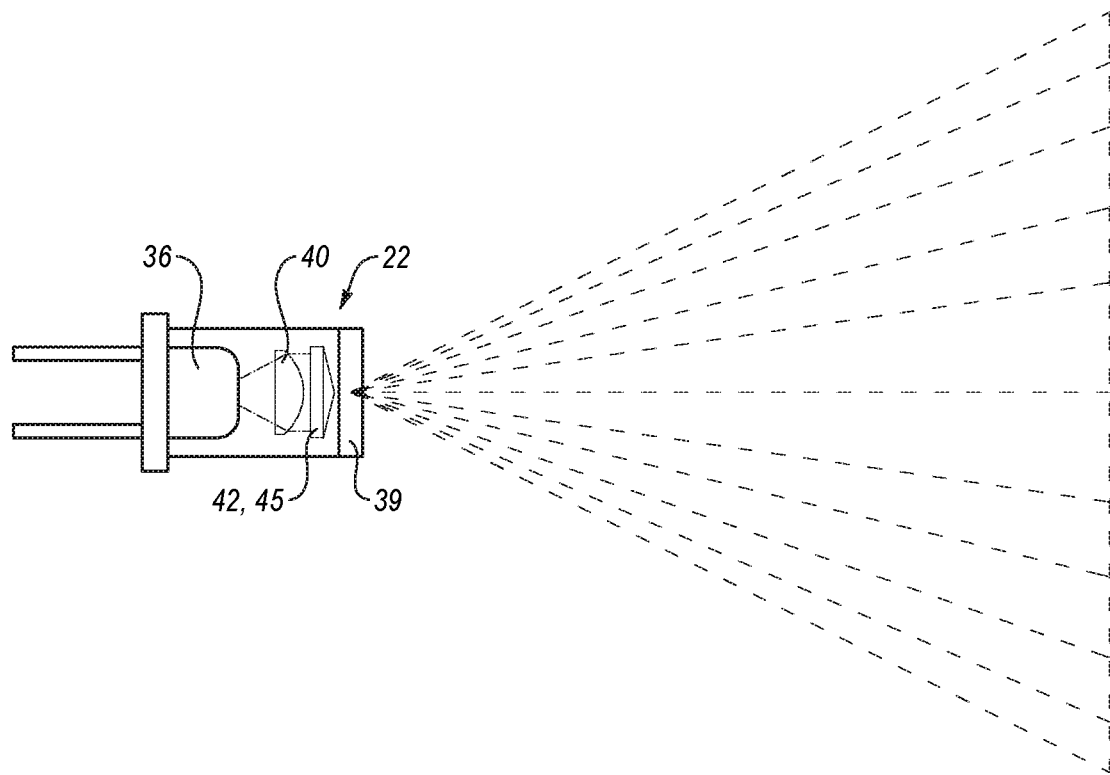
FIGS. 5A-B are schematic illustrations of a structured light projector, including a beam shaping optical element and an additional optical element disposed between the beam shaping optical element and a pattern generating optical element, in accordance with some applications of the present invention.
Figure 5B:
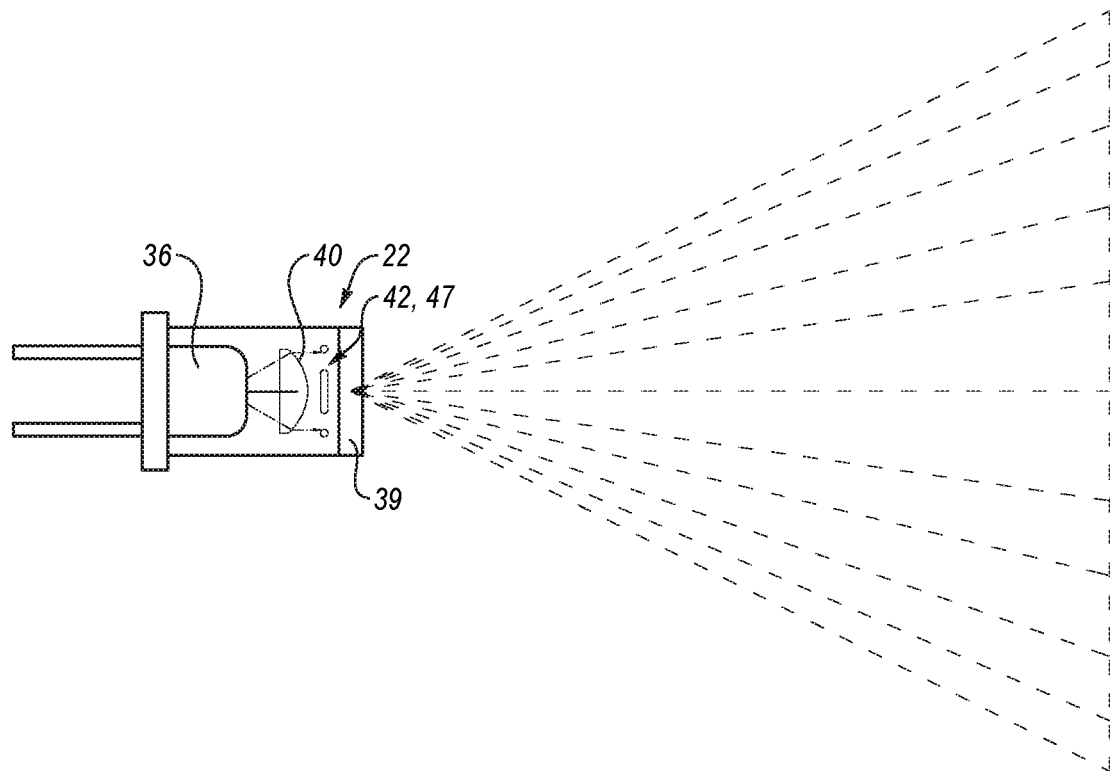

Reference is now made to FIGS. 5A-B, which are schematic illustrations of a structured light projector 22, including beam shaping optical element 40 and an additional optical element disposed between beam shaping optical element 40 and pattern generating optical element 38, e.g., DOE 39, in accordance with some applications of the present invention. Optionally, beam shaping optical element 40 is a collimating lens 130. Collimating lens 130 may be configured to have a focal length of less than 2 mm. Optionally, the focal length may be at least at least 1.2 mm. For some applications, an additional optical element 42, disposed between beam shaping optical element 40 and pattern generating optical element 38, e.g., DOE 39, generates a Bessel beam when laser diode 36 transmits light through optical element 42. In some applications, the Bessel beam is transmitted through DOE 39 such that all discrete unconnected spots 33 of light maintain a small diameter (e.g., less than 0.06 mm, e.g., less than 0.04 mm, e.g., less than 0.02 mm), through a range of orthogonal planes 44 (e.g., each orthogonal plane located between 1 mm and 30 mm from DOE 39, e.g., between 4 mm and 24 mm from DOE 39, etc.). The diameter of spots 33 is defined, in the context of the present patent application, by the full width at half maximum (FWHM) of the intensity of the spot.

Notwithstanding the above description of all spots being smaller than 0.06 mm, some spots that have a diameter near the upper end of these ranges (e.g., only somewhat smaller than 0.06 mm, or 0.02 mm) that are also near the edge of the field of illumination of a projector 22 may be elongated when they intersect a geometric plane that is orthogonal to DOE 39. For such cases, it is useful to measure their diameter as they intersect the inner surface of a geometric sphere that is centered at DOE 39 and that has a radius between 1 mm and 30 mm, corresponding to the distance of the respective orthogonal plane that is located between 1 mm and 30 mm from DOE 39. As used throughout the present application, including in the claims, the word "geometric" is taken to relate to a theoretical geometric construct (such as a plane or a sphere), and is not part of any physical apparatus.

For some applications, when the Bessel beam is transmitted through DOE 39, spots 33 having diameters larger than 0.06 mm are generated in addition to the spots having diameters less than 0.06 mm.

For some applications, optical element 42 is an axicon lens 45, such as is shown in FIG. 5A and further described hereinbelow with reference to FIGS. 23A-B. Alternatively, optical element 42 may be an annular aperture ring 47, such as is shown in FIG. 5B. Maintaining a small diameter of the spots improves 3-D resolution and precision throughout the depth of focus. Without optical element 42, e.g., axicon lens 45 or annular aperture ring 47, the spot of spots 33 size may vary, e.g., becomes bigger, as you move farther away from a best focus plane due to diffraction and defocus.

Figure 6A:
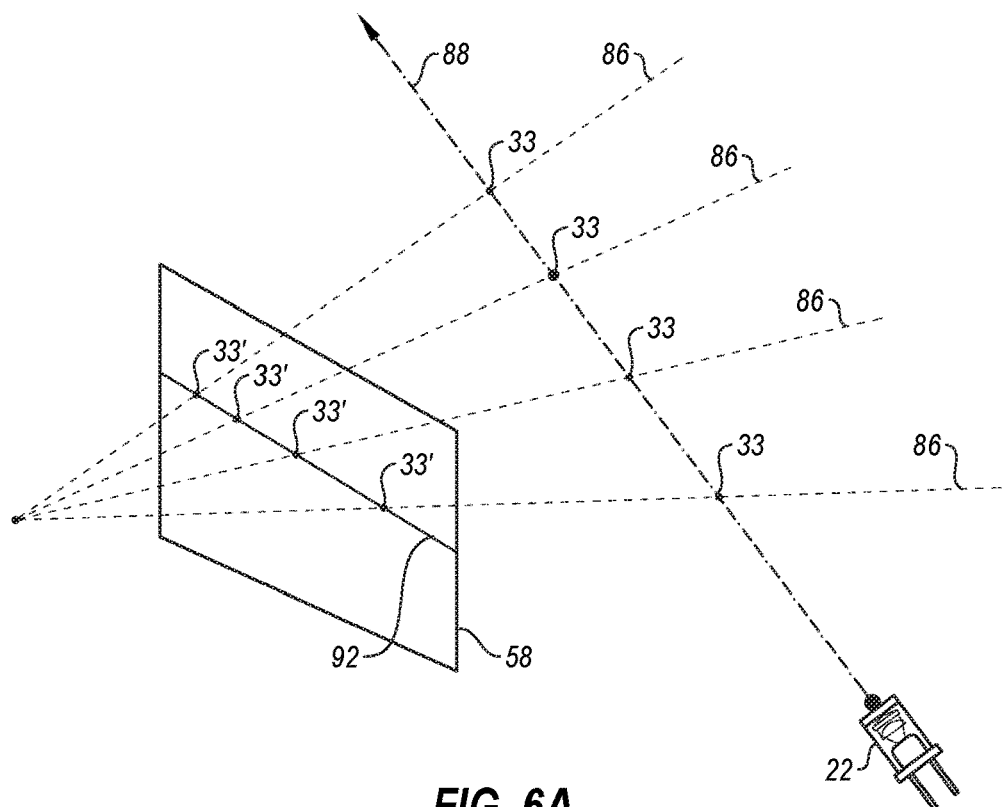
FIGS. 6A-B are schematic illustrations of a structured light projector projecting discrete unconnected spots and a camera sensor detecting spots, in accordance with some applications of the present invention.
Figure 6B:
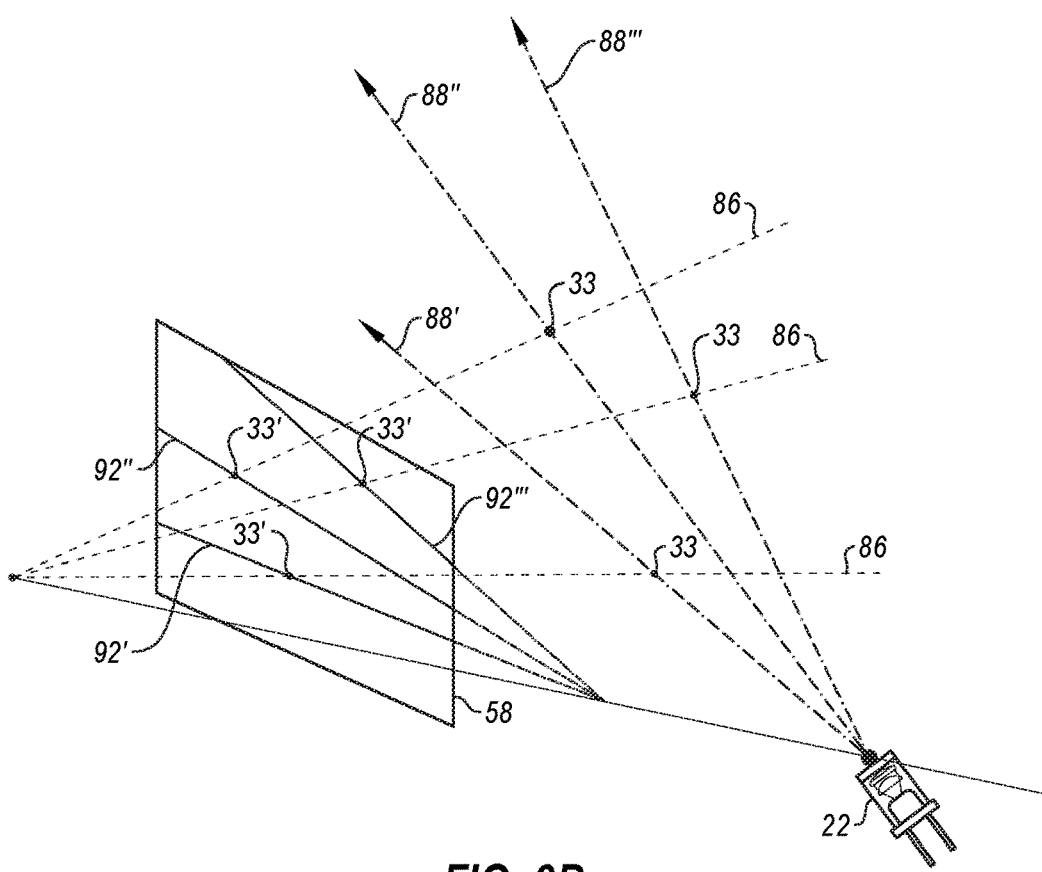

Reference is now made to FIGS. 6A-B, which are schematic illustrations of a structured light projector 22 projecting discrete unconnected spots 33 and a camera sensor 58 detecting spots 33', in accordance with some applications of the present invention. For some applications, a method is provided for determining correspondence between the projected spots 33 on the intraoral surface and detected spots 33' on respective camera sensors 58. Once the correspondence is determined, a three-dimensional image of the surface is reconstructed. Each camera sensor 58 has an array of pixels, for each of which there exists a corresponding camera ray 86. Similarly, for each projected spot 33 from each projector 22 there exists a corresponding projector ray 88. Each projector ray 88 corresponds to a respective path 92 of pixels on at least one of camera sensors 58. Thus, if a camera sees a spot 33' projected by a specific projector ray 88, that spot 33' will necessarily be detected by a pixel on the specific path 92 of pixels that corresponds to that specific projector ray 88. With specific reference to FIG. 6B, the correspondence between respective projector rays 88 and respective camera sensor paths 92 is shown. Projector ray 88' corresponds to camera sensor path 92', projector ray 88'' corresponds to camera sensor path 92'', and projector ray 88''' corresponds to camera sensor path 92'''. For example, if a specific projector ray 88 were to project a spot into a dust-filled space, a line of dust in the air would be illuminated. The line of dust as detected by camera sensor 58 would follow the same path on camera sensor 58 as the camera sensor path 92 that corresponds to the specific projector ray 88.

During a calibration process, calibration values are stored based on camera rays 86 corresponding to pixels on camera sensor 58 of each one of cameras 24, and projector rays 88 corresponding to projected spots 33 of light from each structured light projector 22. For example, calibration values may be stored for (a) a plurality of camera rays 86 corresponding to a respective plurality of pixels on camera sensor 58 of each one of cameras 24, and (b) a plurality of projector rays 88 corresponding to a respective plurality of projected spots 33 of light from each structured light projector 22.

By way of example, the following calibration process may be used. A high accuracy dot target, e.g., black dots on a white background, is illuminated from below and an image is taken of the target with all the cameras. The dot target is then moved perpendicularly toward the cameras, i.e., along the z-axis, to a target plane. The dot-centers are calculated for all the dots in all respective z-axis positions to create a three-dimensional grid of dots in space. A distortion and camera pinhole model is then used to find the pixel coordinate for each three-dimensional position of a respective dot-center, and thus a camera ray is defined for each pixel as a ray originating from the pixel whose direction is towards a corresponding dot-center in the three-dimensional grid. The camera rays corresponding to pixels in between the grid points can be interpolated. The above-described camera calibration procedure is repeated for all respective wavelengths of respective laser diodes 36, such that included in the stored calibration values are camera rays 86 corresponding to each pixel on each camera sensor 58 for each of the wavelengths.

After cameras 24 have been calibrated and all camera ray 86 values stored, structured light projectors 22 may be calibrated as follows. A flat featureless target is used and structured light projectors 22 are turned on one at a time. Each spot is located on at least one camera sensor 58. Since cameras 24 are now calibrated, the three-dimensional spot location of each spot is computed by triangulation based on images of the spot in multiple different cameras. The above-described process is repeated with the featureless target located at multiple different z-axis positions. Each projected spot on the featureless target will define a projector ray in space originating from the projector.

Figure 7:
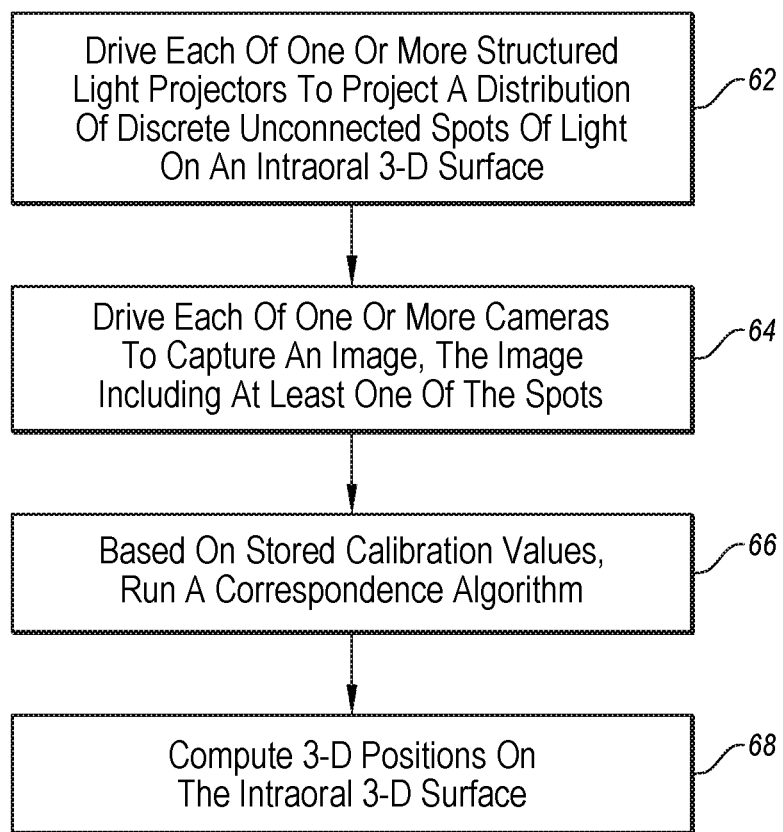
FIG. 7 is a flow chart outlining a method for generating a digital three-dimensional image, in accordance with some applications of the present invention.

Reference is now made to FIG. 7, which is a flow chart outlining a method for generating a digital three-dimensional image, in accordance with some applications of the present invention. In steps 62 and 64, respectively, of the method outlined by FIG. 7 each structured light projector 22 is driven to project distribution 34 of discrete unconnected spots 33 of light on an intraoral three-dimensional surface, and each camera 24 is driven to capture an image that includes at least one of spots 33. Based on the stored calibration values indicating (a) a camera ray 86 corresponding to each pixel on camera sensor 58 of each camera 24, and (b) a projector ray 88 corresponding to each projected spot 33 of light from each structured light projector 22, a correspondence algorithm is run in step 66 using a processor 96 (FIG. 1), further described hereinbelow with reference to FIGS. 8-12. Once the correspondence is solved, three-dimensional positions on the intraoral surface are computed in step 68 and used to generate a digital three-dimensional image of the intraoral surface. Furthermore, capturing the intraoral scene using multiple cameras 24 provides a signal to noise improvement in the capture by a factor of the square root of the number of cameras.

Figure 8:
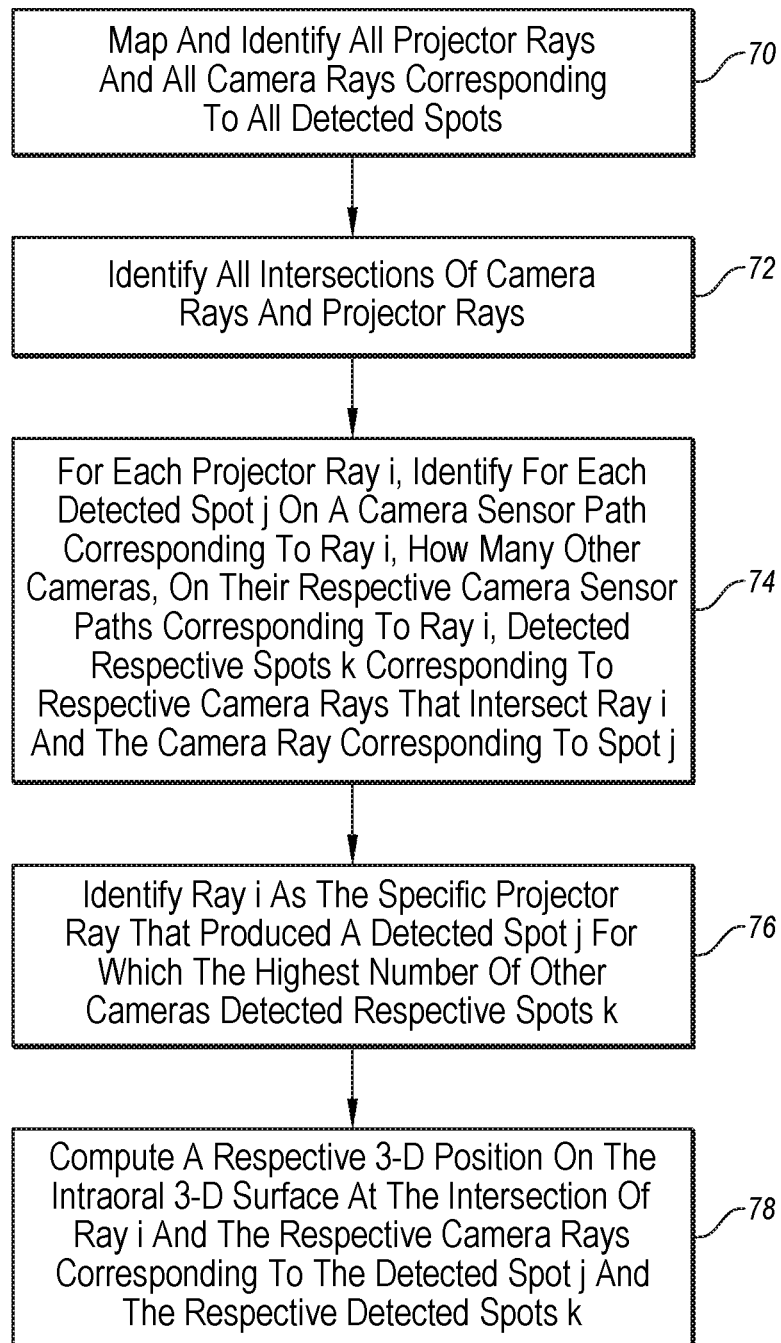
FIG. 8 is a flowchart outlining a method for carrying out a specific step in the method of FIG. 7, in accordance with some applications of the present invention.
Figure 9:
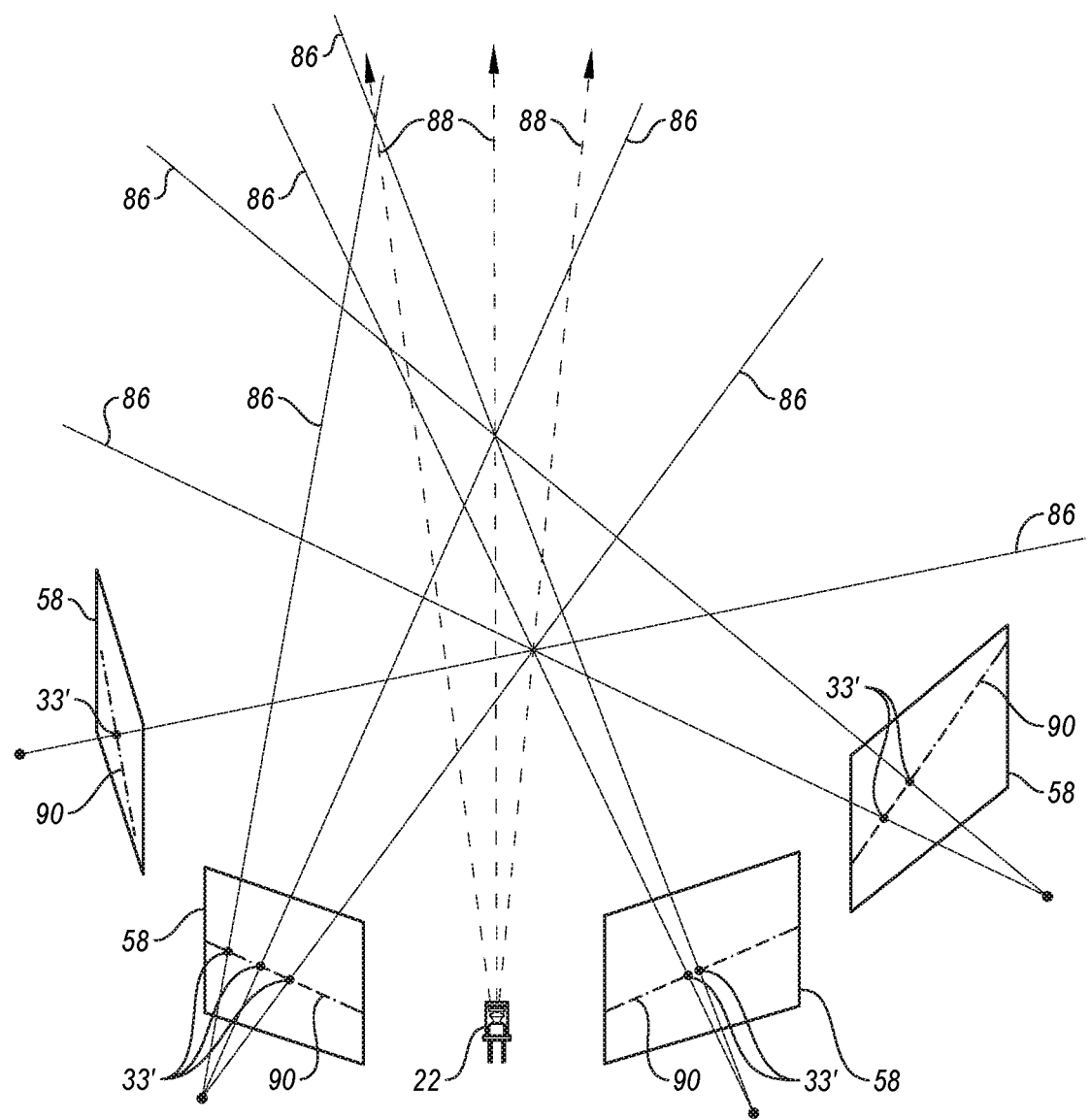
FIGS. 9, 10, 11, and 12 are schematic illustrations depicting a simplified example of the steps of FIG. 8, in accordance with some applications of the present invention.
Figure 10:
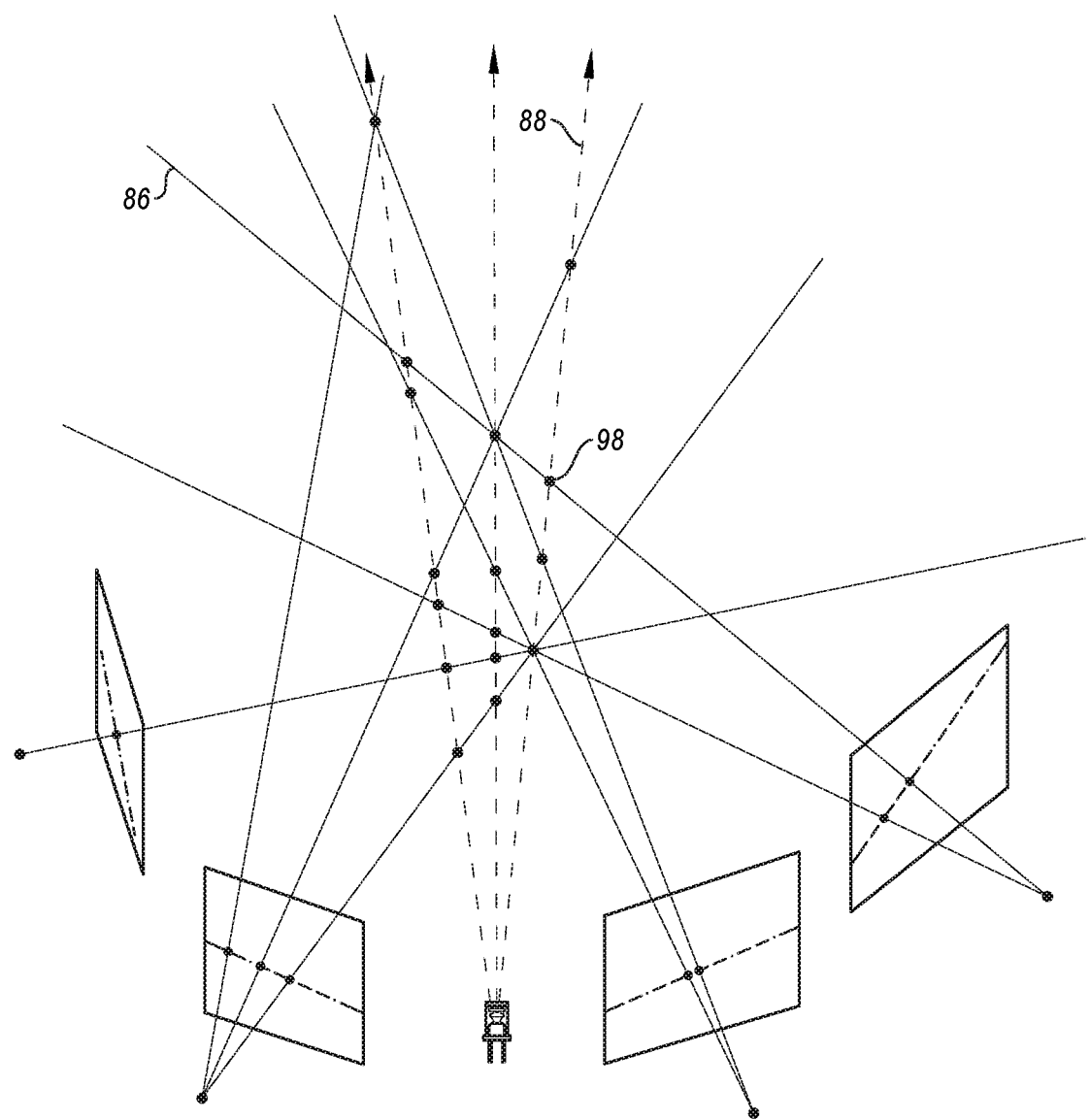

Reference is now made to FIG. 8, which is a flowchart outlining the correspondence algorithm of step 66 in FIG. 7, in accordance with some applications of the present invention. Based on the stored calibration values, all projector rays 88 and all camera rays 86 corresponding to all detected spots 33' are mapped (step 70), and all intersections 98 (FIG. 10) of at least one camera ray 86 and at least one projector ray 88 are identified (step 72). FIGS. 9 and 10 are schematic illustrations of a simplified example of steps 70 and 72 of FIG. 8, respectively. As shown in FIG. 9, three projector rays 88 are mapped along with eight camera rays 86 corresponding to a total of eight detected spots 33' on camera sensors 58 of cameras 24. As shown in FIG. 10, sixteen intersections 98 are identified.

Figure 11:
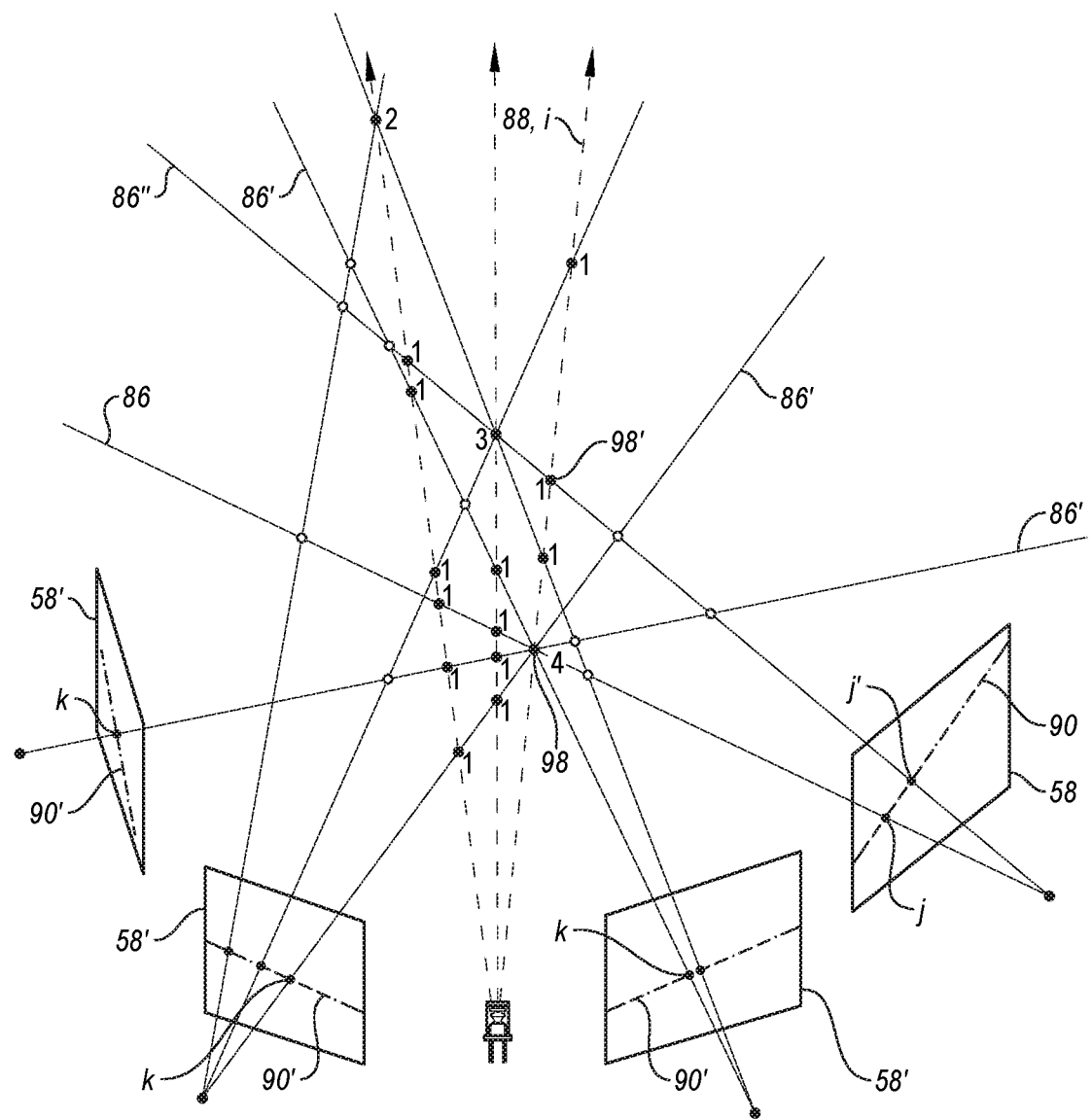

In steps 74 and 76 of FIG. 7, processor 96 determines a correspondence between projected spots 33 and detected spots 33' so as to identify a three-dimensional location for each projected spot 33 on the surface. FIG. 11 is a schematic illustration depicting steps 74 and 76 of FIG. 8 using the simplified example described hereinabove in the immediately preceding paragraph. For a given projector ray i, processor 96 "looks" at the corresponding camera sensor path 90 on camera sensor 58 of one of cameras 24. Each detected spot j along camera sensor path 90 will have a camera ray 86 that intersects given projector ray i, at an intersection 98. Intersection 98 defines a three-dimensional point in space. Processor 96 then "looks" at camera sensor paths 90' that correspond to given projector ray i on respective camera sensors 58' of other cameras 24, and identifies how many other cameras 24, on their respective camera sensor paths 90' corresponding to given projector ray i, also detected respective spots k whose camera rays 86' intersect with that same three-dimensional point in space defined by intersection 98. The process is repeated for all detected spots j along camera sensor path 90, and the spot j for which the highest number of cameras 24 "agree," is identified as the spot 33 (FIG. 12) that is being projected onto the surface from given projector ray i. That is, projector ray i is identified as the specific projector ray 88 that produced a detected spot j for which the highest number of other cameras detected respective spots k. A three-dimensional position on the surface is thus computed for that spot 33.

Figure 12:
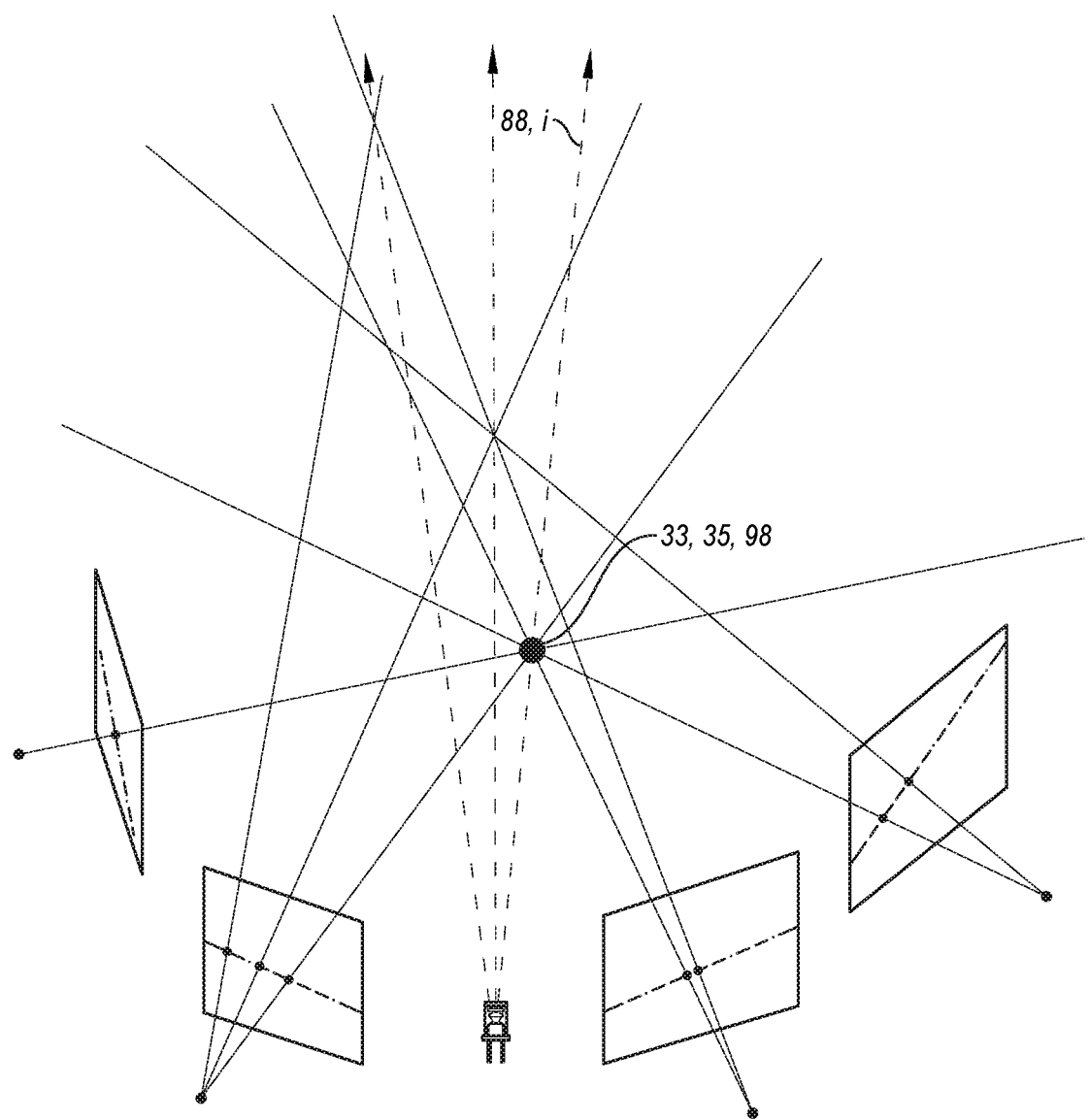

For example, as shown in FIG. 11, all four of the cameras detect respective spots, on their respective camera sensor paths corresponding to projector ray i, whose respective camera rays intersect projector ray i at intersection 98, intersection 98 being defined as the intersection of camera ray 86 corresponding to detected spot j and projector ray i. Hence, all four cameras are said to "agree" on there being a spot 33 projected by projector ray i at intersection 98. When the process is repeated for a next spot j', however, none of the other cameras detect respective spots, on their respective camera sensor paths corresponding to projector ray i, whose respective camera rays intersect projector ray i at intersection 98', intersection 98' being defined as the intersection of camera ray 86" (corresponding to detected spot j') and projector ray i. Thus, only one camera is said to "agree" on there being a spot 33 projected by projector ray i at intersection 98', while four cameras "agree" on there being a spot 33 projected by projector ray i at intersection 98. Projector ray i is therefore identified as being the specific projector ray 88 that produced detected spot j, by projecting a spot 33 onto the surface at intersection 98 (FIG. 12). As per step 78 of FIG. 8, and as shown in FIG. 12, a three-dimensional position 35 on the intraoral surface is computed at intersection 98.

Figure 13:
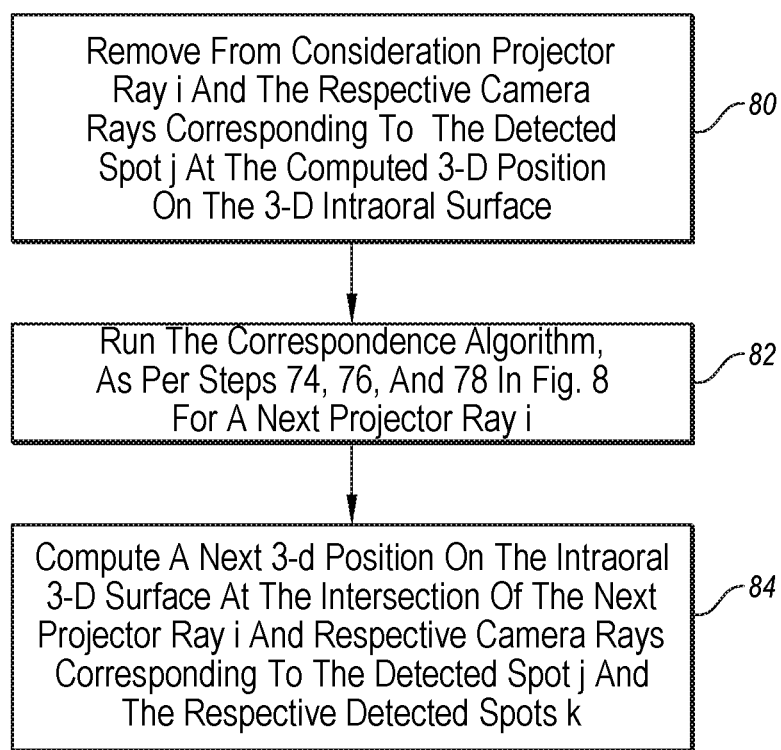
FIG. 13 is a flow chart outlining further steps in the method for generating a digital three-dimensional image, in accordance with some applications of the present invention.
Figure 14:
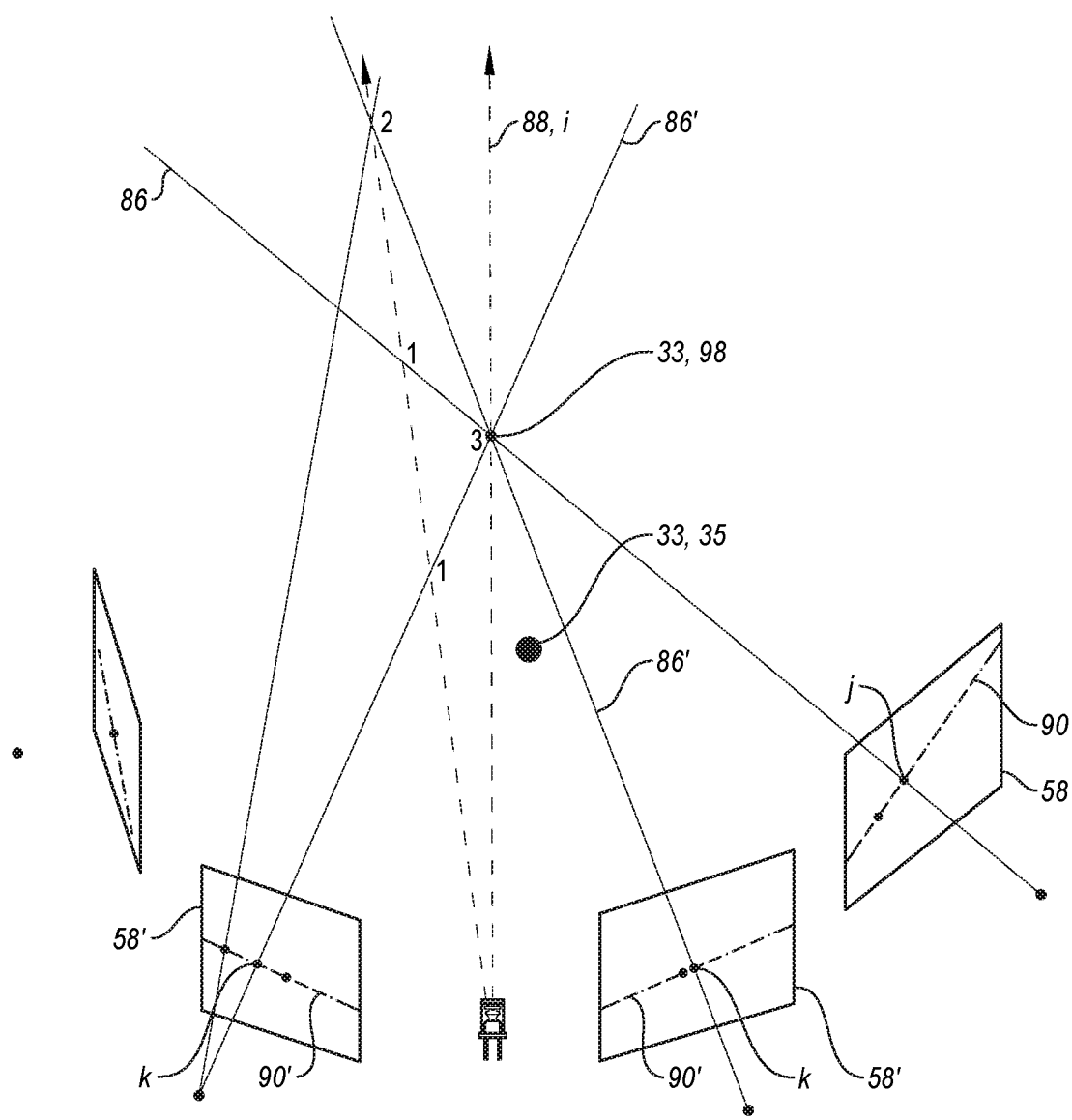
FIGS. 14, 15, 16, and 17 are schematic illustrations depicting a simplified example of the steps of FIG. 13, in accordance with some applications of the present invention.
Figure 15:
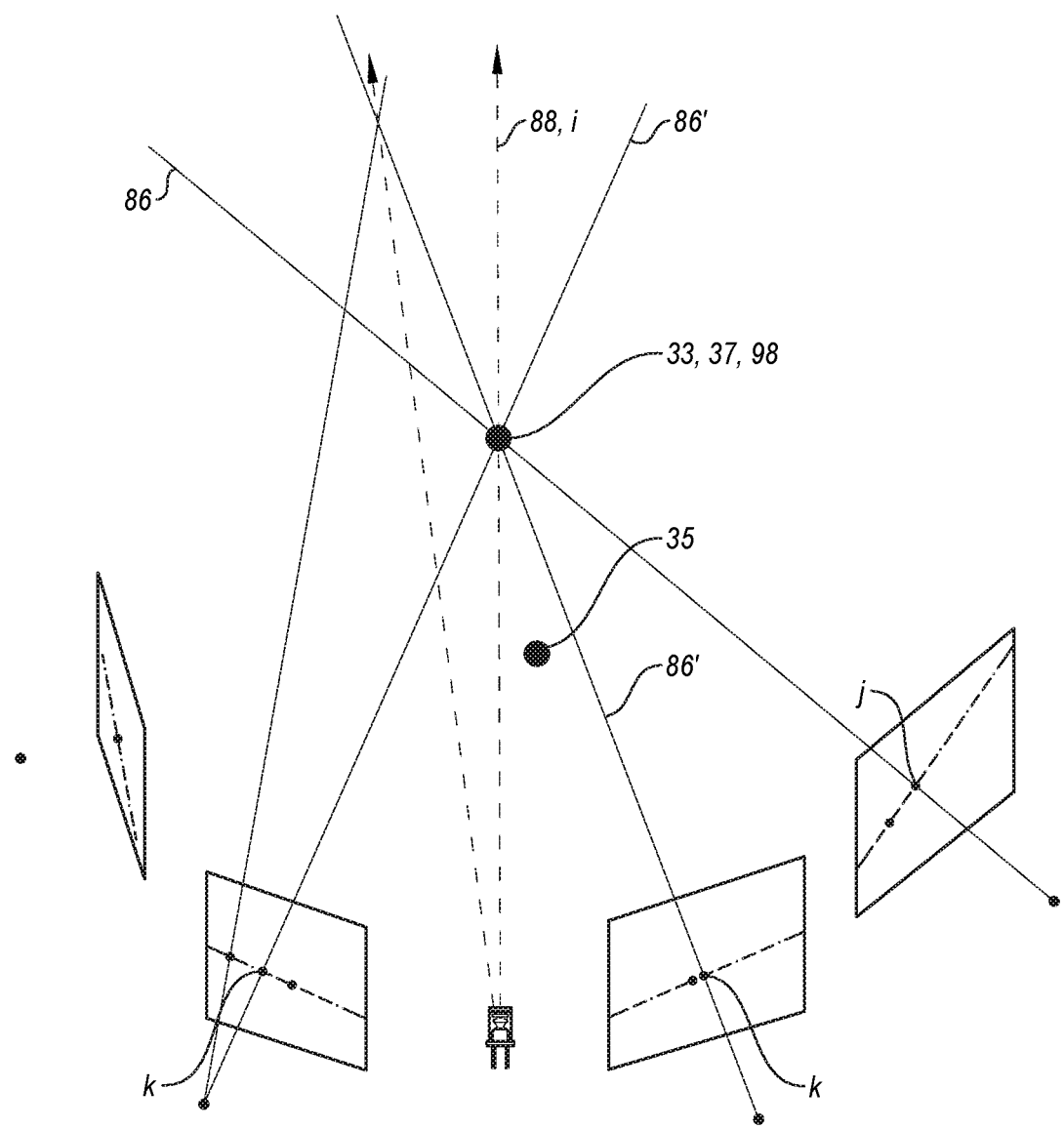

Reference is now made to FIG. 13, which is a flow chart outlining further steps in the correspondence algorithm, in accordance with some applications of the present invention. Once position 35 on the surface is determined, projector ray i that projected spot j, as well as all camera rays 86 and 86' corresponding to spot j and respective spots k are removed from consideration (step 80) and the correspondence algorithm is run again for a next projector ray i (step 82). FIG. 14 depicts the simplified example described hereinabove after the removal of the specific projector ray i that projected spot 33 at position 35. As per step 82 in the flow chart of FIG. 13, the correspondence algorithm is then run again for a next projector ray i. As shown in FIG. 14, the remaining data show that three of the cameras "agree" on there being a spot 33 at intersection 98, intersection 98 being defined by the intersection of camera ray 86 corresponding to detected spot j and projector ray i. Thus, as shown in FIG. 15, a three-dimensional position 37 is computed at intersection 98.

Figure 16:
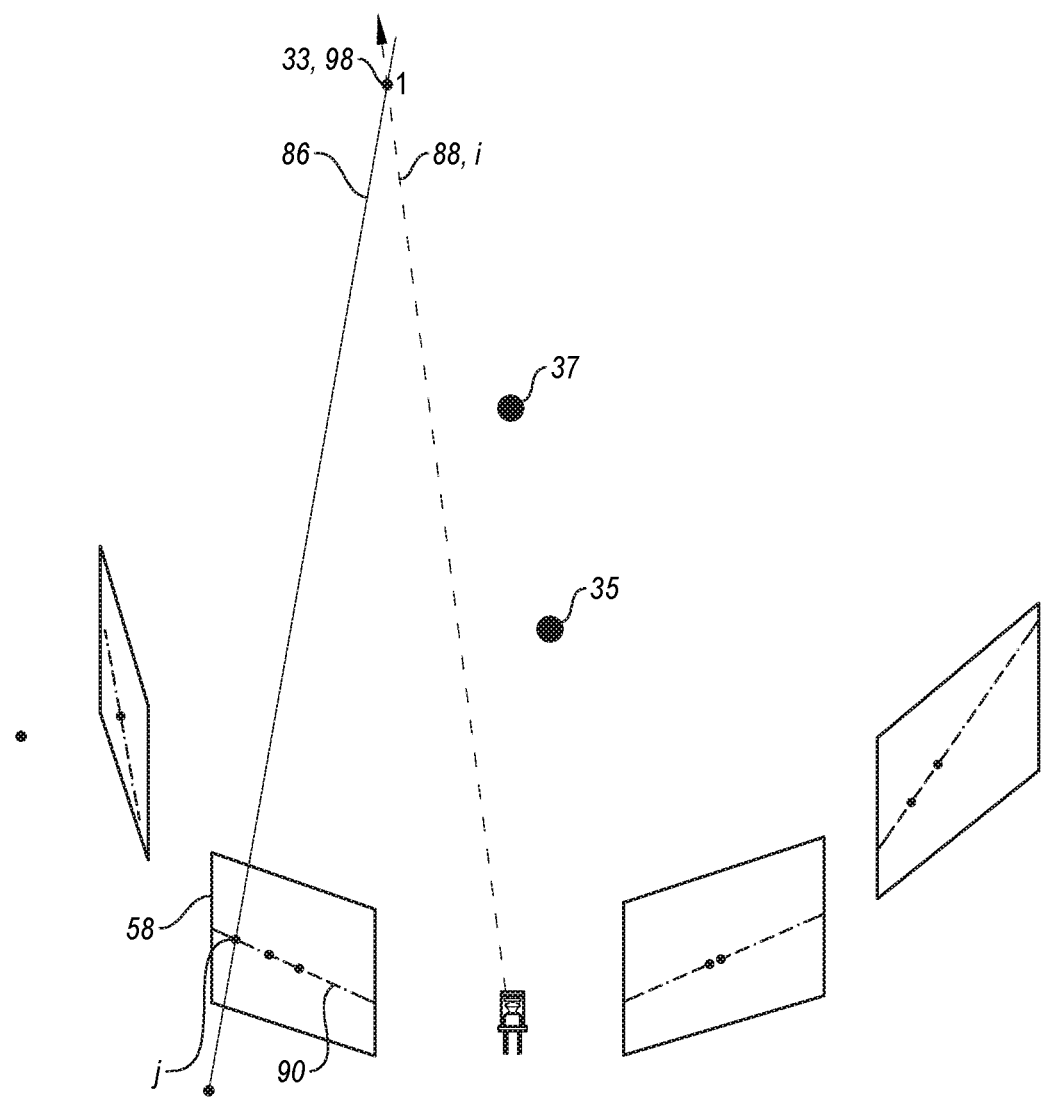
Figure 17:
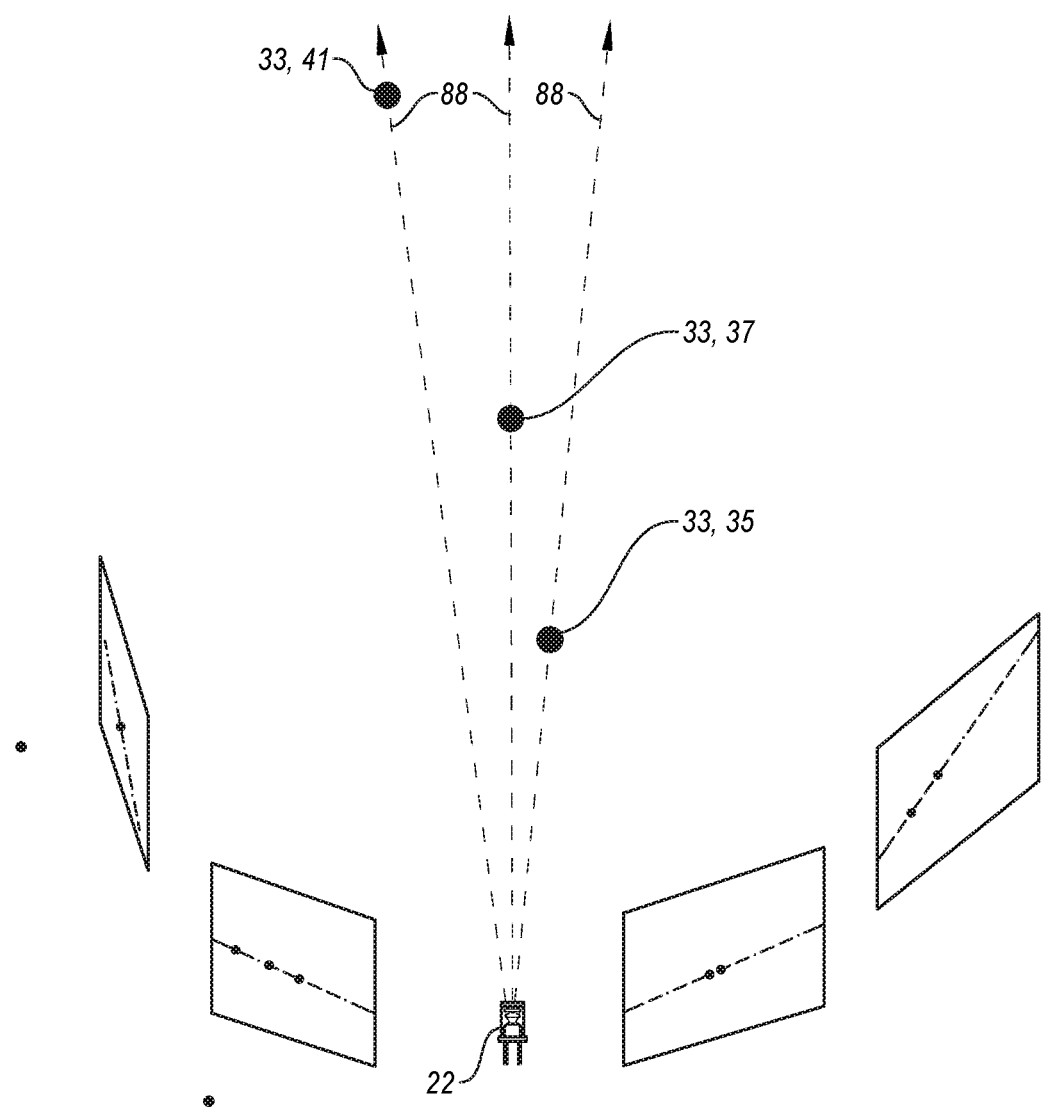

As shown in FIG. 16, once three-dimensional position 37 on the surface is determined, again projector ray i that projected spot j, as well as all camera rays 86 and 86' corresponding to spot j and respective spots k are removed from consideration. The remaining data show a spot 33 projected by projector ray i at intersection 98, and a three-dimensional position 41 on the surface is computed at intersection 98. As shown in FIG. 17, according to the simplified example, the three projected spots 33 of the three projector rays 88 of structured light projector 22 have now been located on the surface at three-dimensional positions 35, 37, and 41. In some applications, each structured light projector 22 projects 400—3000 spots 33. Once correspondence is solved for all projector rays 88, a reconstruction algorithm may be used to reconstruct a digital image of the surface using the computed three-dimensional positions of the projected spots 33.

Reference is again made to FIG. 1. For some applications, there is at least one uniform light projector 118 coupled to rigid structure 26. Uniform light projector 118 transmits white light onto object 32 being scanned. At least one camera, e.g., one of cameras 24, captures two-dimensional color images of object 32 using illumination from uniform light projector 118. Processor 96 may run a surface reconstruction algorithm that combines at least one image captured using illumination from structured light projectors 22 with a plurality of images captured using illumination from uniform light projector 118 in order to generate a digital three-dimensional image of the intraoral three-dimensional surface. Using a combination of structured light and uniform illumination enhances the overall capture of the intraoral scanner and may help reduce the number of options that processor 96 needs to consider when running the correspondence algorithm.

For some applications, structured light projectors 22 are simultaneously driven to project their respective distributions 34 of discrete unconnected spots 33 of light on the intraoral three-surface. Alternatively, structured light projectors 22 may be driven to project their respective distributions 34 of discrete unconnected spots 33 of light on the intraoral three-surface at different respective times, e.g., in a predetermined order, or in an order that is dynamically determined during a scan. Alternatively, for some applications, a single structured light projector 22 may be driven to project distribution 34.

Dynamically determining which structured light projectors 22 to activate during a scan may improve overall signal quality of the scan as some of the structured light projectors may have better signal quality in some regions of the intraoral cavity relative to other regions. For example, when scanning a subject's palate (upper jaw region) the red projectors tend to have better signal quality than the blue projectors. Additionally, hard-to-see regions within the intraoral cavity may be encountered during a scan, e.g., an area with missing teeth or narrow cracks between big teeth. In these types of cases, dynamically determining which structured light projector 22 to activate during a scan allows specific projectors that may have better line of sight to the region in question to be activated.

For some applications, different structured light projectors 22 may be configured to focus at different object focal planes. Dynamically determining which structured light projectors 22 to activate during a scan allows for activating specific structured light projectors 22 according to their respective object focal planes depending on a distance from a region currently being scanned.

For some applications, all data points taken at a specific time are used as a rigid point cloud, and multiple such point clouds are captured at a frame rate of over 10 captures per second. The plurality of point clouds are then stitched together using a registration algorithm, e.g., iterative closest point (ICP), to create a dense point cloud. A surface reconstruction algorithm may then be used to generate a representation of the surface of object 32.

For some applications, at least one temperature sensor 52 is coupled to rigid structure 26 and measures a temperature of rigid structure 26. Temperature control circuitry 54 disposed within handheld wand 20 (a) receives data from temperature sensor 52 indicative of the temperature of rigid structure 26 and (b) activates a temperature control unit 56 in response to the received data. Temperature control unit 56, e.g., a PID controller, keeps probe 28 at a desired temperature (e.g., between 35 and 43 degrees Celsius, between 37 and 41 degrees Celsius, etc.). Keeping probe 28 above 35 degrees Celsius, e.g., above 37 degrees Celsius, reduces fogging of the glass surface of handheld wand 20, through which structured light projectors 22 project and cameras 24 view, as probe 28 enters the intraoral cavity, which is typically around or above 37 degrees Celsius. Keeping probe 28 below 43 degrees, e.g., below 41 degrees Celsius, prevents discomfort or pain.

Additionally, in order for the stored calibration values of the camera rays and the projector rays to be of use during a scan, the temperature of cameras 24 and structured light projectors 22 may be prevented from varying so as to maintain geometrical integrity of the optics. A variation in temperature can cause the length of probe 28 to change due to thermal expansion, which in turn may cause the respective camera and projector positions to shift. Due to different types of stress that may build up within probe 28 during such thermal expansion, twisting can also occur, causing the angles of the respective camera rays and projector rays to shift as well. Within the cameras and projectors, geometric changes may occur due to temperature variation as well. For example, DOE 39 may expand and alter the projected pattern, temperature variations may affect the refractive index of the camera lenses, or temperature variations may change the wavelengths transmitted by laser diodes 36. Therefore, in addition to keeping probe 28 at a temperature within the range described above, temperature control unit 56 may further prevent the temperature of probe 28 from varying by more than 1 degree when handheld wand 20 is in use, so as to maintain geometrical integrity of the optics disposed within probe 28. For example, if temperature control unit 56 is keeping probe 28 at a temperature of 39 degrees Celsius then temperature control unit 56 will further ensure that during use the temperature of probe 28 does not go below 38 degrees Celsius or above 40 degrees Celsius.

For some applications, probe 28 is maintained at its controlled temperature through the use of a combination of heating and cooling. For example, temperature control unit 56 may include a heater, e.g., a plurality of heaters, and a cooler, e.g., a thermoelectric cooler. If the temperature of probe 28 drops below degrees Celsius the heater(s) may be used to raise the temperature of probe 28, and if the temperature of probe 28 goes above 40 degrees Celsius, the thermoelectric cooler may be used to lower the temperature of probe 28.

Alternatively, for some applications, probe 28 is maintained at its controlled temperature through the use of heating only, without cooling. The use of laser diodes 36 and diffractive and/or refractive pattern generating optical elements helps maintain an energy efficient structured light projector so as to limit probe 28 from heating up during use; laser diodes 36 may use less than 0.2 Watts of power while transmitting at a high brightness and diffractive and/or refractive pattern generating optical elements utilize all the transmitted light (in contrast, for example, to a mask which stops some of the rays from hitting the object). External environmental temperatures, such as those encountered within a subject's intraoral cavity, may however cause heating of probe 28. To overcome this, heat may be drawn out of the probe 28 via a heat conducting element 94, e.g., a heat pipe, that is disposed within handheld wand 20, such that a distal end 95 of heat conducting element 94 is in contact with rigid structure 26 and a proximal end 99 is in contact with a proximal end 100 of handheld wand 20. Heat is thereby transferred from rigid structure 26 to proximal end 100 of handheld wand 20. Alternatively or additionally, a fan disposed in a handle region 174 of handheld wand 20 may be used to draw heat out of probe 28.

For some applications, alternatively or additionally to maintaining geometric integrity of the optics by preventing the temperature of probe 28 from varying by more than a threshold change in temperature, processor 96 may select between a plurality of sets of calibration data corresponding to different temperatures respectively. For example, the threshold change may be 1 degree Celsius. Based on data received from temperature sensor 52 indicative of the temperature of structured light projectors 22 and cameras 24, processor 96 may select between a plurality of sets of stored calibration data corresponding to a plurality of respective temperatures of structured light projectors 22 and cameras 24, each set of stored calibration data indicating for a respective temperature (a) the projector ray corresponding to each of the projected spots of light from each one of the one or more projectors, and (b) the camera ray corresponding to each pixel on the camera sensor of each one of the one or more cameras. If processor 96 only has access to stored calibration data for a specific plurality of temperatures, processor 96 may interpolate between the plurality of sets of stored calibration data based on data received from temperature sensor 52, in order to obtain calibration data for temperatures between the respective temperatures corresponding to each set of calibration data.

Figure 18:
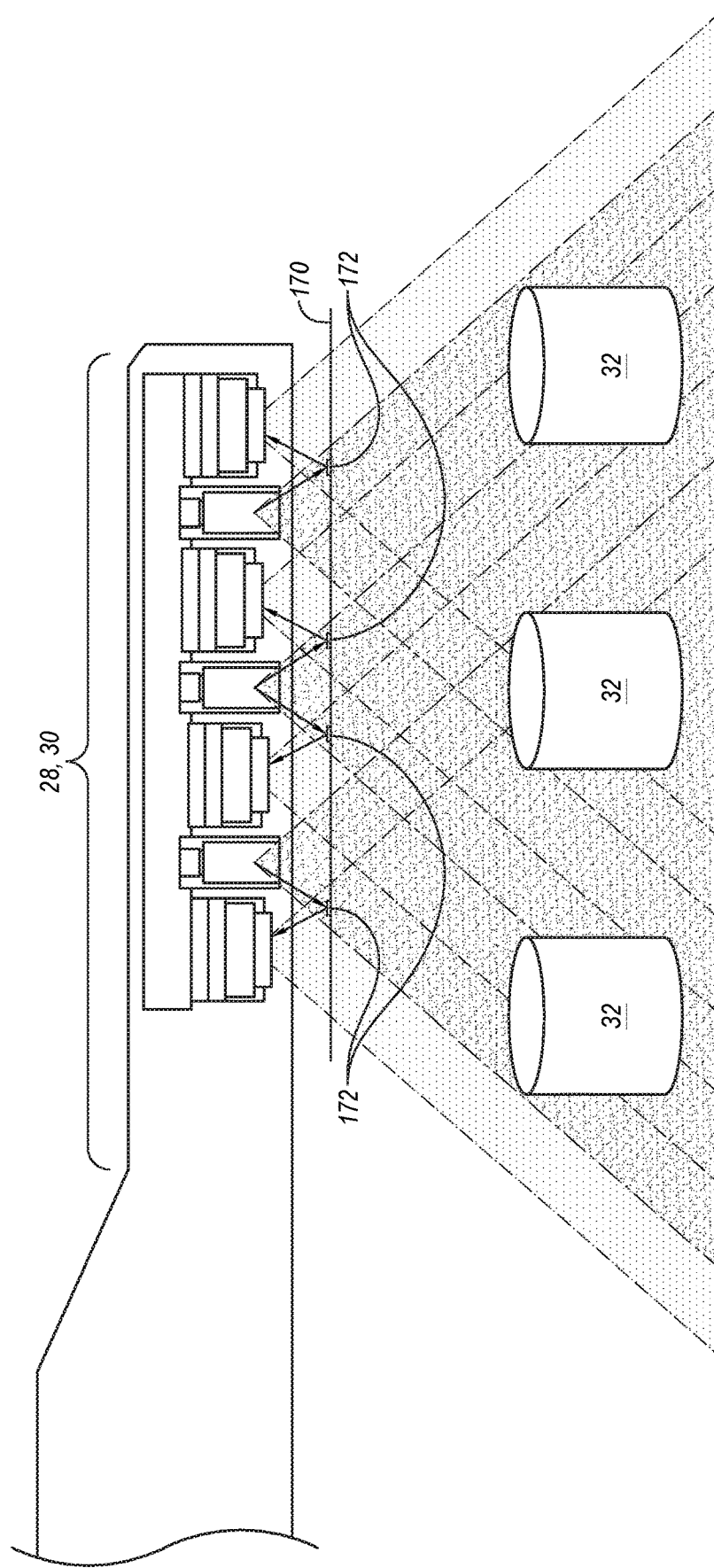
FIG. 18 is a schematic illustration of the probe including a diffuse reflector, in accordance with some applications of the present invention.

Reference is now made to FIG. 18, which is a schematic illustration of probe 28, in accordance with some applications of the present invention. For some applications, probe 28 further includes a target such as a diffuse reflector 170 having a plurality of regions 172 disposed within probe 28 (or, as shown in FIG. 18, adjacent to probe 28). In some applications, (a) each structured light projector 22 may have at least one region 172 of diffuse reflector 170 in its field of illumination, (b) each camera 24 has at least one region 172 of diffuse reflector 170 in its field of view, and (c) a plurality of regions 172 of diffuse reflector 170 are in the field of view of a camera 24 and in the field of illumination of a structured light projector 22. Alternatively or additionally to maintaining geometric integrity of the optics by preventing the temperature of probe 28 from varying by more than a threshold temperature change, processor 96 may (a) receive data from cameras 24 indicative of the position of the diffuse reflector with respect to distribution 34 of discrete unconnected spots 33 of light, (b) compare the received data to a stored calibration position of diffuse reflector 170, wherein a discrepancy between (i) the received data indicative of the position of diffuse reflector 170 and (ii) the stored calibration position of diffuse reflector 170, indicates a shift of projector rays 88 and cameras rays 86 from their respective stored calibration values, and (c) run the correspondence algorithm based on the shift of projector rays 88 and cameras rays 86.

Alternatively or additionally, a discrepancy between (i) the received data indicative of the position of diffuse reflector 170 and (ii) the stored calibration position of diffuse reflector 170 may indicate a change in temperature of probe 28. In this case the temperature of probe 28 may be regulated based on the comparison of the received data and the stored calibration position of diffuse reflector 170.

Hereinbelow is described a plurality of applications for structured light projectors 22.

Figure 19B:
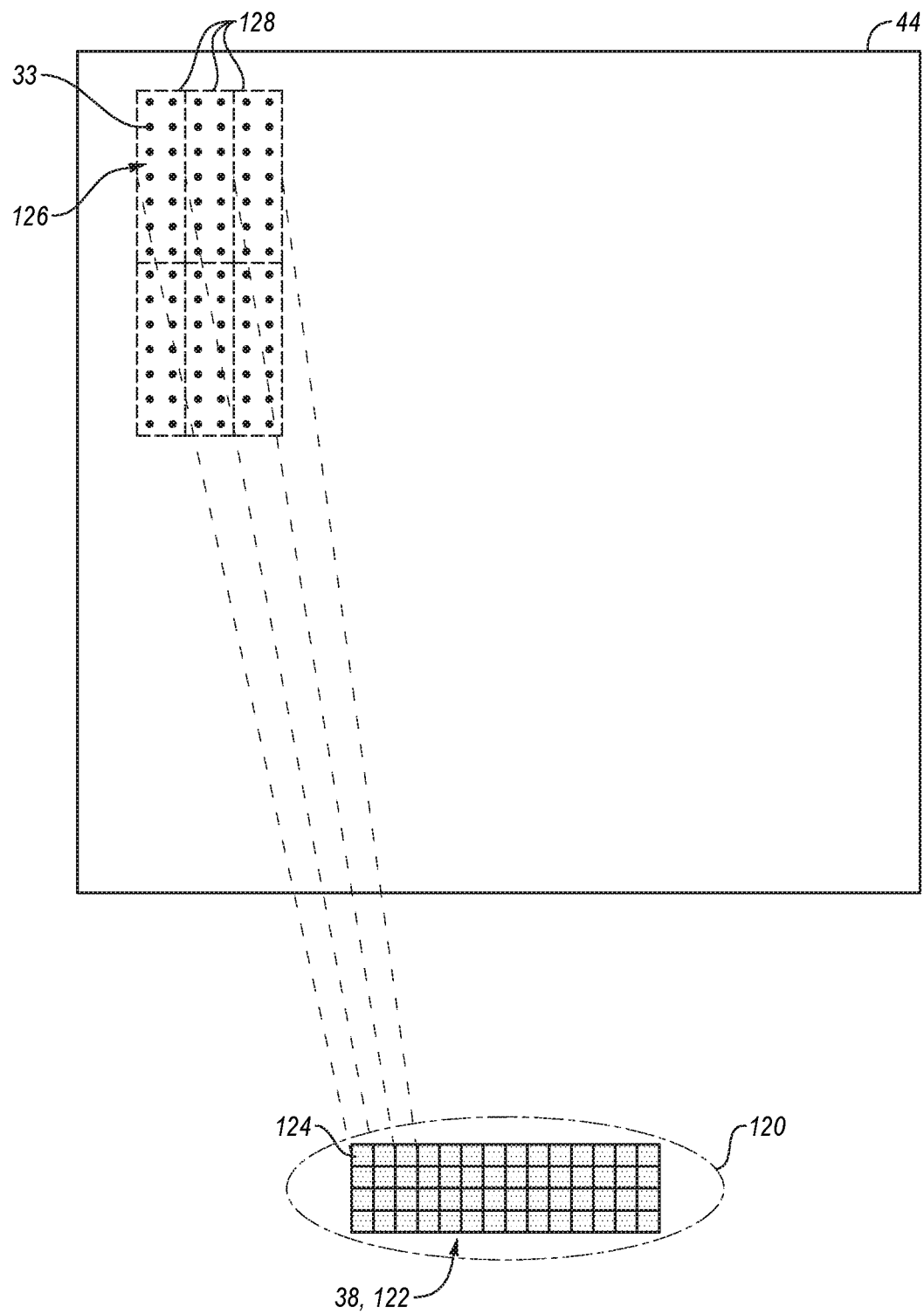

Reference is now made to FIG. 19A-B, which are schematic illustrations of structured light projector 22 and a cross-section of a beam 120 of light transmitted by a laser diode 36, with a pattern generating optical element 38 shown disposed in the light path of the beam, in accordance with some applications of the present invention. In some applications, each laser diode 36 transmits an elliptical beam 120 whose elliptical cross-section has (a) a long axis of at least 500 microns and/or less than 700 microns and (b) a short axis of at least 100 microns and/or less than 200 microns. For some applications, a small area beam splitter may be used in order to generate a tightly focused spot array, e.g., a DOE having a side length of less than 100 microns may be used in order to maintain projected spots 33 in tight focus over the entire focus range of interest. However, such a small DOE would utilize only a fraction of the light transmitted via elliptical laser beam 120.

Therefore, for some applications, pattern generating optical element 38 is a segmented DOE 122 that is segmented into a plurality of sub-DOE patches 124 that are arranged in an array. The array of sub-DOE patches 124 is positioned so as to (a) be contained within elliptical beam 120 of light and (b) utilize a high percentage, e.g., at least 50% of the light transmitted via elliptical laser beam 120. In some applications, the array is a rectangular array including at least 16 and/or less than 72 sub-DOE patches 124 and has a longest dimension of at least 500 microns and/or less than 800 microns. Each sub-DOE patch 124 may have a square cross-section having a side of length of at least 30 microns and/or less than 75 microns, the cross-section being taken perpendicular to the optical axis of the DOE.

Each sub-DOE patch 124 generates a respective distribution 126 of discrete unconnected spots 33 of light in a different area 128 of the field of illumination. For this application of structured light projector 22, distribution 34 of discrete unconnected spots 33 of light, as described hereinabove with reference to FIG. 4, is a combination of respective distributions 126 generated by respective sub-DOE patches 124. FIG. 19B shows an orthogonal plane 44, on which is shown respective distributions 126 of discrete unconnected spots 33 of light, each respective distribution 126 being in a different area 128 of the field of illumination. Since each sub-DOE patch 124 is responsible for a different area 128 of the field of illumination, each sub-DOE patch 124 has a different design so as to direct its respective distribution 126 in a different direction and avoid beam crossing in order to avoid overlap between projected spots 33.

Figure 20A:
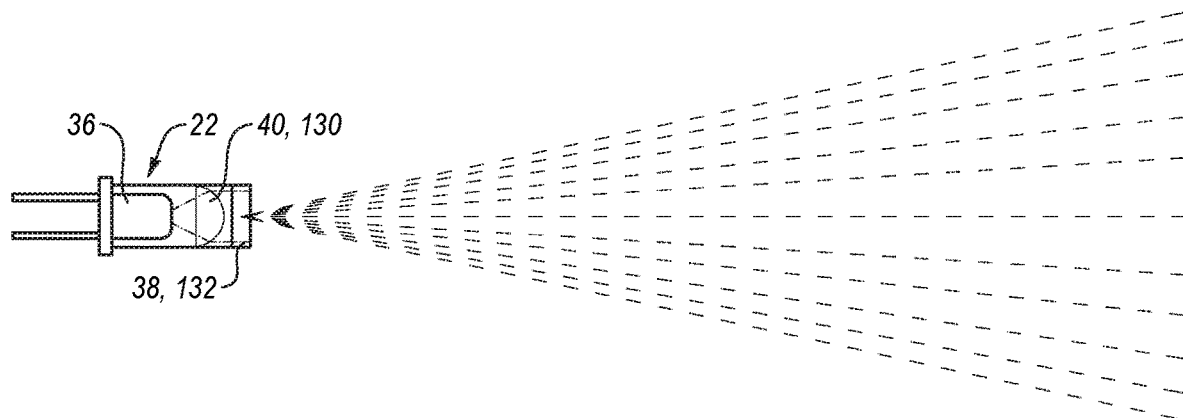
FIGS. 20A-E are schematic illustrations of a micro-lens array used as a pattern generating optical element in a structured light projector, in accordance with some applications of the present invention.
Figure 20B:
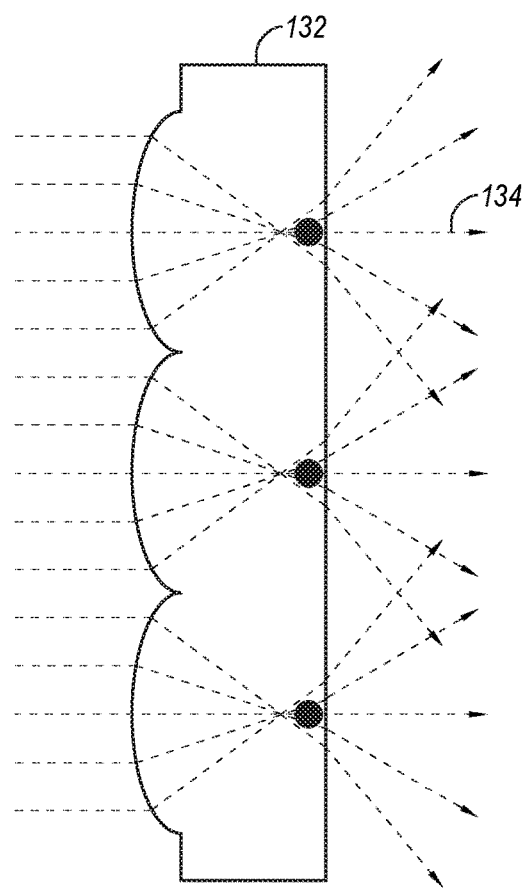
Figure 20C:
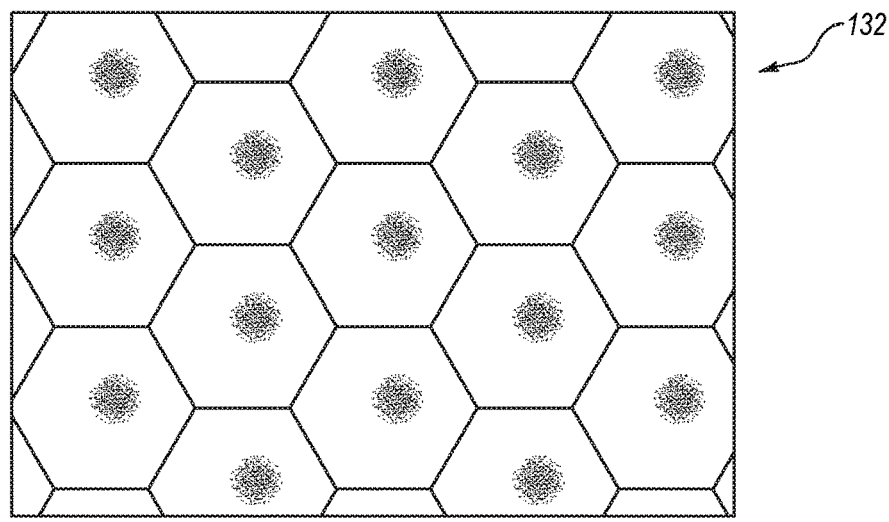
Figure 20D:
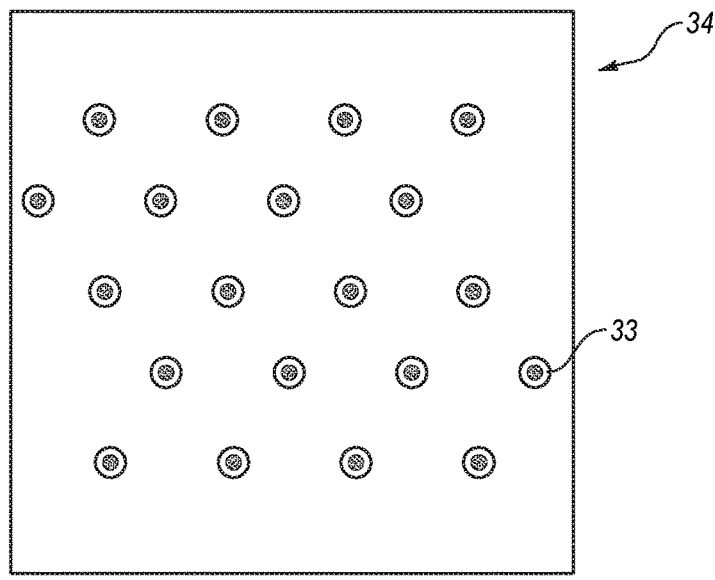
Figure 20E:
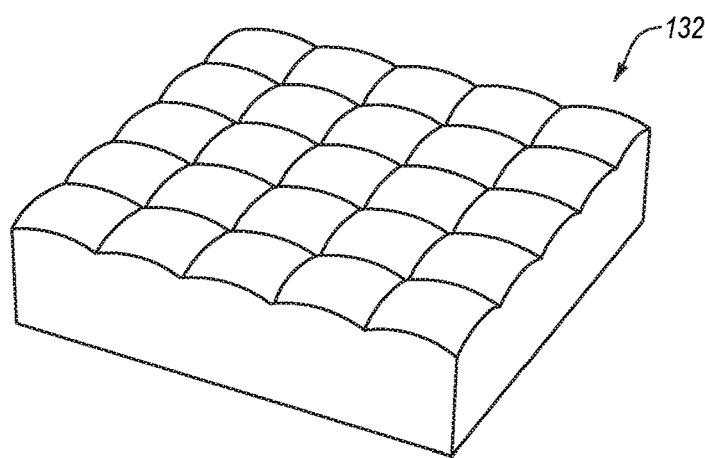

Reference is now made to FIGS. 20A-E, which are schematic illustrations of a micro-lens array 132 as pattern generating optical element 38, in accordance with some applications of the present invention. A micro-lens array can be used as spot generator since it is periodic and the profile variation of each lens in the array is in the wavelength scale. The pitch of micro-lens array 132 is tuned for the desired angular pitch between the spots. The numerical aperture (NA) of micro-lens array 132 is tuned to provide the desired angular field of illumination, as described hereinabove. In some applications, the NA of micro-lens array 132 is at least 0.2 and/or less than 0.7. Micro-lens array 132 may be, for example, a hexagonal micro-lens array, such as is shown in FIG. 20C, or a rectangular micro-lens array, such as is shown in FIG. 20E.

Structured light projectors 22 that have micro-lens array 132 as pattern generating optical element 38 may include laser diode 36, collimating lens 130, an aperture, and micro-lens array 132. The aperture defines a smaller input beam diameter in order to maintain tightly focused spots at a near focal distance, e.g., at least 1 mm and/or less than 30 mm, e.g., at least 4 mm and/or less than 24 mm, from micro-lens array 132. FIG. 20B shows the collimated laser beam illuminating micro-lens array 132, and micro-lens array then generating diverging beams 134 of light, the interference of these diverging beams generating an array of spots 33, e.g., distribution 34 (FIG. 20D). For some applications, the aperture is a chrome film that is applied to the laser-diode-side of collimating lens 130. Alternatively, for some applications, the aperture is a chrome film disposed on the collimating-lens-side of micro-lens array 132. In some applications, the aperture may span a distance of at least 10 times the pitch of micro-lens array 132 and has a diameter of at least 50 microns and/or less than 200 microns.

Figure 21A:
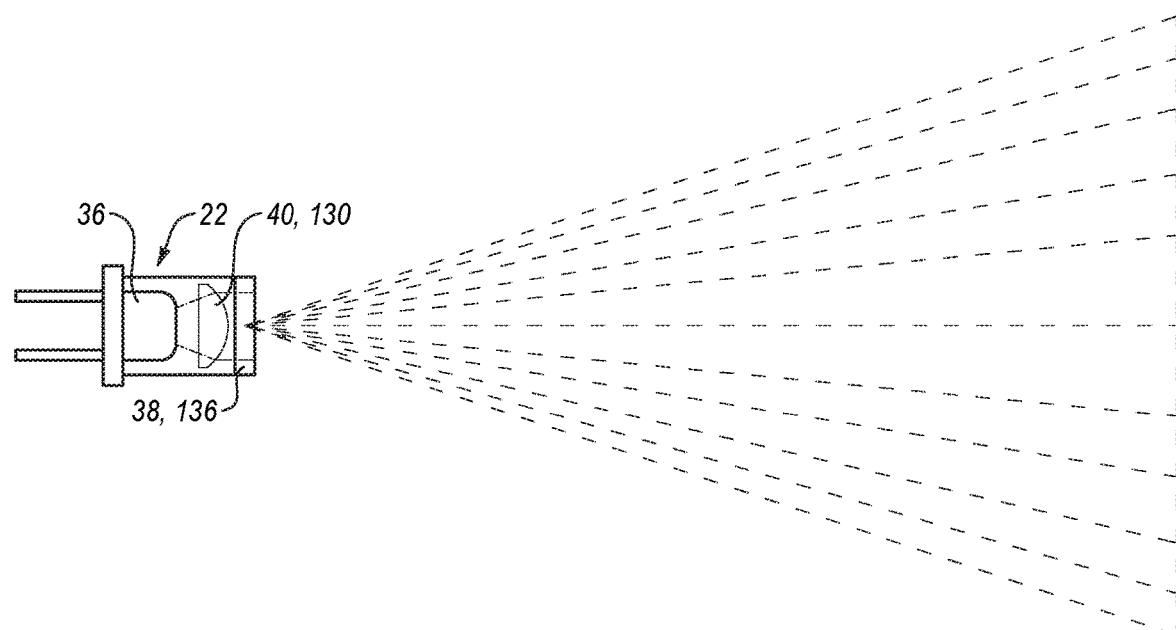
FIGS. 21A-C are schematic illustrations of a compound 2-D diffractive periodic structure used as a pattern generating optical element in a structured light projector, in accordance with some applications of the present invention.
Figure 21B:
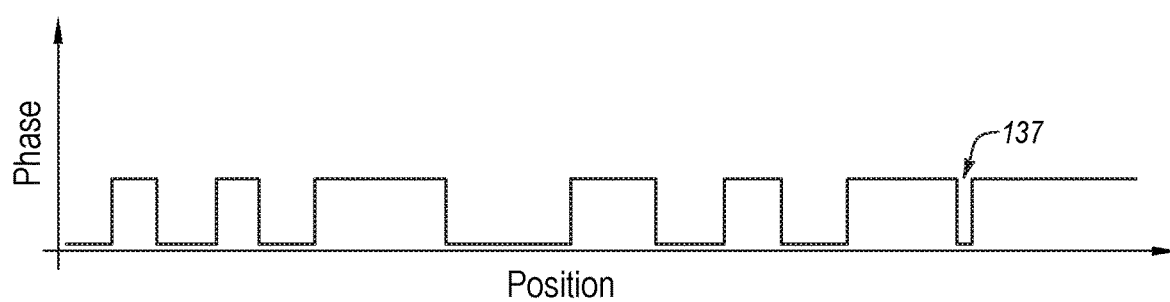
Figure 21C:
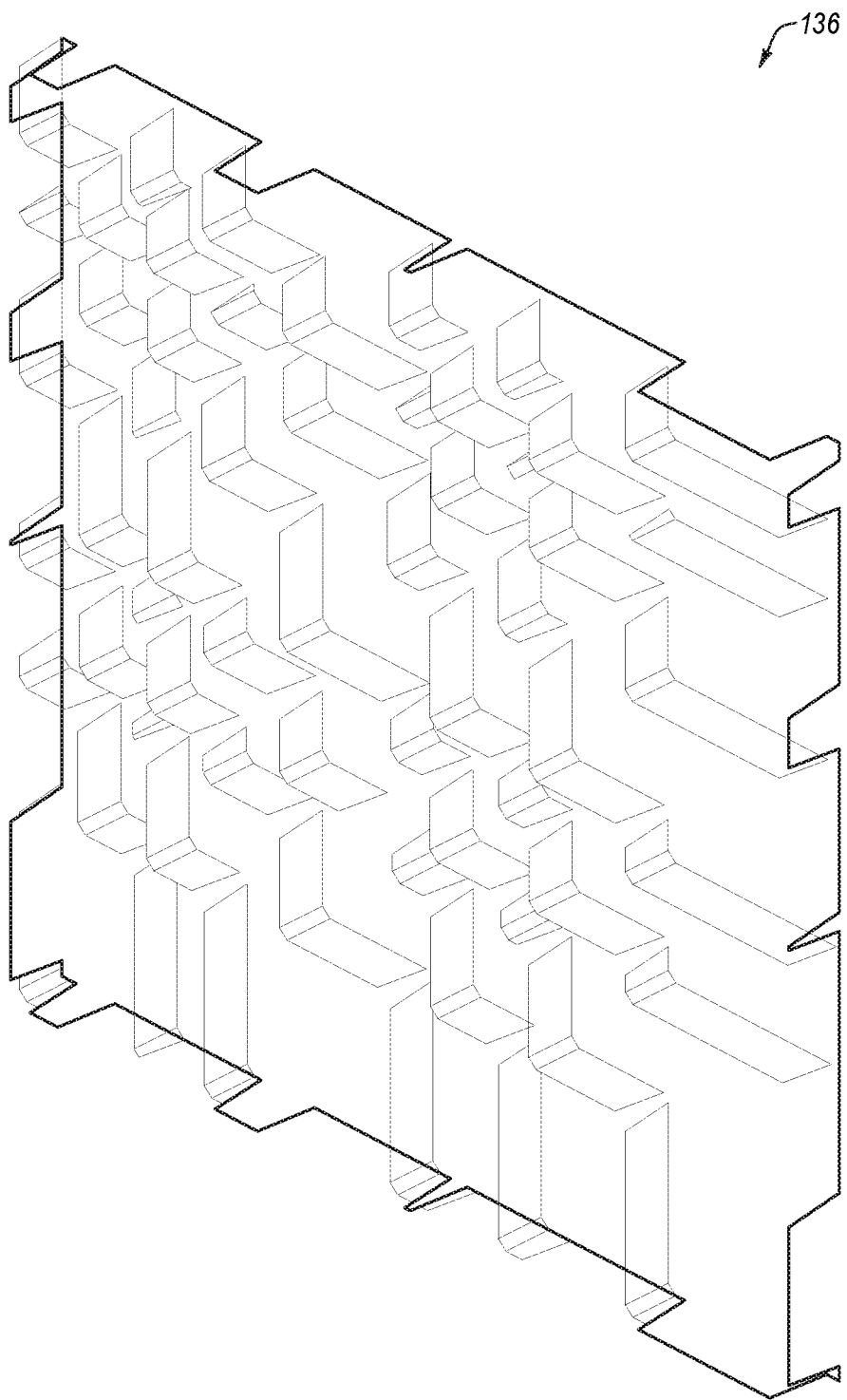

Reference is now made to FIGS. 21A-C, which are schematic illustrations of a compound 2-D diffractive periodic structure 136, e.g., a diffractive grating such as a Dammann grating, as pattern generating optical element 38, in accordance with some applications of the present invention. Compound diffractive periodic structure 136 may have a periodic structure feature size 137 of at least 100 nm and/or less than 400 nm. The large field of illumination as described hereinabove may be obtained by small sub-features that are around 300 nm. The period of compound diffractive periodic structure 136 may be tuned to provide a desired angular pitch of the projected beams of light.

Structured light projectors 22 that have compound diffractive periodic structure 136 as pattern generating optical element 38 may include laser diode 36, collimating lens 130, an aperture, and compound diffractive periodic structure 136. The aperture defines a smaller input beam diameter in order to maintain tightly focused spots at a near focal distance, e.g., at least 1 mm and/or less than 30 mm, e.g., at least 4 mm and/or less than 24 mm, from compound diffractive periodic structure 136. For some applications, the aperture is chrome film that is over the periodic structure features of compound diffractive periodic structure 136. In some applications, the aperture may span a distance of at least 10 periods of compound diffractive periodic structure 136 and has a diameter of at least 50 microns and/or less than 200 microns.

For some applications, beam shaping optical element 40 (such as is shown in FIG. 3) is a collimating lens 130 disposed between laser diode 36 and pattern generating optical element 38. With respect to the applications described hereinabove with reference to FIGS. 19A-B, 20A-E, and 21A-C, collimating lens 130 may be disposed between laser diode 36 and segmented DOE 122 (FIG. 19A), between laser diode 36 and micro-lens array 132 (FIG. 20A), and between laser diode 36 and compound diffractive periodic structure 136 (FIG. 21A).

Figure 22A:
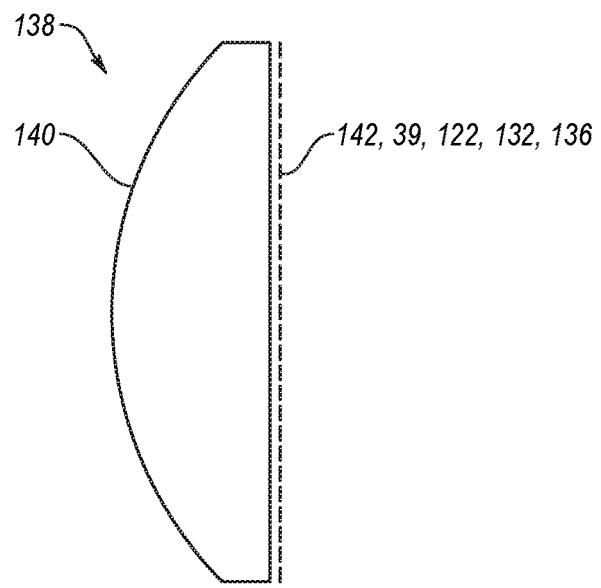
FIGS. 22A-B are schematic illustrations showing a single optical element that has an aspherical first side and a planar second side, opposite the first side, and a structured light projector including the optical element, in accordance with some applications of the present invention.
Figure 22B:
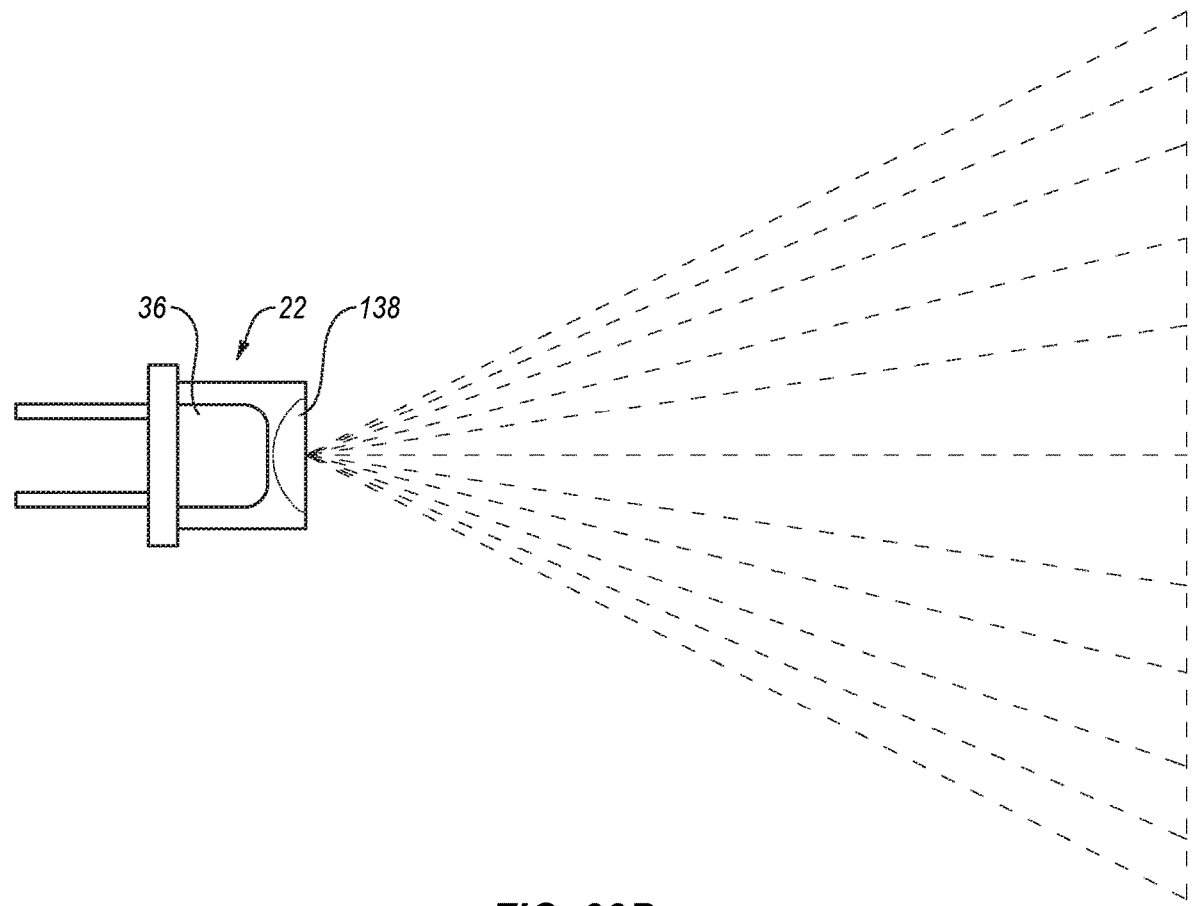

Reference is now made to FIGS. 22A-B, which are schematic illustrations showing a single optical element 138 that has an aspherical first side and a planar second side, opposite the first side, and structured light projector 22 including optical element 138, in accordance with some applications of the present invention. For some applications, collimating lens 130 and pattern generating optical element 38 may be fabricated as single optical element 138, a first aspherical side 140 of which collimates the light transmitted from laser diode 36, and a second planar side 142 of which generates distribution 34 of discrete unconnected spots 33 of light. Planar side 142 of single optical element 138 may be shaped to define DOE 39, segmented DOE 122, micro-lens array 132, or compound diffractive periodic structure 136.

Figure 23A:
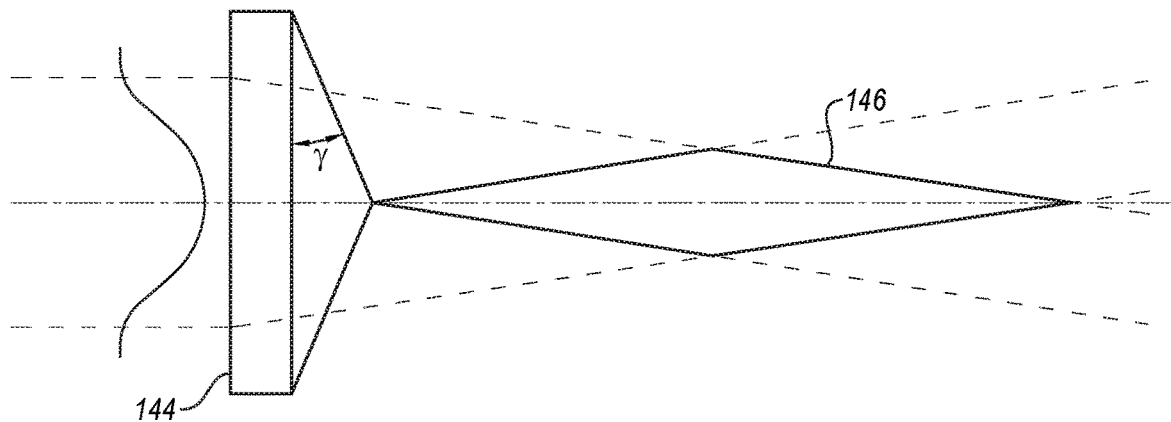
FIGS. 23A-B are schematic illustrations of an axicon lens and a structured light projector including the axicon lens, in accordance with some applications of the present invention.
Figure 23B:
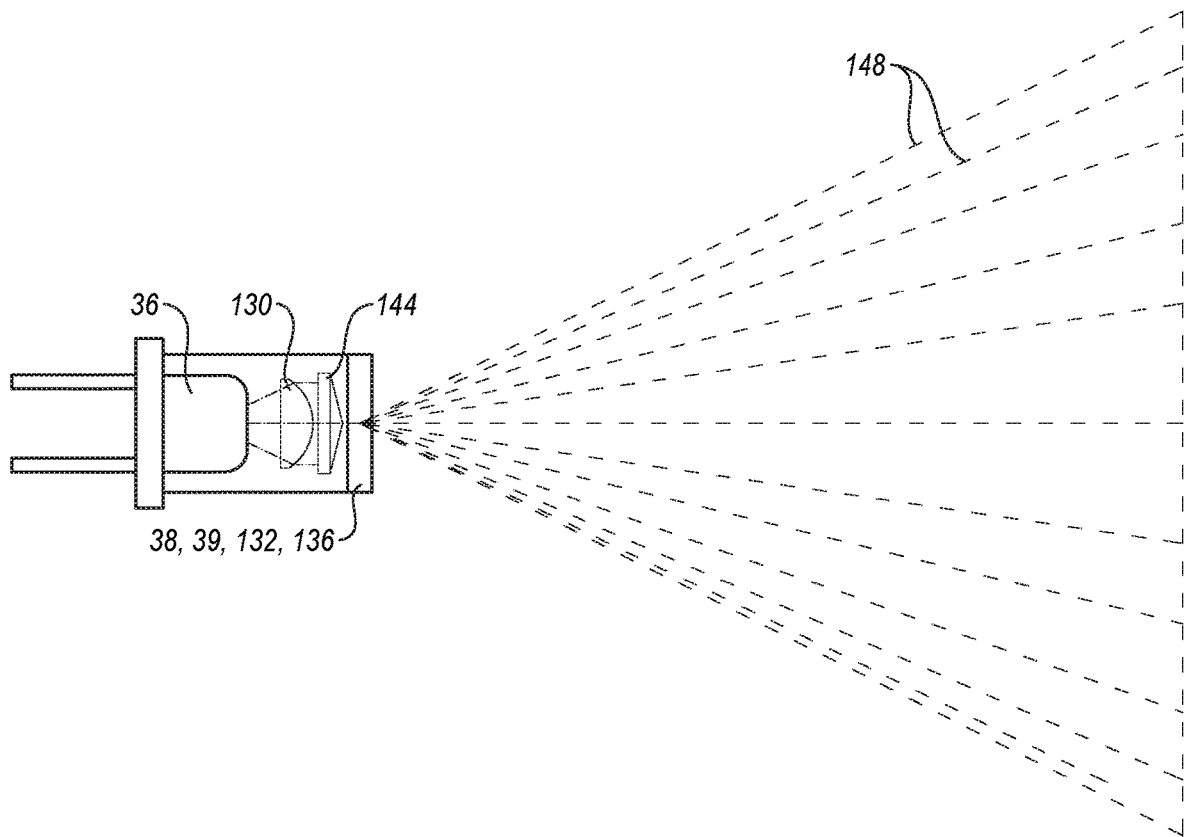

Reference is now made to FIGS. 23A-B, which are schematic illustrations of an axicon lens 144 and structured light projector 22 including axicon lens 144, in accordance with some applications of the present invention. Axicon lenses are known to generate a Bessel beam, which is a beam of light that is focused throughout a desired depth range depending on the input beam diameter and the axicon head angle. For some applications, axicon lens 144, having a head angle γ (gamma) of at least 0.2 degrees and/or less than 2 degrees, is disposed between collimating lens 130 and pattern generating optical element 38. Axicon lens 144 generates a focused Bessel beam 146 when laser diode 36 transmits light through axicon lens 144. Focused Bessel beam 146 is split into many beams 148 by pattern generating optical element 38, each beam 148 being an exact copy of the Bessel beam 146 generated by axicon lens 144. Pattern generating optical element 38 may be DOE 39, micro-lens array 132, or compound diffractive periodic structure 136.

Figure 24A:
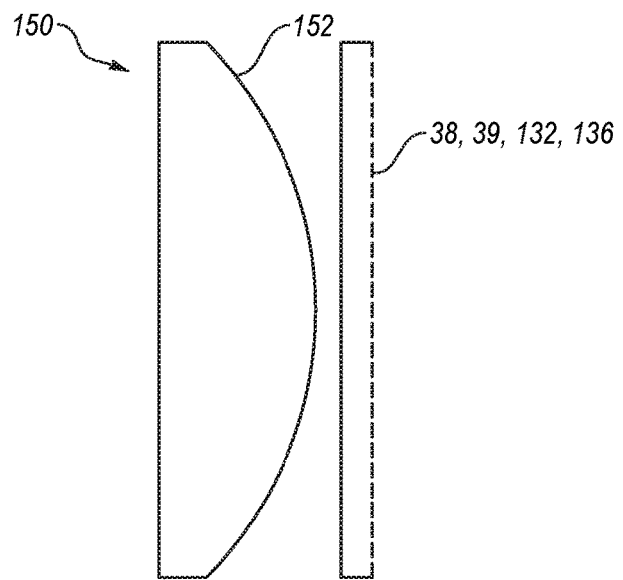
FIGS. 24A-B are schematic illustrations showing an optical element that has an aspherical surface on a first side and a planar surface on a second side, opposite the first side, and a structured light projector including the optical element, in accordance with some applications of the present invention.
Figure 24B:
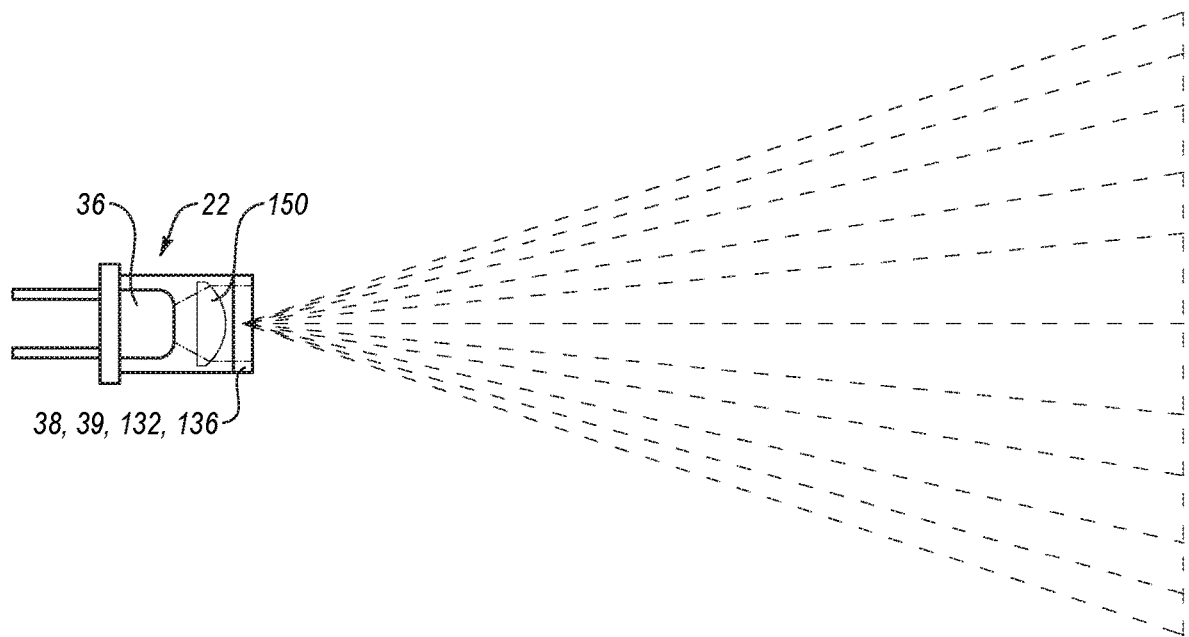

Reference is now made to FIGS. 24A-B, which are schematic illustrations showing an optical element 150 that has an aspherical surface 152 on a first side and a planar surface on a second side, opposite the first side, and structured light projector 22 including optical element 150, in accordance with some applications of the present invention. For some applications, collimating lens 130 and axicon lens 144 may be fabricated as single optical element 150. Aspherical surface 152 of single optical element 150 generates a Bessel beam directly from a diverging beam of light when laser diode 36 transmits light through optical element 150. As the light then travels through pattern generating optical element 38, distribution 34 of discrete unconnected spots 33 of light is generated such that discrete unconnected spots 33 of light have a substantially uniform size at any orthogonal plane located between 1 mm and 30 mm, e.g., between 4 mm and 24 mm, from pattern generating optical element 38. Pattern generating optical element 38 may be DOE 39, micro-lens array 132, or compound diffractive periodic structure 136. As used herein throughout the present application, including in the claims, spots having a "substantially uniform size" means that the size of the spots does not vary by more than 40%.

Figure 25:
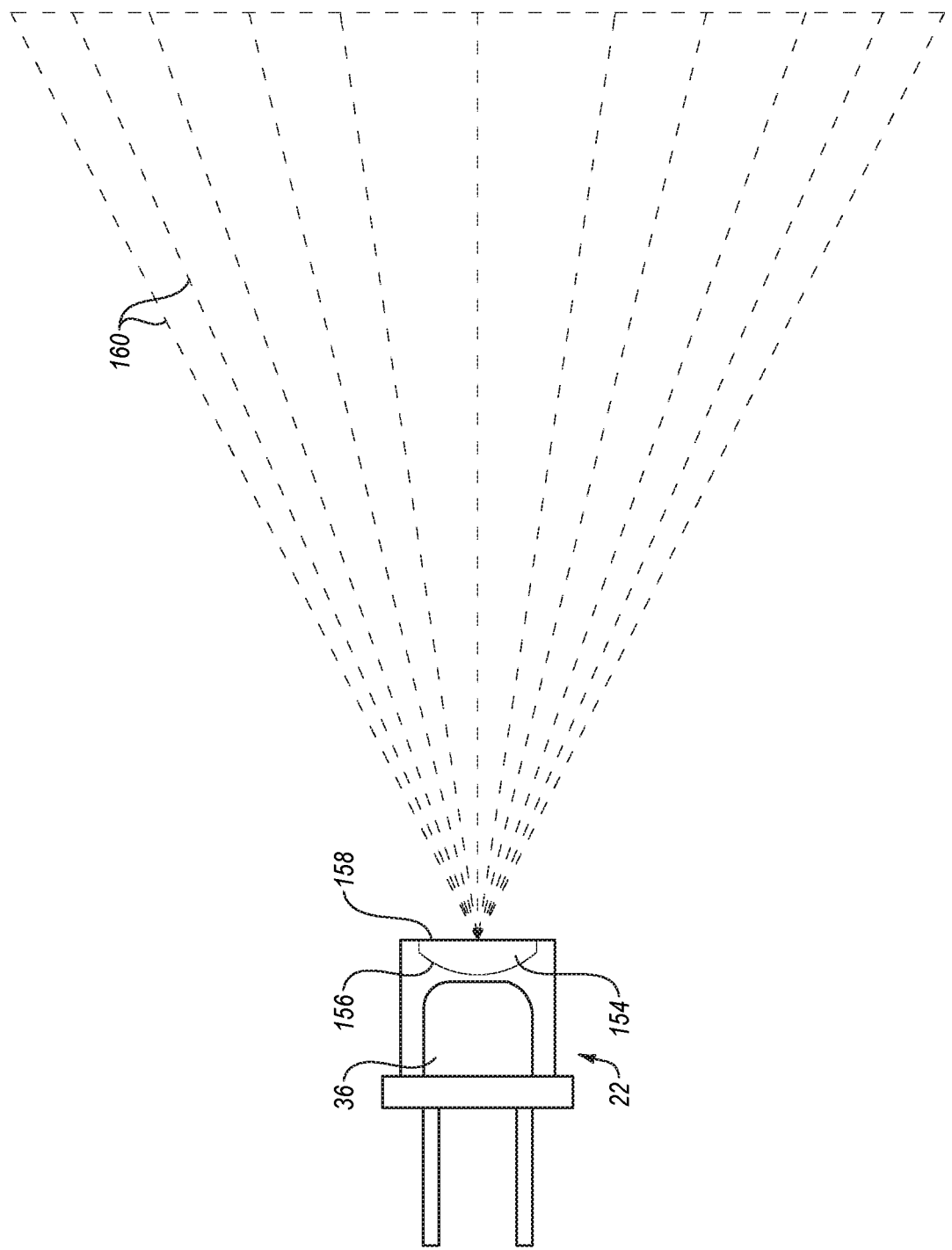
FIG. 25 is a schematic illustration of a single optical element in a structured light projector, in accordance with some applications of the present invention.

Reference is now made to FIG. 25, which is a schematic illustration of a single optical element 154 in structured light projector 22, in accordance with some applications of the present invention. For some applications, single optical element 154 may perform the functions of the collimating lens, axicon lens, and pattern generating optical element. Single optical element 154 includes an aspherical surface 156 on a first side and a planar surface 158 on a second side, opposite the first side. Aspherical surface 156 generates a Bessel beam directly from a diverging beam of light when laser diode 36 transmits a diverging beam of light through the single optical element 154. Planar surface 158 is shaped to define pattern generating optical element 38 and thus splits the Bessel beam into an array of discrete Bessel beams 160 so as to generate distribution 34 of discrete unconnected spots 33 of light, such that discrete unconnected spots 33 of light have a substantially uniform size at any orthogonal plane located between 1 mm and 30 mm, e.g., between 4 mm and 24 mm, from pattern single optical element 154. Planar surface 158 may be shaped to define DOE 39, micro-lens array 132, or compound diffractive periodic structure 136.

Figure 26A:
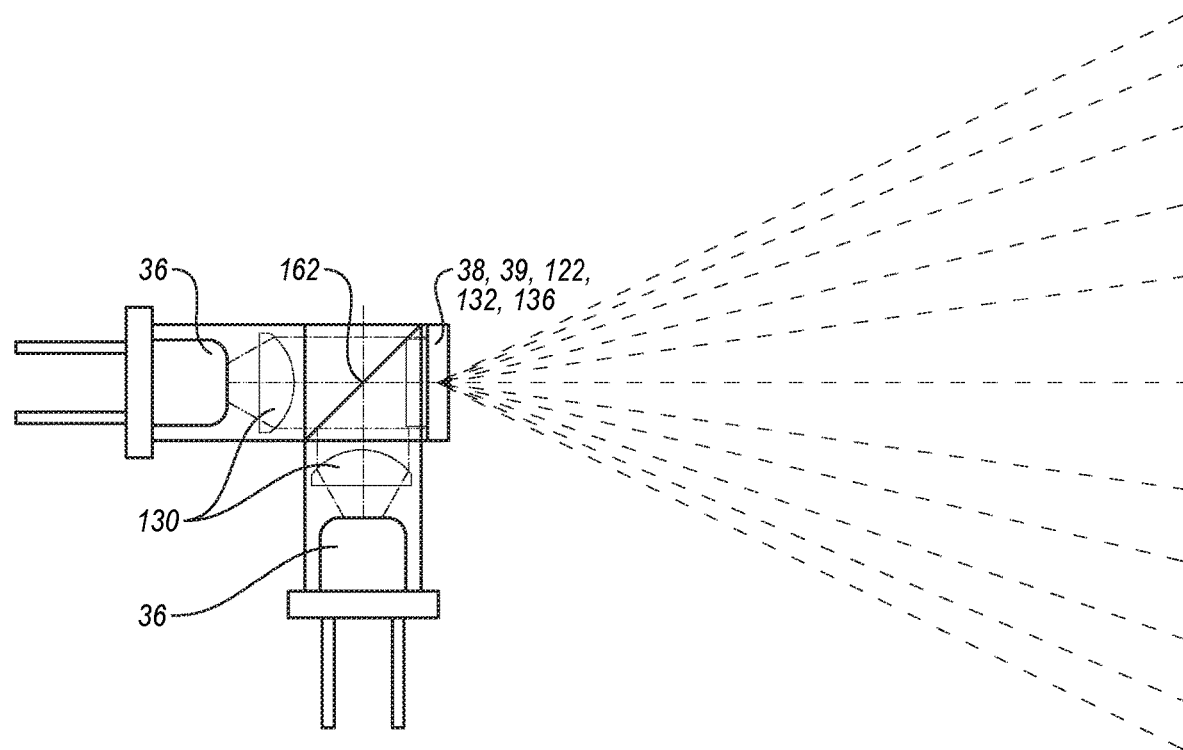
FIGS. 26A-B are schematic illustrations of a structured light projector with more than one laser diode, in accordance with some applications of the present invention.
Figure 26B:
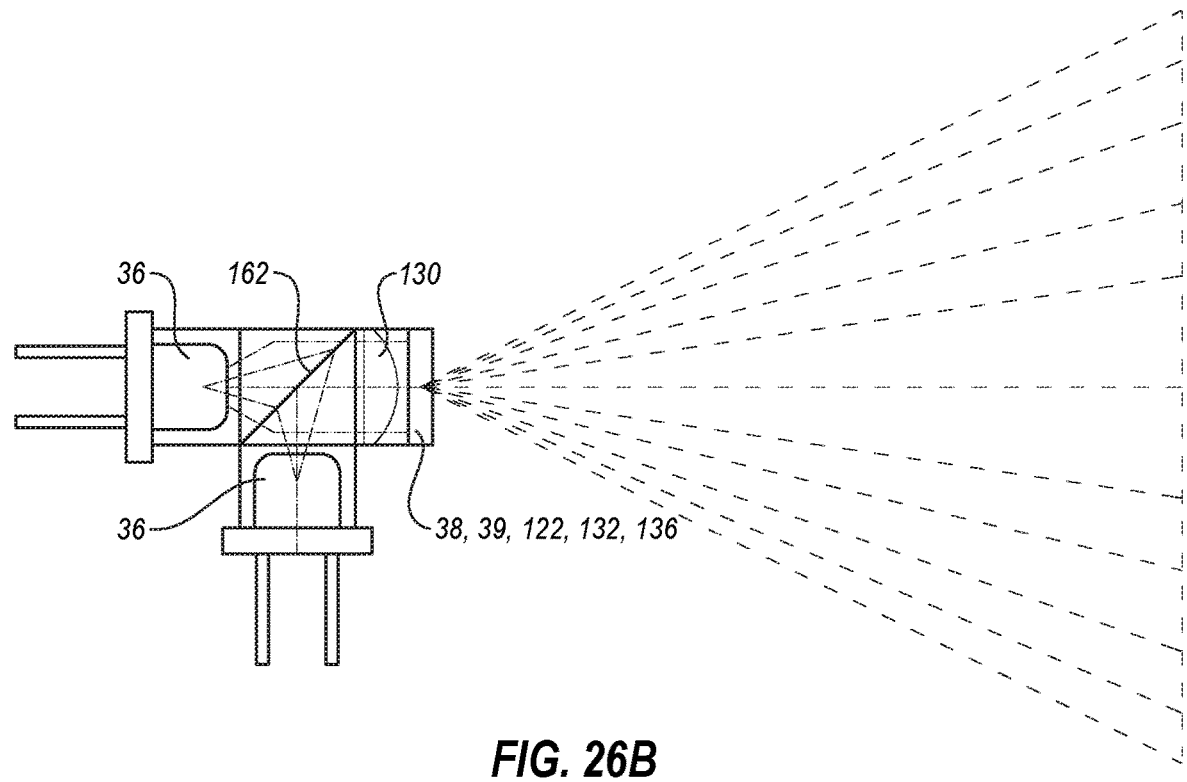

Reference is now made to FIGS. 26A-B, which are schematic illustrations of structured light projector 22 with more than one light source (e.g., laser diodes 36), in accordance with some applications of the present invention. When using a laser diode, laser speckles may give rise to spatial noise. The speckle effect is a result of interference of many waves of the same frequency but different phases and amplitudes. When all added together, the resultant wave is a wave whose amplitude varies randomly across the beam profile. For some applications, the speckle effect may be reduced by combining a plurality of laser diodes 36 of the same wavelength. Different lasers having the same wavelength are not coherent to one another, so combining them into the same spatial space, or the same diffractive beam splitter 162, will lower the speckles by at least a factor of the square root of the number of different laser diodes 36.

Beam splitter 162 may be a standard 50/50 splitter, lowering the efficiency of both beams to under 50%, or a polarizing beam splitter (PBS), keeping the efficiency at greater than 90%. For some applications, each laser diode 36 may have its own collimating lens 130, such as is shown in FIG. 26A. Alternatively, the plurality of laser diodes 36 may share a collimating lens 130, the collimating lens being disposed between beam splitter 162 and pattern generating optical element 38, such as is shown in FIG. 26B. Pattern generating optical element 38 may be DOE 39, segmented DOE 122, micro-lens array 132, or compound diffractive periodic structure 136.

As described hereinabove, a sparse distribution 34 improves capture by providing an improved balance between reducing the amount of projected light while maintaining a useful amount of information. For some applications, in order to provide a higher density pattern without reducing capture, a plurality of laser diodes 36 having different wavelengths may be combined. For example, each structured light projector 22 may include at least two, e.g., at least three, laser diodes 36 that transmit light at distinct respective wavelengths. Although projected spots 33 may be nearly overlapping in some cases, the different color spots may be resolved in space using the camera sensors' color distinguishing capabilities. Optionally, red, blue, and green laser diodes may be used. All of the structured light projector configurations described hereinabove may be implemented using a plurality of laser diodes 36 in each structured light projector 22.

Figure 27A:
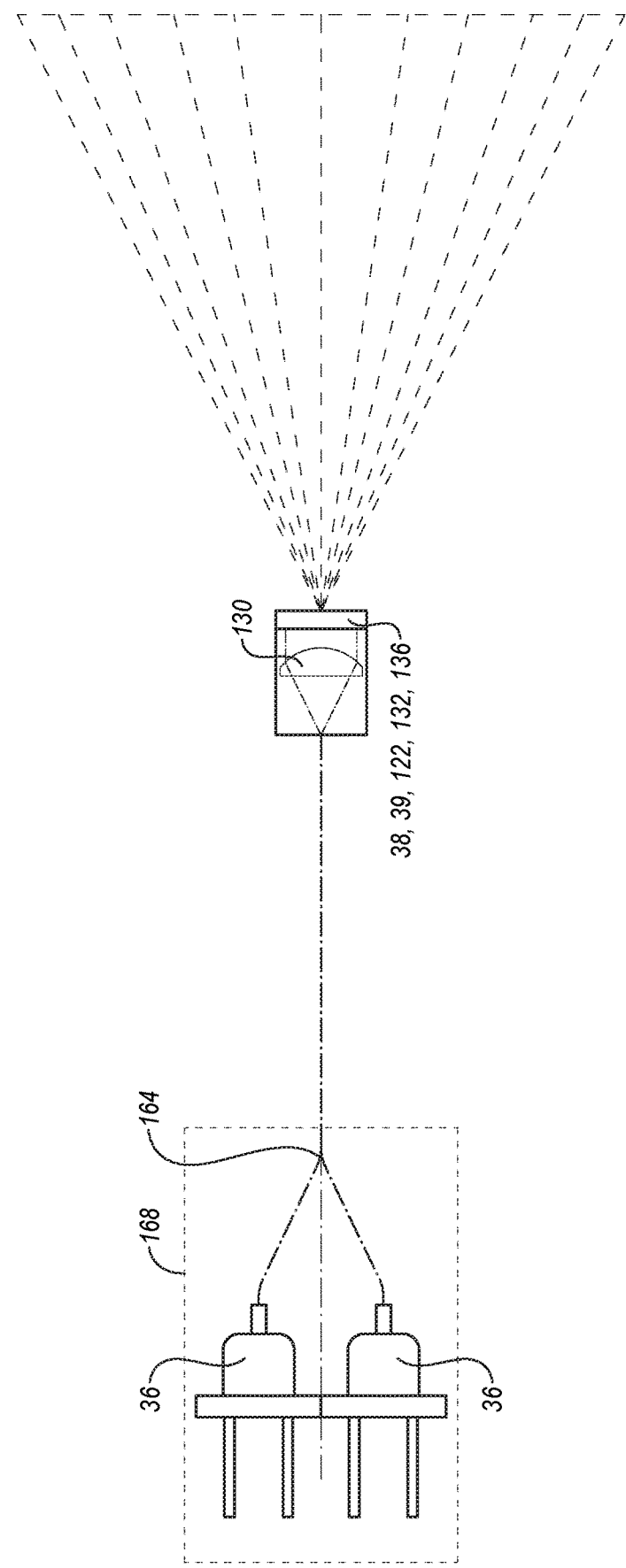
FIGS. 27A-B are schematic illustrations of different ways to combine laser diodes of different wavelengths, in accordance with some applications of the present invention.
Figure 27B:
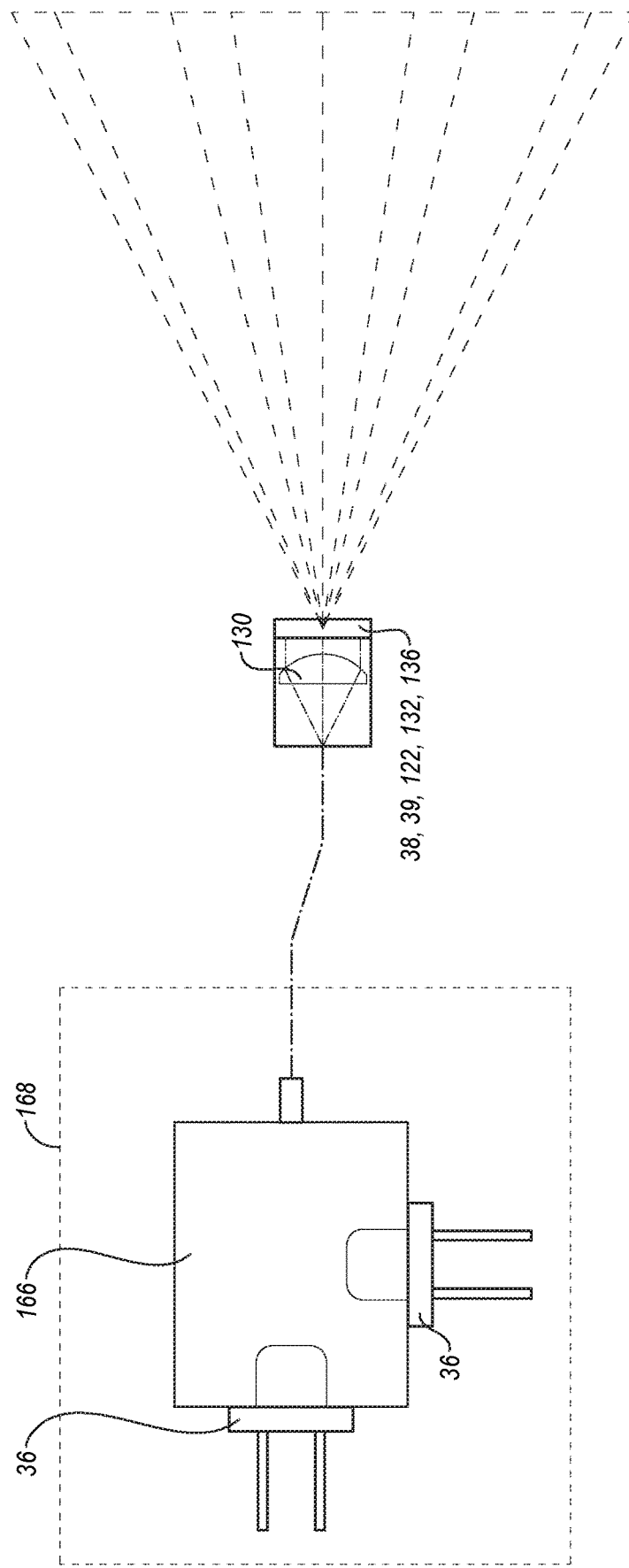

Reference is now made to FIGS. 27A-B, which are schematic illustrations of different ways to combine laser diodes of different wavelengths, in accordance with some applications of the present invention. Combining two or more lasers of different wavelengths into the same diffractive element can be done using a fiber coupler 164 (FIG. 27A) or a laser combiner 166 (FIG. 27B). For laser combiner 166 the combining element may be a dichroic two-way or three-way dichroic combiner. Within each structured light projector 22 all laser diodes 36 transmit light through a common pattern generating optical element 38, either simultaneously or at different times. The respective laser beams may hit slightly different positions in pattern generating optical element 38 and create different patterns. These patterns will not interfere with each other due to different colors, different times of pulse, or different angles. Using fiber coupler 164 or laser combiner 166 allows for laser diodes 36 to be disposed in a remote enclosure 168. Remote enclosure 168 may be disposed in a proximal end of handheld wand 20, thus allowing for a smaller probe 28.

For some applications, structured light projectors 22 and cameras 24 may be disposed in proximal end 100 of probe 28.

The following description relates predominantly to applications of the present invention that include a light field camera.

Figure 28A:
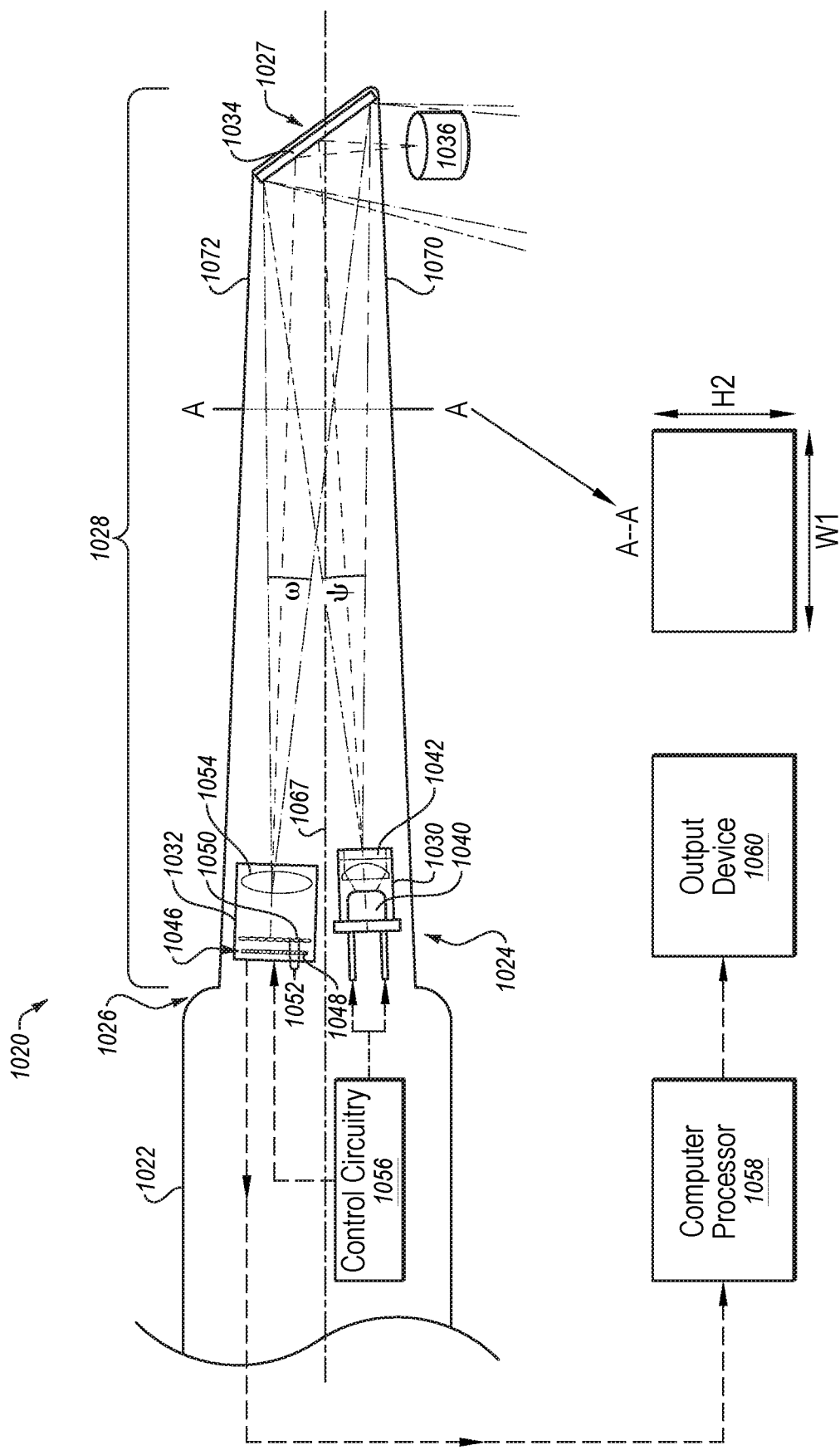
FIG. 28A is a schematic illustration of a handheld wand with a structured light projector and a light field camera disposed in a proximal end of the handheld wand, and a mirror disposed within a probe at a distal end of the handheld wand, in accordance with some applications of the present invention.
Figure 28B:
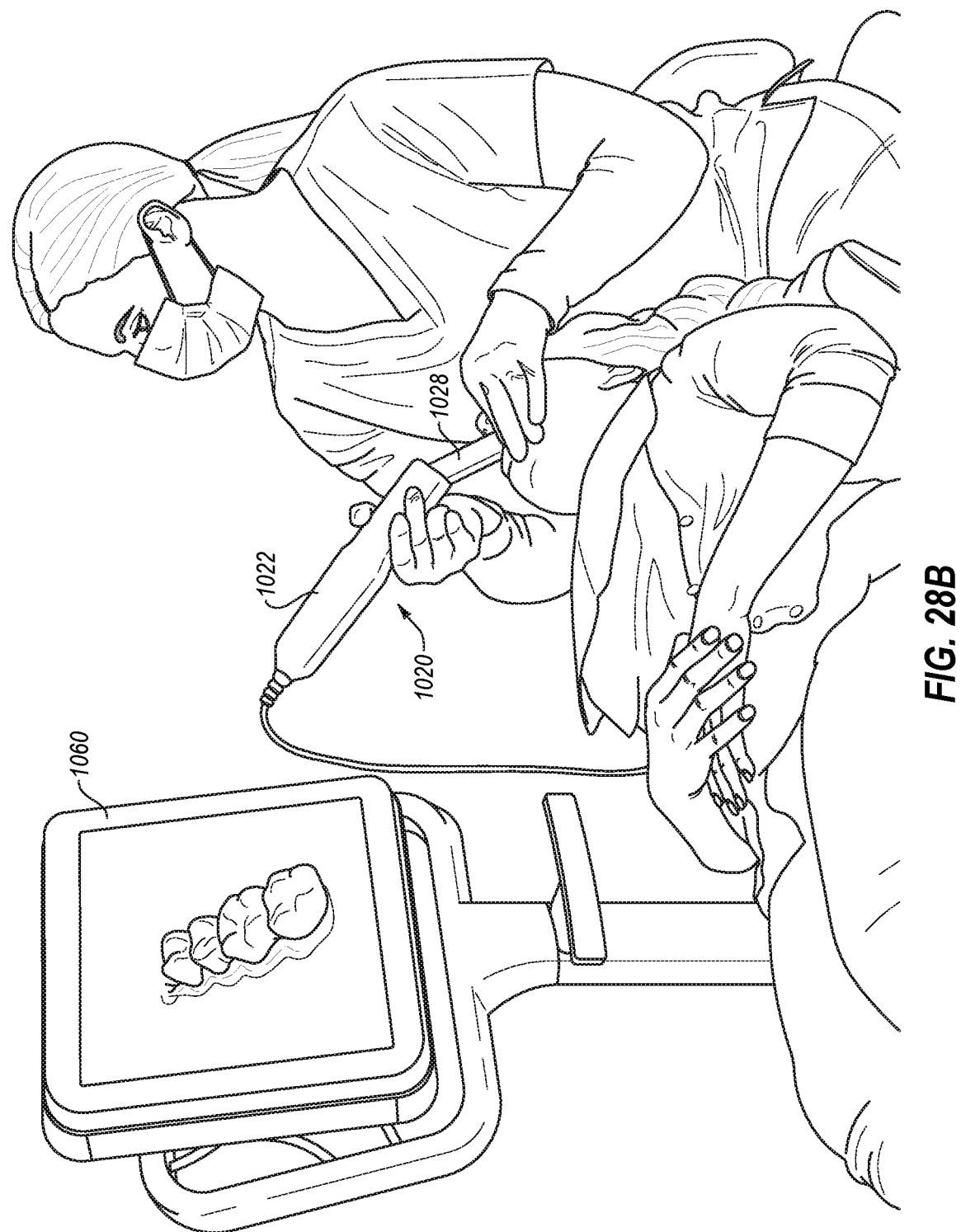
FIG. 28B is a schematic illustration of the handheld wand of FIG. 28A, with the probe shown inside a subject's mouth, in accordance with some applications of the present invention.

Reference is now made to FIG. 28A, which is a schematic illustration of an intraoral scanner 1020, in accordance with some applications of the present invention. Intraoral scanner 1020 comprises an elongate handheld wand 1022 that has a probe 1028 at distal end 1026 of handheld wand 1022. Probe 1028 has a distal end 1027 and a proximal end 1024. As used throughout the present application, including in the claims, the proximal end of the handheld wand is defined as the end of the handheld wand that is closest to a user's hand when the user is holding the handheld wand in a ready-for-use position, and the distal end of the handheld wand is defined as the end of the handheld wand that is farthest from the user's hand when the user is holding the handheld wand in a ready-for-use position.

For some applications, a single structured light projector 1030 is disposed in proximal end 1024 of probe 1028, a single light field camera 1032 is disposed in proximal end 1024 of probe 1028, and a mirror 1034 is disposed in distal end 1027 of probe 1028. Structured light projector 1030 and light field camera 1032 are positioned to face mirror 1034, and mirror 1034 is positioned to reflect light from structured light projector 1030 directly onto an object 1036 being scanned and reflect light from object 1036 being scanned into light field camera 1032.

Figure 29A:
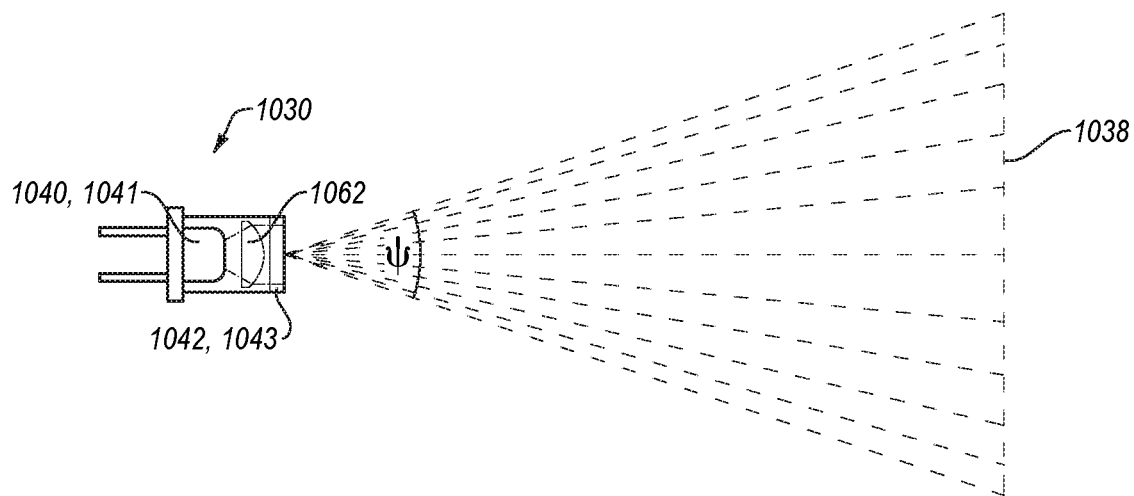
FIGS. 29A-B are schematic illustrations of structured light projectors, in accordance with some applications of the present invention.
Figure 29B:
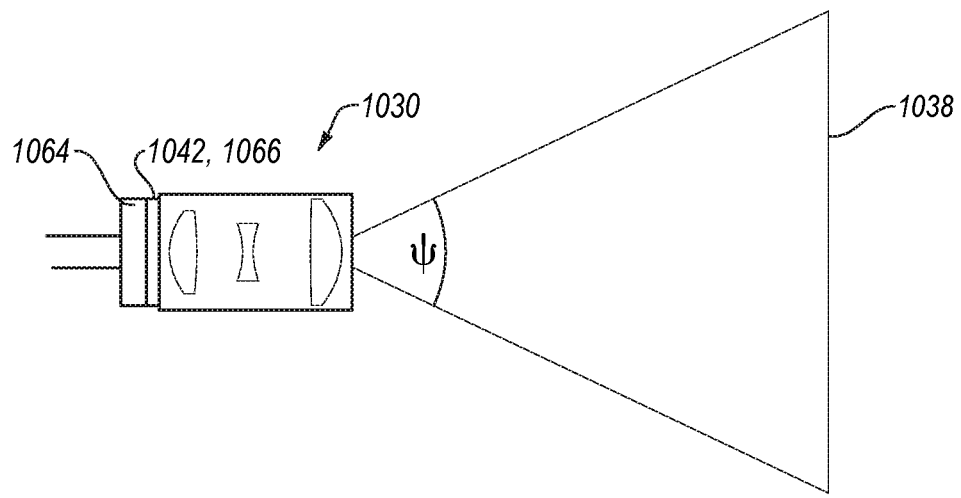

Structured light projector 1030 includes a light source 1040. In some applications, structured light projector 1030 may have a field of illumination $\psi$ (psi) of at least 6 degrees and/or less than 30 degrees. In some applications, structured light projector 1030 focuses light from light source 1040 at a projector focal plane 1038 (such as is shown in FIGS. 29A-B) that may be located at least 30 mm and/or less than 140 mm from light source 1040. Structured light projector 1030 may have a pattern generator 1042 that is disposed in the optical path between light source 1040 and projector focal plane 1038. Pattern generator 1042 generates a structured light pattern at projector focal plane 1038 when light source 1040 is activated to transmit light through pattern generator 1042.

Figure 30:
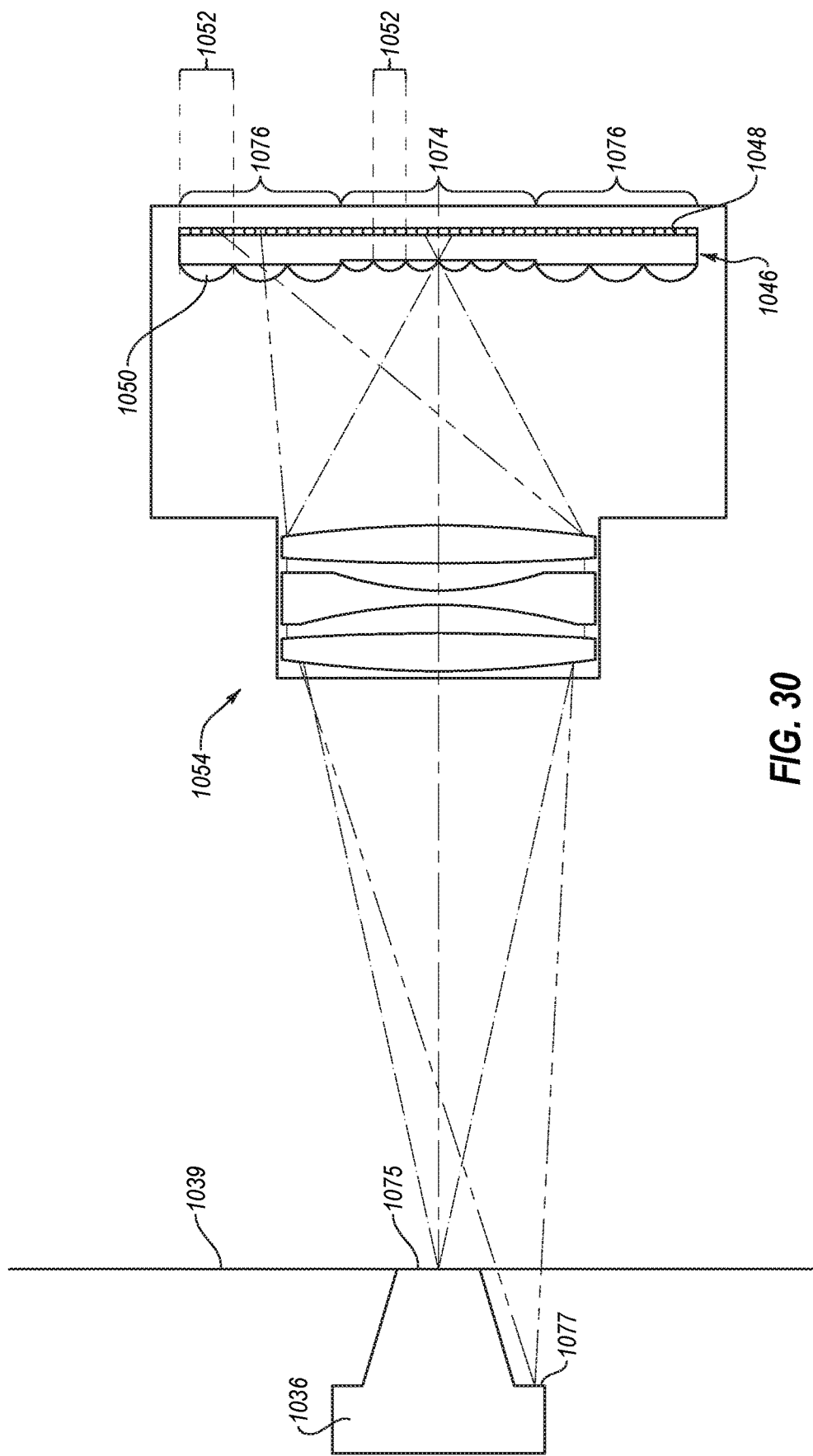
FIG. 30 is a schematic illustration of a light field camera and a three-dimensional object being captured, in accordance with some applications of the present invention.

Light field camera 1032 may have a field of view $\omega$ (omega) of at least 6 degrees and/or less than 30 degrees. Light field camera 1032 may focus at a camera focal plane 1039 (such as is shown in FIG. 30) that may be located at least 30 mm and/or less than 140 mm from light field camera 1032. Light field camera 1032 has a light field camera sensor 1046 that comprises an image sensor 1048 comprising an array of pixels, e.g., a CMOS image sensor, and an array of micro-lenses 1050 disposed in front of image sensor 1048 such that each micro-lens 1050 is disposed over a sub-array 1052 of sensor pixels. Light field camera 1032 additionally has an objective lens 1054 disposed in front of light field camera sensor 1048 that forms an image of object 1036 being scanned onto light field camera sensor 1046.

Figure 31:
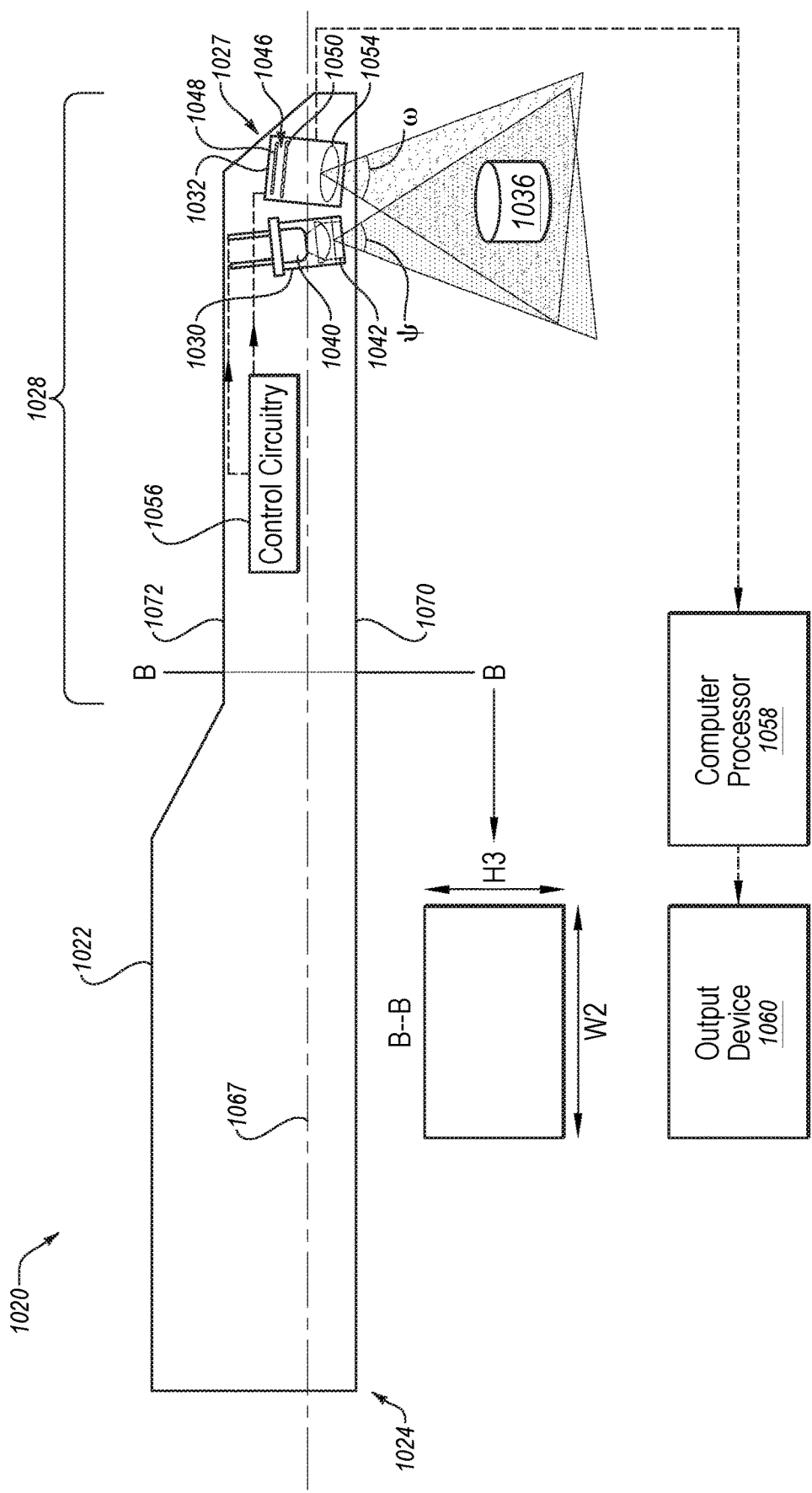
FIG. 31 is a schematic illustration of a handheld wand with a structured light projector and a light field camera disposed within a probe at the distal end of the handheld wand, in accordance with some applications of the present invention.
Figure 32:
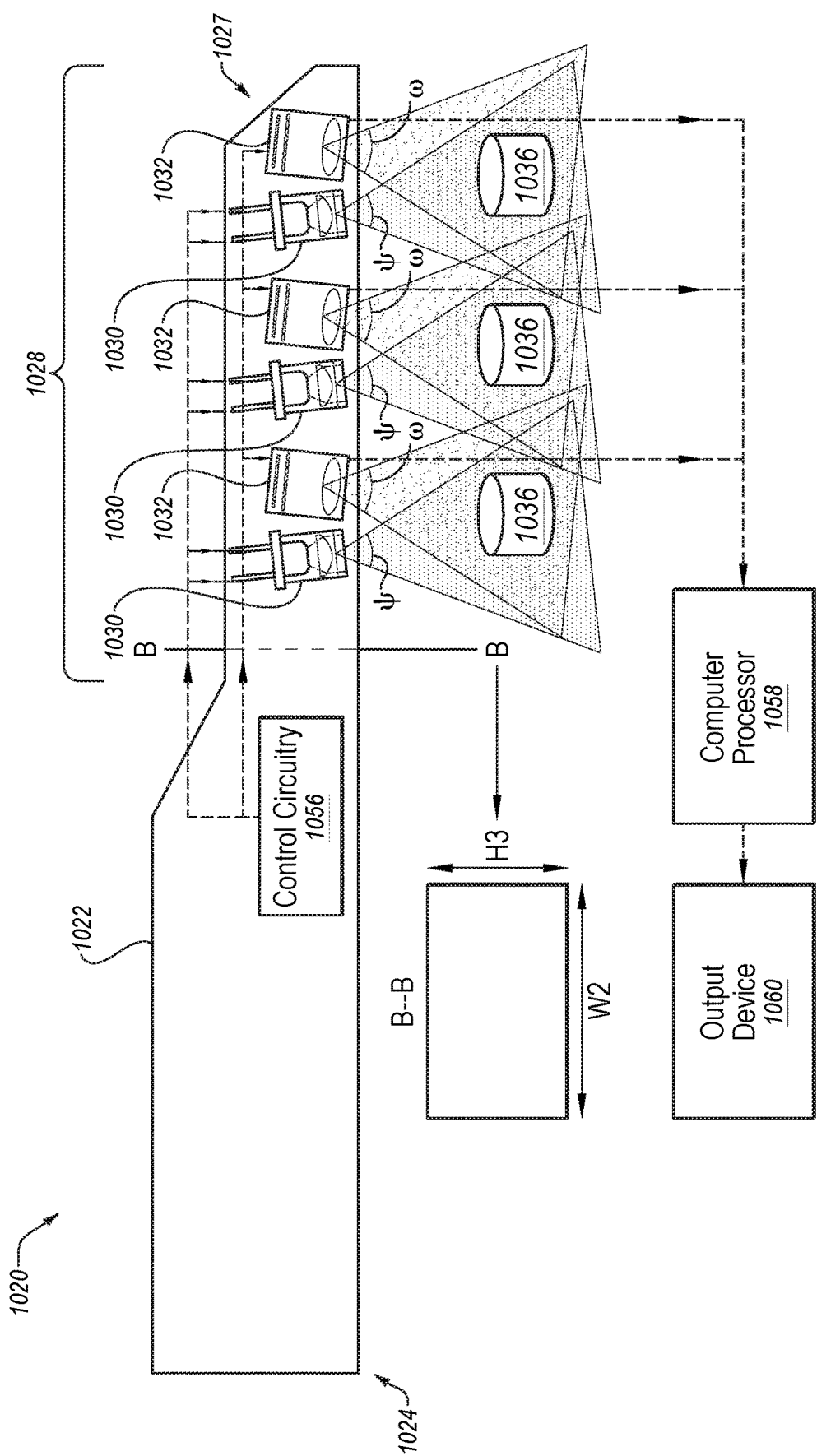
FIG. 32 is a schematic illustration of the handheld wand with a plurality of structured light projectors and light field cameras disposed within the probe at the distal end of the handheld wand, in accordance with some applications of the present invention.

Intraoral scanner 1020 may include control circuitry 1056 that (a) drives structured light projector 1030 to project a structured light pattern onto object 1036 outside handheld wand 1022, and (b) drives light field camera 1032 to capture a light field that results from the structured light pattern reflecting off object 1036. The structured light field contains information about the intensity of the structured light pattern reflecting off object 1036 and the direction of the light rays. The light field also contains information about phase-encoded depth via which the scene depth can be estimated from different directions. Using information from the captured light field, a computer processor 1058 may reconstruct a 3-dimensional image of the surface of object 1036, and may output the image to an output device 1060, e.g., a monitor. It is noted that computer processor 1058 is shown in FIGS. 28A, 31, and 32, by way of illustration and not limitation, to be outside of handheld wand 1022. For other applications, computer processor 1058 may be disposed within handheld wand 1022.

In some applications, object 1036 being scanned is at least one tooth inside a subject's mouth. As described hereinabove, dentists frequently coat a subject's teeth with an opaque powder in order to improve image capture when using a digital intraoral scanner. Light field camera 1032 in intraoral scanner 1020 may capture the light field from the structured light pattern reflecting off the tooth without the presence of such a powder on the tooth, enabling a simpler digital intraoral scanning experience.

When structured light projector 1030 and light field camera 1032 are disposed in proximal end 1024 of probe 1028, the size of probe 1028 is limited by the angle at which mirror 1034 is placed. In some applications, a height H2 of probe 1028 is less than 17 mm, and a width W1 of probe 1028 is less than 22 mm, height H2 and width W1 defining a plane that is perpendicular to a longitudinal axis 1067 of handheld wand 1022. Furthermore, height H2 of probe 1028 is measured from a lower surface 1070 (scanning surface), through which reflected light from object 1036 being scanned enters probe 1028, to an upper surface 1072 opposite lower surface 1070. In some applications, height H2 is between 14-17 mm. In some applications, width W1 is between 18-22 mm.

Reference is now made to FIG. 29A, which is a schematic illustration of structured light projector 1030 having a laser diode 1041 as light source 1040, in accordance with some applications of the present invention. For some applications, pattern generator 1042 may be a diffractive optical element (DOE) 1043. Laser diode 1041 may transmit light through a collimator 1062, and the collimated light is then transmitted through DOE 1043 in order to generate the structured light pattern as a distribution of discrete unconnected spots of light. Alternatively to DOE 1043, pattern generator 1042 may be a refractive micro-lens array disposed in the optical path between laser diode 1041 and the projector focal plane (configuration not shown).

Reference is now made to FIG. 29B, which is a schematic illustration of structured light projector 1030 having a light emitting diode (LED) 1064 as light source 1040, and a mask 1066 as pattern generator 1042.

Reference is now made to FIG. 30, which is a schematic illustration of light field camera 1032, showing light field camera sensor 1046, and a three-dimensional object 1036 being captured, in accordance with some applications of the present invention. For some applications, optical parameters of light field camera 1032 may be chosen such that (a) light reflected off a foreground 1075 of object 1036 is focused onto a central region 1074 of light field camera sensor, and (b) light reflected off a background 1077 of object 1036 is focused onto a peripheral region 1076 of light field camera sensor 1046. In some applications, when scanning an intraoral scene, peripheral region 1076 may be directed toward farther objects, such as gingiva, more frequently than nearer objects, such as teeth.

Central region 1074 of light field camera sensor 1046 may have a higher spatial resolution than peripheral region 1076 of light field camera sensor 1046. For example, each one of sub-arrays 1052 in central region 1074 of image sensor 1048 may have 10-40% fewer pixels than each one of sub-arrays 1052 in peripheral region 1076, i.e., the micro-lenses in central region 1074 may be smaller than the micro-lenses in peripheral region 1076. Smaller micro-lenses allow for more micro-lenses per unit area in central region 1074. Thus, central region 1074 of light field camera sensor 1046 may have a higher spatial resolution due to the increased ratio of micro-lenses per unit area. In some applications, central region 1074 may include at least 50% of the total number of sensor pixels.

While central region 1074 has higher spatial resolution than peripheral region 1076, peripheral region 1076 may have a higher depth resolution than central region 1074, and may be set to focus at farther object distances than in central region 1074. The larger micro-lenses in peripheral region 1076 of light field camera sensor 1046 are configured to focus at a higher depth than the smaller micro-lenses in central region 1074. For example, each micro-lens 1050 disposed over a sub-array 1052 of sensor pixels in peripheral region 1076 of the image sensor 1048 may be configured to focus at a depth that is 1.1-1.4 times larger than a depth at which each micro-lens 1050 disposed over a sub-array 1052 of sensor pixels in central region 1074 of image sensor 1048 is configured to focus.

Thus, the higher spatial resolution of central region 1074 may allow foreground 1075 of object 1036 to be captured at a higher spatial resolution than background 1077 of object 1036, e.g., when scanning an intraoral scene of a subject, the teeth may be captured at a higher spatial resolution than areas surrounding the teeth, while the farther focus and higher depth resolution of peripheral region 1076 may allow for the capture of background 1077, e.g., edentulous regions and gingiva surrounding the teeth in foreground 1075.

Reference is now made to FIG. 31, which is a schematic illustration of intraoral scanner 1020 with structured light projector 1030 and light field camera 1032 disposed in distal end 1027 of probe 1028, in accordance with some applications of the present invention. For some applications, exactly one structured light projector 1030 and exactly one light field camera 1032 are disposed in distal end 1027 of probe 1028. Structured light projector 1030 may be positioned to directly face an object 1036 outside handheld wand 1022 placed in its field of illumination. Thus, light projected from structured light projector 1030 will fall on object 1036 without any optical redirection, e.g., reflection off a mirror in order to redirect the light such as described hereinabove with reference to FIG. 28A. Similarly, light field camera 1032 may be positioned to directly face object 1036 outside handheld wand 1022 placed in its field of view. Thus, light reflecting off object 1036 will enter light field camera 1032 without any optical redirection, e.g., reflection off a mirror in order to redirect the light such as described hereinabove with reference to FIG. 28A.

Positioning structured light projector 1030 in distal end 1027 of probe 1028 may allow field of illumination $\psi$ (psi) of structured light projector 1030 to be wider, e.g., at least 60 degrees and/or less than 120 degrees. Positioning structured light projector 1030 in distal end 1027 of probe 1028 may also allow structured light projector 1030 to focus light from light source 1040 at a projector focal plane that may be located at least 3 mm and/or less than 40 mm from light source 1040.

Positioning light field camera 1032 in distal end 1027 of probe 1028 may allow field of view $\omega$ (omega) of light field camera 1032 to be wider, e.g., at least 60 degrees and/or less than 120 degrees. Positioning light field camera 1032 in distal end 1027 of probe 1028 may also allow light field camera 1032 to focus at a camera focal plane that may be located at least 3 mm and/or less than 40 mm from light source 1040. In some applications, field of illumination $\psi$ (psi) of structured light projector 1030 and field of view $\omega$ (omega) of light field camera 1032 overlap such that at least 40% of the projected structured light pattern from structured light projector 1030 is in field of view $\omega$ (omega) of light field camera 1032. Similarly to as described hereinabove with reference to FIG. 30, when intraoral scanner 1020 has a single light field camera 1032 disposed in distal end 1027 of probe 1028, optical parameters of light field camera sensor 1046 may be chosen such that a central region of light field camera sensor 1090 has a higher resolution than a peripheral region of light field camera sensor 1046.

Positioning structured light projector 1030 and light field camera 1032 in distal end 1027 of probe 1028 may enable probe 1028 to be smaller since mirror 1034 is not used in this configuration. In some applications, height H3 of probe 1028 is less than 14 mm, and width W2 of probe 1028 is less than 22 mm, height H3 and width W2 defining a plane that is perpendicular to a longitudinal axis 1067 of handheld wand 1022. In some applications, height H3 is between 10-14 mm. In some applications, width W2 is between 18-22 mm. As described hereinabove, height H3 of probe 1028 is measured from (a) a lower surface 1070 (scanning surface), through which reflected light from object 1036 being scanned enters probe 1028, to (b) an upper surface 1072 opposite lower surface 1070. Control circuitry 1056 (a) may drive structured light projector 1030 to project a structured light pattern onto object 1036 outside handheld wand 1022, and (b) may drive light field camera 1032 to capture a light field resulting from the structured light pattern reflecting off object 1036. Using information from the captured light field, computer processor 1058 may reconstruct a 3-dimensional image of the surface of objects 1036, and output the image to an output device 1060, e.g., a monitor.

Reference is now made to FIG. 32, which is a schematic illustration of intraoral scanner 1020 with a plurality of structured light projectors 1030 and a plurality of light field cameras 1032 disposed in distal end 1027 of probe 1028, in accordance with some applications of the present invention. Having a plurality of structured light projectors and a plurality of light field cameras may increase a general field of view of intraoral scanner 1020, which may enable capturing a plurality of objects 1036, e.g., capturing a plurality of teeth as well as regions around the teeth, e.g., edentulous regions in a subject's mouth. In some applications, a plurality of fields of illumination ψ (psi) overlap with a respective plurality of fields of view ω (omega), such that at least 40% of the projected structured light pattern from each structured light projector 1030 is in a field of view ω (omega) of at least one light field camera 1032. Control circuitry 1056 (a) may drive the plurality of structured light projectors 1030 to each project a structured light pattern onto object 1036 outside handheld wand 1022, and (b) may drive the plurality of light field cameras 1032 to capture a light field resulting from the plurality of structured light patterns reflecting off object 1036. Using information from the captured light field, computer processor 1058 may reconstruct a 3-dimensional image of the surface of objects 1036, and output the image to an output device 1060, e.g., a monitor.

For some applications, at least one of structured light projectors 1030 may be a monochrome structured light projector that projects a monochrome structured light pattern onto object 1036 being scanned. For example, the monochrome structured light projector may project a blue structured light pattern at a wavelength of 420-470 nm. At least one of light field cameras 1032 may be a monochrome light field camera that captures a light field resulting from the monochrome structured light pattern reflecting off object 1036 being scanned. Intraoral scanner 1020 may further include a light source that transmits white light onto object 1036 and a camera that captures a 2-dimensional color image of object 1036 under the white light illumination. Computer processor 1058 may combine (a) information captured from the monochrome light field with (b) at least one 2-dimensional color image of object 1036 in order to reconstruct a 3-dimensional image of the surface of objects 1036. Computer processor 1058 may then output the image to an output device 1060, e.g., a monitor.

Any of the aforementioned apparatuses may be used to perform methods of generating image data (e.g., of an intraoral surface. In one example implementation, a method includes generating, by one or more light projectors disposed in a probe of an intraoral scanner, respective light patterns. Generating a light pattern by a light projector of the one or more light projectors may include generating light by a light projector, focusing the light at a projector focal plane, and generating, by a pattern generator, a light pattern from the light at the projector focal plane. The method may further include projecting the respective light patterns of the one or more light projectors toward an intraoral surface disposed in a field of illumination of the one or more light projectors. The method may further include receiving, by one or more light field cameras disposed in the probe, a light field resulting from at least a portion of the respective light patterns reflecting off of the intraoral surface. The method may further include generating a plurality of images by the one or more light field cameras that depict the light field, and sending the plurality of images to a data processing system.

In some implementations, the one or more light projectors and the one or more light field cameras are disposed in a distal end of the probe, and the one or more light projectors and the one or more light field cameras are positioned such that (a) each light projector directly faces the intraoral surface, (b) each light field camera directly faces the intraoral surface, and (c) at least 40% of the light pattern from each light projector is in a field of view of at least one of the light field cameras.

In some implementations, the one or more light projectors and the light field camera are disposed in a proximal end of the probe. For such implementations the method may further include using a mirror to reflect the respective light patterns onto the intraoral surface, and using the mirror to reflect the light field reflected from the intraoral surface into the one or more light field cameras.

In some applications of the invention, a method may be performed by any of the described apparatuses for intraoral scanning (e.g., intraoral scanners and/or data processing systems such as computer processor 1058) to generate a digital three-dimensional model of an intraoral surface. In one embodiment, the method includes driving one or more light projectors of an intraoral scanner to project a light pattern on the intraoral surface. The method further includes driving one or more light field cameras of the intraoral scanner to capture a plurality of images that depict a light field resulting from at least a portion of the projected light pattern reflecting off of the intraoral surface, wherein the light field contains information about an intensity of the light pattern reflecting off of the intraoral surface and a direction of light rays. The method further includes receiving the plurality of images that depict at least a portion of a projected light pattern on the intraoral surface and using information from the captured light field depicted in the plurality of images to generate the digital three-dimensional model of the intraoral surface.

In one application, at least 40% of the light pattern from each light projector is in a field of view of at least one of the one or more light field cameras. In one application, each light projector is a structured light projector that has a field of illumination of 60-120 degrees, and wherein the projector focal plane is located between 3 mm and 40 mm from the light source. In one application, each light field camera has a field of view of 60-120 degrees and is configured to focus at a camera focal plane that is located between 3 mm and 40 mm from the light field camera. In one application, the plurality of images comprise images from a plurality of light field cameras. In one application, the light field further contains information about phase-encoded depth via which depth can be estimated from different directions. In one application, the method further includes receiving a plurality of two-dimensional color images of the intraoral surface, and determining color data for the digital three-dimensional model of the intraoral surface based on the plurality of two-dimensional color images.

Applications of the invention described herein can take the form of a computer program product accessible from a computer-usable or computer-readable medium (e.g., a non-transitory computer-readable medium) providing program code for use by or in connection with a computer or any instruction execution system, such as processor 96 or processor 1058. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. In some applications, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., processor 96, or processor 1058) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the applications of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., processor 96 or processor 1058) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Processor 96 and processor 1058 are typically hardware devices programmed with computer program instructions to produce respective special purpose computers. For example, when programmed to perform the methods described herein, the computer processor typically acts as a special purpose 3-D surface reconstruction computer processor. Typically, the operations described herein that are performed by computer processors transform the physical state of a memory, which is a real physical article, to have a different magnetic polarity, electrical charge, or the like depending on the technology of the memory that is used.

Alternatively, processor 96 may take the form of a field programmable gate array (FPGA), an application-specific integrated circuit (ASIC), or a neural network implemented on a specialized chip.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for intraoral scanning, the apparatus comprising:
    an elongate handheld wand comprising a probe at a distal end of the elongate handheld wand, the probe having a proximal end and a distal end;
    one or more light projectors disposed in the distal end of the probe, each light projector of the one or more light projectors comprising:
        a light source, the light projector being configured to focus light from the light source at a projector focal plane; and
        a pattern generator disposed in an optical path between the light source and the projector focal plane, the pattern generator configured to generate a light pattern at the projector focal plane when the light source is activated to transmit light through the pattern generator;
    one or more light field cameras disposed in the distal end of the probe and configured to capture a light field that contains information about an intensity of the light pattern reflecting off of an intraoral surface and a direction of light rays, each light field camera comprising:
        a light field camera sensor, the light field camera sensor comprising (i) an image sensor comprising an array of sensor pixels, and (ii) an array of micro-lenses disposed in front of the image sensor such that each micro-lens is disposed over a sub-array of the array of sensor pixels, wherein the light field camera sensor comprises a central region having a first spatial resolution and a peripheral region having a second spatial resolution that is lower than the first spatial resolution; and
        an objective lens disposed in front of the light field camera sensor and configured to form an image of an object being scanned onto the light field camera sensor;
    wherein the one or more light projectors and the one or more light field cameras are positioned such that (a) each light projector directly faces an object outside of the elongate handheld wand placed in its field of illumination, (b) each camera directly faces the object outside of the elongate handheld wand placed in its field of view, and (c) at least 40% of the light pattern from each projector is in the field of view of at least one of the one or more light field cameras.

2. The apparatus according to claim 1, wherein the light source comprises a laser diode.

3. The apparatus according to claim 1, wherein the pattern generator comprises a diffractive optical element (DOE) configured to generate the light pattern as a distribution of discrete unconnected spots of light.

4. The apparatus according to claim 1, wherein each light projector is a structured light projector that has a field of illumination of 60-120 degrees, and wherein the projector focal plane is located between 3 mm and 40 mm from the light source.

5. The apparatus according to claim 1, wherein each light field camera has a field of view of 60-120 degrees and is configured to focus at a camera focal plane that is located between 3 mm and 40 mm from the light field camera.

6. The apparatus according to claim 1, wherein the light source comprises a light emitting diode (LED), and the pattern generator comprises a mask.

7. The apparatus according to claim 1, wherein a height of the probe is 10-14 mm and a width of the probe is 18-22 mm, the height and width defining a plane that is perpendicular to a longitudinal axis of the elongate handheld wand, wherein light enters the probe through a lower surface of the probe and the height of the probe is measured from the lower surface of the probe to an upper surface of the probe opposite the lower surface.

8. The apparatus according to claim 1, wherein the one or more light projectors are a plurality of structured light projectors, and the one or more light field cameras are a plurality of light field cameras.

9. The apparatus according to claim 1, wherein the apparatus is configured for use with an output device, the apparatus further comprising:
control circuitry configured to:
(a) drive each of the one or more light projectors to project a structured light pattern onto an intraoral object outside the elongate handheld wand,
(b) drive the one or more light field cameras to capture a light field resulting from the structured light patterns reflecting off the intraoral object, the light field comprising (i) an intensity of the structured light pattern reflecting off of the intraoral object, (ii) a direction of light rays; and
at least one computer processor configured to, based on a captured light field, reconstruct a 3-dimensional image of a surface of the intraoral object being scanned, and output the 3-dimensional image to the output device.

10. The apparatus according to claim 1:
wherein at least one of the one or more light projectors is a monochrome structured light projector configured to project a monochrome structured light pattern onto the object being scanned,
wherein at least one of the one or more light field cameras is a monochrome light field camera configured to capture a light field resulting from the monochrome structured light pattern reflecting off the object being scanned, and
further comprising (a) a light source configured to transmit white light onto the object being scanned, and (b) a camera configured to capture a 2-dimensional color image of the object being scanned.

11. The apparatus according to claim 1, wherein the pattern generator of each of the one or more light projectors is configured to generate a distribution of discrete unconnected spots of light at all planes located between 4 mm and 24 mm from the pattern generator when the light source is activated to transmit light through the pattern generator.

12. The apparatus according to claim 1, further comprising:
at least one uniform light projector, configured to project white light onto an object being scanned, wherein at least one of the one or more light field cameras is configured to capture 2-dimensional color images of the object using illumination from the uniform light projector.

13. The apparatus according to claim 1, wherein the pattern generator is configured to generate a distribution of discrete unconnected spots of light such that when the light source is activated to transmit light through the pattern generator, a ratio of illuminated area to non-illuminated area for each orthogonal plane in the field of illumination is 1:150-1:16.

14. The apparatus according to claim 1, wherein a light throughput efficiency of the pattern generator is at least 90%.

15. A method of generating a digital three-dimensional model of an intraoral surface, comprising:
driving one or more light projectors of an intraoral scanner to project a light pattern on the intraoral surface;
driving one or more light field cameras of the intraoral scanner to capture a plurality of images that depict a light field resulting from at least a portion of the projected light pattern reflecting off of the intraoral surface, wherein the light field contains information about an intensity of the light pattern reflecting off of the intraoral surface and a direction of light rays, wherein the plurality of images comprise a central region and a peripheral region, and wherein the central region has a higher spatial resolution than the peripheral region;
receiving the plurality of images that depict at least a portion of a projected light pattern on the intraoral surface; and
using information from the captured light field depicted in the plurality of images to generate the digital three-dimensional model of the intraoral surface.

16. The method of claim 15, wherein at least 40% of the light pattern from each light projector is in a field of view of at least one of the one or more light field cameras.

17. The method according to claim 15, wherein each light projector is a structured light projector that has a field of illumination of 60-120 degrees, and wherein a projector focal plane of each light projector is located between 3 mm and 40 mm from a light source of the light projector.

18. The method according to claim 15, wherein each light field camera has a field of view of 60-120 degrees and is configured to focus at a camera focal plane that is located between 3 mm and 40 mm from the light field camera.

19. The method according to claim 15, wherein the plurality of images comprise images from a plurality of light field cameras.

20. The method according to claim 15, wherein the light field further contains information about phase-encoded depth via which depth can be estimated from different directions.

21. The method according to claim 15, further comprising:
receiving a plurality of two-dimensional color images of the intraoral surface; and
determining color data for the digital three-dimensional model of the intraoral surface based on the plurality of two-dimensional color images.

22. A method of generating image data, comprising:
generating, by one or more light projectors disposed in a probe of an intraoral scanner, respective light patterns, wherein generating a light pattern by a light projector of the one or more light projectors comprises:
  generating light by the light projector;
  focusing the light at a projector focal plane; and
  generating, by a pattern generator, a light pattern from the light at the projector focal plane;
projecting the respective light patterns of the one or more light projectors toward an intraoral surface disposed in a field of illumination of the one or more light projectors;
receiving, by one or more light field cameras disposed in the probe, a light field resulting from at least a portion of the respective light patterns reflecting off of the intraoral surface, wherein the light field contains information about an intensity of the light pattern reflecting off of the intraoral surface and a direction of light rays, and wherein the one or more light field cameras comprise a first sensor region having a first spatial resolution and a second sensor region having a second spatial resolution that is lower than the first spatial resolution;
generating a plurality of images by the one or more light field cameras that depict the light field, wherein the plurality of images comprise a first image region having the first spatial resolution and a second image region having the second spatial resolution; and
sending the plurality of images to a data processing system.

23. The method of claim 22, wherein the one or more light projectors and the one or more light field cameras are disposed in a distal end of the probe, and wherein the one or more light projectors and the one or more light field cameras are positioned such that (a) each light projector directly faces the intraoral surface, (b) each light field camera directly faces the intraoral surface, and (c) at least 40% of the light pattern from each light projector is in a field of view of at least one of the light field cameras.

24. The method of claim 22, wherein the one or more light projectors and the one or more light field cameras are disposed in a proximal end of the probe, the method further comprising:
  using a mirror to reflect the respective light patterns onto the intraoral surface; and
  using the mirror to reflect the light field reflected from the intraoral surface into the one or more light field cameras.

25. The method of claim 22, wherein the first sensor region is a central region and the second sensor region is a peripheral region.

26. An apparatus for intraoral scanning, the apparatus comprising:
  an elongate handheld wand comprising a probe at a distal end of the elongate handheld wand, the probe having a proximal end and a distal end;
  one or more light projectors disposed in the distal end of the probe, each light projector of the one or more light projectors comprising:
    a light source, the light projector being configured to focus light from the light source at a projector focal plane; and
    a pattern generator disposed in an optical path between the light source and the projector focal plane, the pattern generator configured to generate a light pattern at the projector focal plane when the light source is activated to transmit light through the pattern generator;
    a beam shaping optical element; and
    an optical element disposed between the beam shaping optical element and the pattern generator, the optical element being configured to generate a Bessel beam when the light source is activated to transmit light through the optical element,
  one or more light field cameras disposed in the distal end of the probe and configured to capture a light field that contains information about an intensity of the light pattern reflecting off of an intraoral surface and a direction of light rays, each light field camera comprising:
    a light field camera sensor, the light field camera sensor comprising (i) an image sensor comprising an array of sensor pixels, and (ii) an array of micro-lenses disposed in front of the image sensor such that each micro-lens is disposed over a sub-array of the array of sensor pixels; and
    an objective lens disposed in front of the light field camera sensor and configured to form an image of an object being scanned onto the light field camera sensor;
  wherein the one or more light projectors and the one or more light field cameras are positioned such that (a) each light projector directly faces an object outside of the elongate handheld wand placed in its field of illumination, (b) each camera directly faces the object outside of the elongate handheld wand placed in its field of view, and (c) at least 40% of the light pattern from each projector is in the field of view of at least one of the one or more light field cameras.

* * * * *